US006476216B1

(12) United States Patent
Just et al.

(10) Patent No.: US 6,476,216 B1
(45) Date of Patent: Nov. 5, 2002

(54) PREPARATION OF PHOSPHOROTHIOATE OLIGOMERS

(75) Inventors: George Just, Ile Cadieux (CA); Zhili Xin, Gurnee, IL (US); Eric Marsault, Sherbrooke (CA); Yi Jin, Winnipeg (CA); Jianchao Wang, Montreal (CA)

(73) Assignee: McGill University (CA)

( * ) Notice: Subject to any disclaimer, the term of this patent is extended or adjusted under 35 U.S.C. 154(b) by 0 days.

(21) Appl. No.: 09/051,610

(22) PCT Filed: Oct. 18, 1996

(86) PCT No.: PCT/IB96/01185

§ 371 (c)(1),
(2), (4) Date: Dec. 3, 1998

(87) PCT Pub. No.: WO97/14710

PCT Pub. Date: Apr. 24, 1997

Related U.S. Application Data

(63) Continuation-in-part of application No. 08/546,198, filed on Oct. 20, 1995, now Pat. No. 5,734,041.

(51) Int. Cl.[7] .............................................. C07H 21/00
(52) U.S. Cl. .................... 536/25.34; 536/25.3; 536/26.1
(58) Field of Search ........................... 536/25.3, 25.34, 536/26.1

(56) References Cited

U.S. PATENT DOCUMENTS

| | | | |
|---|---|---|---|
| 3,846,374 A | 11/1974 | Farley et al. | 260/551 P |
| 4,415,732 A | 11/1983 | Caruthers et al. | 536/27 |
| 4,458,066 A | 7/1984 | Caruthers et al. | 536/27 |
| 4,500,707 A | 2/1985 | Caruthers et al. | 536/27 |
| 4,668,777 A | 5/1987 | Caruthers et al. | 536/27 |
| 4,725,677 A | 2/1988 | Köster et al. | 536/27 |
| 4,973,679 A | 11/1990 | Cruthers et al. | 536/27 |
| 5,132,418 A | 7/1992 | Caruthers et al. | 536/27 |
| RE34,069 E | 9/1992 | Köster et al. | 536/27 |
| 5,646,267 A | 7/1997 | Stec et al. | 536/25.33 |

FOREIGN PATENT DOCUMENTS

| | | |
|---|---|---|
| WO | WO 88/02004 | 3/1988 |
| WO | WO 92/02258 | 2/1992 |
| WO | WO 96/39413 | 12/1996 |

OTHER PUBLICATIONS

Beaucage, A simple and efficient prep. of deoxynucleoside . . . , Tetrahedron Letters, vol. 25(4), pp. 375–378, 1984.*

Bielinska, A. et al., "Regulation of Gene Expression with Double–Stranded Phosphorothioate Oligonucleotides", *Science*, 1990, 250, 997–1000.

Brody, R.S. et al., "Stereochemical Course of Nucleotidyl Transfer Catalyzed by Bacteriophage T7 Induced DNA Polymerase", *Biochemistry*, 1982, 21, 2570–2572.

Brody, R.S. et al., "Unambiguous Determination of the Stereochemistry of Nucleotidyl Transfer Catalyzed by DNA Polymerase I from *Escherichia coli*", *Biochemistry*, 1981, 20, 1245–1252.

Bryant, F. et al., "Stereochemical Course of the Reaction Catalyzed by 5′–Nucleotide Phosphodiesterase from Snake Venom", *Biochemistry*, 1979, 2825–2827.

Burgers, P.M.J. et al., "A Study of the Mechanism of DNA Polymerase I from *Escherichia coli* with Diastereomeric Phosphorothioate Analogs of Deoxyadenosine Triphosphate", *J. Biol. Chem.*, 1979, 254, 6889–6893.

Burgers, P.M.J. et al., "Absolute configuration of the diastereomers of adenosine 5′–O–(1–thiotriphosphate): Consequences for the stereochemistry of polymerization by DNA–dependent RNA Polymerase from *Escherichia coli*", *Proc. Natl. Acad. Sci.*, 1978, 75, 4798–4800.

Cruse, W.B.T. et al., "Chiral Phosphorothiate Analogues of B–DNA The Crystal Structure of Rp—d↑Gp(S)CpGp(S)CpGp(S)C↑", *J. Mol. Biol.*, 1986, 192, 891–905.

Eckstein, F. et al., "Assignment of Resonances in the Phosphorus–31 Nuclear Magnetic Resonance Spectrum of Poly [d(A–T)] from Phosphorothioate Substitution," *Biochemistry*, 1983, 22, 4546–4550.

Fujii, et al., "Acylphosphonates. 7.[1] A New Method for Stereospecific and Stereoselective Generation of Dideoxyribonucleoside Phosphorothioates via the Acylphosphonate Intermediates", *Tetrahedron* 1987, 43, 3395–3407.

Gupta, A. et al., "Template–Primer–dependent Turnover of $(S_p)$–dATPαS by T4 DNA Polymerase", *J. Biol. Chem.*, 1982, 257, 7689–7692.

Hall, G. et al., "Platinum(II) Complexes of P(III) Cyclophosphamide Derivatives", *Phosphorus & Sulphur*, 1979, 7, 235–240.

Huang, Y. et al., "Study of the Conformational Equilibria of 2–Z–3–Methyl–1,3,2–oxazaphosphorinanes. Steric and Stereoelectronic Influences on the Orientation of the $Me_2N$ Substituent on Three–Coordinate Phosphorus", *J. Org. Chem*, 1995, 60, 4767–4773.

Iyer, R.P. et al., "3H–1,2–Benzodithiole–3–one 1,1–Dioxide as an Improved Sulfurizing Reagent in the Solid–Phase Synthesis of Oligodeoxyribonucleoside Phosphorothioates", *J. Am. Chem. Soc.*, 1990, 112, 1253–1254.

Iyer, R.P. et al., "The Automated Synthesis of Sulfur–Containing Oligodeoxyribonucleotides Using 3H–1, 2–Benzodithiol–3–one 1,1–Dioxide as a Sulfur–Transfer Reagent", *J. Org. Chem.*, 1990, 55, 4693–4699.

(List continued on next page.)

Primary Examiner—Johann Richter
Assistant Examiner—Howard Owens
(74) Attorney, Agent, or Firm—Woodcock Washburn LLP

(57) ABSTRACT

The present invention is directed to methods for solid phase nucleotide synthesis utilizing substituted imidazole catalysts.

26 Claims, No Drawings

OTHER PUBLICATIONS

Jager, A. et al., "Oligonucleotide N–Alkylphosphoroamidates: Synthesis and Binding to Polynucleotides", *Biochem.*, 1988, 27, 7237–7246.

Jin, Y. et al., "A Stereoselective Synthesis of Dinucleotide Phosphorothioates, using Chiral Phosphoramidites as Intermediates", *Tetrahedron Letts.*, 1996, 37, 973–976.

Kamer, P.C.J. et al., "An Efficient Approach Toward the Synthesis of Phosphorothioate Diesters via the Schonberg Reaction", *Tetrahedron Letts.*, 1989, 30, 6757–6760.

Koole, L.H. et al., "Enhanced stability of a Watson & crick DNA duplex structure by methylation of the phosphate groups in one strand", *Proc. K. New. Acad. wet.*, 1987, 90, 41–46.

Letsinger, R.L. et al., "Effects of pendant groups at phosphorus on binding properties of d–ApA analogues", *Nuc. Acids. Res.*, 1986, 14, 3487–3498.

Marsault, E. et al., "Diastereoselective Synthesis of Phosphite Triesters Through a New Bicyclic Intermediate", *Tetrahedron Letts.*, 1996, 37, 977–980.

Miller, P.S. et al., "Biochemical and Biological Effects of Nonionic Nucleic Acid Methylphosphonates", *Biochem.*, 1981, 20, 1874–1880.

Niewiarowski, W. et al., "Diastereomers of Thymidine 3'–O–(Methanephosphonothioate): Synthesis, Absolute Configuration and Reaction with 3'–Methoxyacetylthymidine Under Conditions of Triester Approach to Oligonucleotide Synthesis," *Acta Biochimica Polonica*, 1987, 34, 217–232.

Nifantyev, E.E. et al., "1,3,2–Oxazaphosphorinanes in rhodium(I) complexes", *J. Organometallic Chem.*, 1987, 336, 237–247.

Nuretdinov, I. et al., "Nuclear Quadrupole Resonance of Chlorides & Amides of Phosphorus(III) Cyclic Acids", *Chem. Abstr.*, 1979, 90, 612.

Rao, M.V. et al., "Dibenzoyl Tetrasulphide–A Rapid Sulphur Transfer Agent in the Synthesis of Phosphorothioate Analogues of Oligonucleotides", *Tetrahedron Letts.*, 1992, 33, 4839–4842.

Romaniuk, P.J. et al., "A Study of the Mechanism of T4 DNA Polymerase with Diastereomeric Phosphorothioate Analogues of Deoxyadenosine Triphosphate," *The Journal of Biological Chemistry*, 1982, 257, 7684–7688.

Stec, W.J., "Stereospecific Synthesis of Oligonucleotide P–Chiral Analogues", *Oligonucleotides as Antisense Inhibitors of Gene Expression: Therapeutic Implications*, Jun. 18–21, 1989, Meeting Abstracts. Dept. of Bioorganic Chem., Poland.

Stec, W.J. et al., "Stereocontrolled Synthesis of Oligo–(nucleoside phosphorothioate)s", *Angew. Chem. Int. Ed. Engl.*, 1994, 33, 709–722.

Stec, W.J. et al., "Reversed–Phase High–Performance Liquid Chromatographic Separation of Diastereomeric Phosphorothiate Analogues of Oligodeoxyribonucleotides and other Back–Bone–Modified Congeners of DNA", *J. Chromatography*, 1985, 326, 263–280.

Takahata, H. et al., "Concise Synthesis of Natural γ–Butyrolactones, (+)–trans–Whisky Lactone, (+)–trans–Cognac Lactone, (−)–Methylenolactiocin, (+)–Nephrosteranic Acid, and (+)–Roccellaric Acid Using Novel Chiral Butenolide Synthons", *J. Org. Chem.*, 1995, 60, 5628–5633.

Ueda, T. et al., "Phosphorothioate–containing RNAs show mRNA activity in the prokaryotic translation systems in vitro", *Nucl. Acids Res.*, 1991, 19, 547–552.

Vu, H. et al., "Internucleotide Phosphite Sulfurization with Tetraethylthiuram Disulfide. Phosphorothioate Oligonucleotide Synthesis via Phosphoramidite Chemistry", *Tetrahedron Letts.*, 1991, 32, 3005–3008.

Wu, H. et al., "Inhibition of in vitro transcription by specific double–stranded oligodeoxyribonucleotides", *Gene*, 1990, 89, 203–209.

Xin, Z. et al., "Diastereoselective Synthesis of Phosphite Triesters", *Tetrahedron Letts.*, 1996, 37, 969–972.

Moore, M.F. et al., "Conceptual Basis of the Selective Activation of Bis(dialkylamino)methoxyphosphines by Weak Acids and Its Application Toward the Preparation of Deoxynucleoside Phosphoramidites in Situ", *J. Org. Chem.*, (1985), vol. 50, pp. 2019–2025.

* cited by examiner

PREPARATION OF PHOSPHOROTHIOATE OLIGOMERS

CROSS REFERENCE TO RELATED APPLICATIONS

This application is a continuation in part of U.S. application Ser. No. 08/546,198, filed Oct. 20, 1995, now U.S. Pat. No. 5,734,041.

FIELD OF THE INVENTION

This invention relates to methods for the preparation of diastereomerically enriched phosphorothioate linked oligonucleotides, and to intermediates useful in their preparation. This invention also relates to sequence-specific phosphorothioate oligonucleotides having chiral phosphorus linkages and to a novel chemical synthesis of these and other oligonucleotides.

BACKGROUND OF THE INVENTION

It is well known that most of the bodily states in multicellular organisms, including most disease states, are effected by proteins. Such proteins, either acting directly or through their enzymatic or other functions, contribute in major proportion to many diseases and regulatory functions in animals and man. Classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect might be obtained with minimal side effects. It is the general object of such therapeutic approaches to interfere with or otherwise modulate gene expression which would lead to undesired protein formation.

One method for inhibiting specific gene expression is with the use of oligonucleotides. Oligonucleotides complementary to a specific target messenger RNA (mRNA) sequence are used. Several oligonucleotides are currently undergoing clinical trials for such use.

Transcription factors interact with double-stranded DNA during regulation of transcription. Oligonucleotides can serve as competitive inhibitors of transcription factors to modulate the action of transcription factors. Several recent reports describe such interactions (see, Bielinska, et. al., *Science* 1990, 250, 997–1000; and Wu, et al., *Gene* 1990, 89, 203–209.)

Oligonucleotides also have found use in diagnostic tests. Such diagnostic tests can be performed using biological fluids, tissues, intact cells or isolated cellular components. As with the above gene expression inhibition, diagnostic use can take advantage of an oligonucleotide's ability to hybridize with a complementary strand of nucleic acid. Hybridization is the sequence specific hydrogen bonding of oligonucleotides via Watson-Crick and/or Hoogsteen base pairs to RNA or DNA. The bases of such base pairs are said to be complementary to one another.

Oligonucleotides are also widely used as research reagents. They are useful for understanding the function of many other biological molecules as well as in the preparation of such other biological molecules. One particular use, the use of oligonucleotides as primers in the reactions associated with polymerase chain reaction (PCR), has been the cornerstone for the establishment of an ever expanding commercial business. The use of such PCR reactions has seemingly "exploded" as more and more use of this very important biological tool is made. The uses of PCR have extended into many areas in addition to those contemplated by its Nobel laureate inventor. Examples of such new areas include forensics, paleontology, evolutionary studies and genetic counseling to name just a few. Primers are needed for each of these uses. Oligonucleotides, both natural and synthetic, serve as the primers.

Oligonucleotides also are used in other laboratory procedures. A number of these uses are described in common laboratory manuals such as *Molecular Cloning, A Laboratory Manual*, Second Ed., J. Sambrook, et al., Eds., Cold Spring Harbor Laboratory Press, 1989; and *Current Protocols In Molecular Biology*, F. M. Ausubel, et. al., Eds., Current Publications, 1993. Such uses include Synthetic Oligonucleotide Probes, Screening Expression Libraries with Antibodies and Oligonucleotides, DNA Sequencing, In Vitro Amplification of DNA by the Polymerase Chain Reaction and Site-directed Mutagenesis of Cloned DNA from Book 2 of *Molecular Cloning, A Laboratory Manual*, ibid. and DNA-Protein Interactions and The Polymerase Chain Reaction from Vol. 2 of *Current Protocols In Molecular Biology*, ibid.

To supply the users of oligonucleotides, many scientific journals now contain advertisements for either oligonucleotide precursors or for custom-synthesized oligonucleotides. This has become an important commercial use of oligonucleotides. Oligonucleotides can be synthesized to have properties that are tailored for the desired use. Thus, a number of chemical modifications have been introduced into oligonucleotides to increase their usefulness in diagnostics, as research reagents, and as therapeutic entities. These modifications are designed, for example, to increase binding to a target nucleic acid strand, to assist in identification of the oligonucleotide or an oligonucleotide-target complex, to increase cell penetration, to provide stability against nucleases and other enzymes that degrade or interfere with the structure or activity of the oligonucleotides, to provide a mode of disruption (terminating event) once sequence-specifically bound to a target, or to improve the pharmacokinetic properties of the oligonucleotides.

Since they exist as diastereomers, phosphorothioate, methylphosphonate, phosphotriester, phosphoramidate and other phosphorus oligonucleotides synthesized using known, automated techniques result in mixtures of Rp and Sp diastereomers at the individual phosphorothioate, methylphosphonate, phosphotriester, phosphoramidate or other phosphorus linkages. Thus, a 15-mer oligonucleotide containing 14 asymmetric linkages has $2^{14}$, i.e. 16,384, possible stereoisomers. It is possible that oligomers having diastereomerically enriched linkages could possess advantages in hybridizing to a target mRNA or DNA. Accordingly, there is a need for such oligomers.

Miller, P. S., McParland, K. B., Jayaraman, K., and Ts'o, P.O.P (1981), *Biochemistry*, 20:1874, found that small di-, tri- and tetramethylphosphonate and phosphotriester oligonucleotides hybridize to unmodified strands with greater affinity than natural phosphodiester oligonucleotides. Similar increased hybridization was noted for small phosphotriester and phosphoramidate oligo-nucleotides; Koole, L. H., van Genderen, M. H. P., Reiners, R. G., and Buck, H. M. (1987), *Proc. K. Ned. Adad. Wet.,* 90:41; Letsinger, R. L., Bach, S. A., and Eadie, J. S. (1986), *Nucleic Acids Res.,* 14:3487; and Jager, A., Levy, M. J., and Hecht, S. M. (1988), *Biochemistry,* 27:7237. The effects of the diastereomers of undefined stereochemistry on hybridization becomes even more complex as chain length increases.

Bryant, F. R. and Benkovic, S. J. (1979), *Biochemistry,* 18:2825 studied the effects of diesterase on the diastereomers of ATP. Published patent application PCT/US88/03634 discloses dimers and trimers of 2',5'-linked diastereomeric adenosine units. Niewiarowski, W., Lesnikowski, Z. J., Wilk, A., Guga, P., Okruszek, A., Uznanski, B., and Stec, W. (1987), *Acta Biochimica Polonia,* 34:217, synthesized dimers of thymidine having high diastereomeric excess, as did Fujii, M., Ozaki, K., Sekine, M., and Hata, T. (1987), *Tetrahedron,* 43:3395.

Stec, W. J., Zon, G., and Uznanski, B. (1985), *J. Chromatography,* 326:263, have reported the synthesis of certain mixtures of phosphorothioates or methyphosphonate oligonucleotides and have separated them by chromatography. However, they were only able to separate the diastereomers of certain small oligomers having a limited number of diastereomerically pure phosphorus linkages.

In a preliminary report, J. W. Stec, Oligonucleotides as antisense inhibitors of gene expression: Therapeutic implications, meeting abstracts, Jun. 18–21, 1989, noted that a non-sequence-specific thymidine homopolymer octamer—i.e. a $(dT)_8$-mer, having "all-except-one" Rp configuration methylphosphonate linkages—formed a thermodynamically more stable hybrid with a 15-mer deoxyadenosine homopolymer—i.e. a $d(A)_{15}$-mer—than did a similar thymidine homopolymer having "all-except-one" Sp configuration methylphosphonate linkages. The hybrid between the "all-except-one" Rp $(dT)_8$-mer and the $d(A)_{15}$-mer had a Tm of 38° C. while the Tm of the "all-except-one" Sp $(dT)_8$-mer and the $d(A)_{15}$-mer was <0° C. The hybrid between a $(dT)_8$-mer having natural phosphodiester linkages, i.e. octathymidylic acid, and the $d(A)_{15}$-mer was reported to have a Tm of 14° C. The "all-except-one" thymidine homopolymer octamers were formed from two thymidine methylphosphonate tetrameric units with high diastereomeric excess linked by a natural phosphodiester linkage.

Six or more nucleotides units are generally necessary for an oligonucleotide to be of optimal use in applications involving hybridization. It is often preferred to have even more nucleoside units for best performance, often as many as 10 to 30. Because it has not been possible to stereochemically resolve more than two or three adjacent phosphorus linkages, the effects of induced chirality in the phosphorus linkages of chemically synthesized oligonucleotides has not been well assessed heretofore. This is because with few limited exceptions, the sequence-specific phosphorothioate, methylphosphonate, phosphotriester or phosphoramidate oligonucleotides obtained utilizing known automated synthetic techniques have been mixtures with no diastereomeric excess.

Some aspects of the use of enzymatic methods to synthesize oligonucleotides having chiral phosphorus linkages have been investigated. Burgers, P. M. J. and Eckstein, F. (1979), *J. Biological Chemistry,* 254:6889; and Gupta, A., DeBrosse, C., and Benkovic, S. J. (1982) *J. Bio. Chem.,* 256:7689 enzymatically synthesized diastereomerically pure polydeoxyadenylic acid having phosphorothioate linkages. Brody, R. S. and Frey, P. S. (1981), *Biochemistry,* 20:1245; Eckstein, F. and Jovin, T. M. (1983), *Biochemistry,* 2:4546; Brody, R. S., Adler, S., Modrich, P., Stec, W. J., Leznikowski, Z. J., and Frey, P. A. (1982) *Biochemistry,* 21: 2570–2572; and Romaniuk, P. J. and Eckstein, F. (1982) *J. Biol. Chem.,* 257:7684–7688 all enzymatically synthesized poly TpA and poly ApT phosphorothioates while Burgers, P. M. J. and Eckstein, F. (1978) *Proc. Natl. Acad. Sci. USA,* 75: 4798–4800 enzymatically synthesized poly UpA phosphorothioates. Cruse, W. B. T., Salisbury, T., Brown, T., Cosstick, R. Eckstein, F., and Kennard, O. (1986), *J. Mol. Biol.,* 192:891, linked three diastereomeric Rp GpC phosphorothioate dimers via natural phosphodiester bonds into a hexamer. Most recently Ueda, T., Tohda, H., Chikazuni, N., Eckstein, R., and Watanabe, K. (1991) *Nucleic Acids Research,* 19:547, enzymatically synthesized RNA's having from several hundred to ten thousand nucleotides incorporating Rp linkages of high diastereomeric excess. Enzymatic synthesis, however, is disadvantageous in that it depends on suitable polymerases that may or may not be available, especially for modified nucleoside precursors.

As reviewed by W. J. Stec and A. Wiek (1994), *Angew. Chem. Int.* Ed. English 33:709, the oxathiaphospholane method has been successful for the preparation of phosphorothioates with defined stereochemistry. However, it suffers from disadvantages, such as the non-trivial preparation of diastereomerically pure oxathiaphospholane, and the difficulty in synthesizing and isolating satisfactorily pure oligomers longer than 12-mers.

It would therefore be of great advantage to provide oligonucleotides having phosphorus linkages with controlled stereochemistry.

OBJECTS OF THE INVENTION

It is one object of this invention to provide sequence-specific oligonucleotides having chirally pure phosphorothioate linkages with high diastereomeric excess.

Another object is to provide phosphorus-linked oligonucleotides having substantially all Rp or all Sp linkages.

A further object is to provide research and diagnostic materials for assaying bodily states in animals, especially diseased states.

It is yet another object to provide new methods for synthesizing sequence-specific oligonucleotides having chirally pure phosphorothioate linkages, and useful intermediates therefor.

SUMMARY OF THE INVENTION

The present invention provides stereoselective methods for preparing sequence-specific oligonucleotides having chiral phosphorus linkages. In certain preferred embodiments, these methods comprise the steps of:

reacting a first synthon of Formula I:

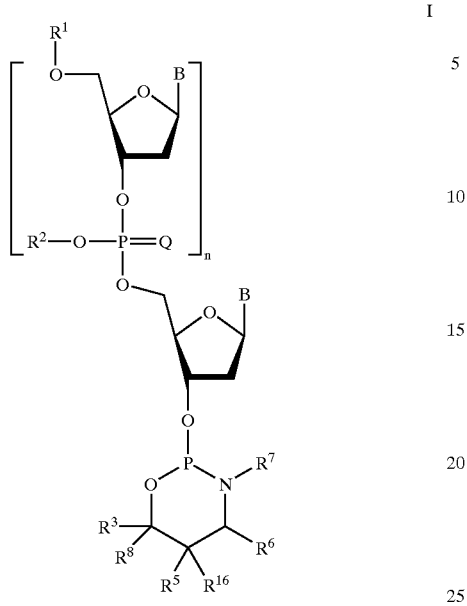

wherein:
Q is independently O or S;
$R^1$ is a hydroxyl protecting group;
$R^2$ is a chiral auxiliary of formula $-C(R^8)R^3-C(R^{16})R^5-CHR^6-NHR^7$;
$R^3$ is hydrogen, alkyl, cyanomethyl, monohalomethyl, dihalomethyl, trihalomethyl, $-CH_2R^4$, $-CH_2Si(R^4)_3$, or $-CH_2-SO_kR^4$ where k is 0, 1 or 2;
$R^4$ is independently alkyl, aryl, aralkyl or alkaryl having up to 15 carbon atoms, $-N(R_{70})-C(=O)-R_{71}$, $-S-C(=O)-R_{70}$, or $-O-C(=O)-O-N(R_{70})(R_{71})$;
$R_{70}$ and $R_{71}$ are each independently alkyl, α-halo substituted alkyl, aralkyl, α-halo substituted aralkyl, or aryl substituted with up to three electronegative groups;
$R^5$ is H, $-CN$, $-Si(R^4)_3$, $SO_kR^4$ or halogen;
or $R^8$ and $R^{16}$ are each H, and $R^3$ and $R^5$, together, form one of the structures:

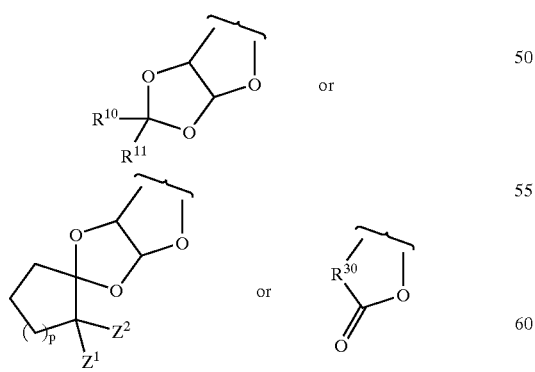

wherein:
$R^{10}$ and $R^{11}$ are H, alkyl having from 1 to about 10 carbons, $-CH_2C(=O)OR^{22}$, $-CH_2CN$, $-CH_2Si(CH_3)_3$, or o- or p-$C_6H_4-R^{21}$;

$R^{21}$ is hydrogen, $-O-C(=O)CH_3$, alkoxy having from 1 to about 10 carbons, $-NO_2$, or $-N(R^{22})_2$;
$R^{22}$ is independently H or alkyl having from one to about 10 carbon atoms;
p is 1 or 2;
$Z^1$ and $Z^2$ are independently halogen, $-CN$, $-Si(CH_3)_3$, or $-C(=O)OR^{22}$;
$R^{30}$ is hydrogen, $-O-C(=O)CH_3$, alkoxy having from 1 to about 10 carbons, or $-O-Si(R_4)_3$;
$R^6$ is H, alkyl or aralkyl having up to 15 carbon atoms;
or $R^5$ and $R^6$, together with the atoms to which they are attached, form a 5 or 6 membered ring;
$R^7$ is alkyl or aralkyl having up to 15 carbon atoms;
or $R^6$ and $R^7$, together, form one of the structures

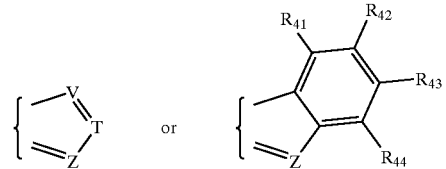

wherein
V, T, and Z are independently CH or N;
$R_{41}$, $R_{42}$, $R_{43}$, and $R_{44}$ are each independently H or an electronegative group;
$R^8$ is H or methyl;
$R^{16}$ is H, alkyl or aralkyl having up to 15 carbon atoms;
B is a nucleobase; and
n is an integer from 0 to 50;

with a second synthon of Formula II:

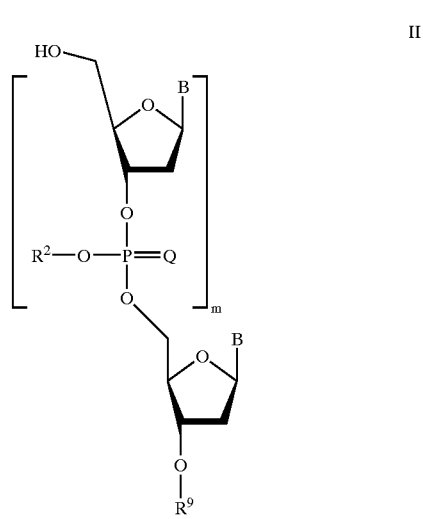

wherein:
$R^9$ is a hydroxyl protecting group or a linker connected to a solid support; and
m is an integer from 0 to 50;

for a time and under reaction conditions effective to form a third synthon of Formula III:

III

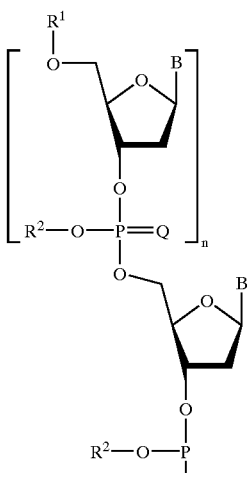

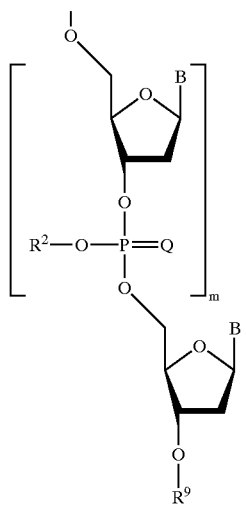

and contacting said third synthon with a sulfurizing agent to form an oligomer of Formula IV:

IV

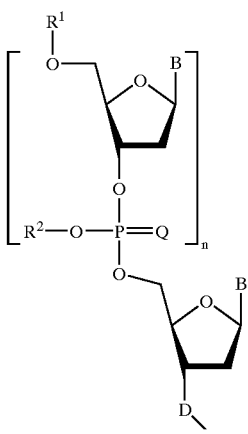

-continued

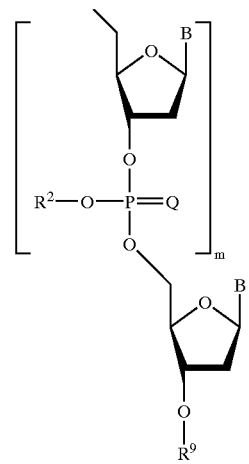

wherein D is said phosphorothioate linkage having the formula:

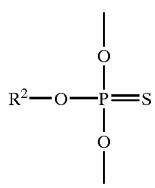

In preferred embodiments, said phosphorothioate linkage is diastereomerically enriched. In other preferred embodiments about 75% of the phosphorothioate linkage is in a single stereoisomeric form. In further preferred embodiments about 85% of the phosphorothioate linkage is in a single stereoisomeric form. In especially preferred embodiments about 95% of the phosphorothioate linkage is in a single stereoisomeric form. Most preferably, the phosphorothioate linkage is in a single stereoisomeric form, substantially free of other stereoisomeric forms. Preferably, the first synthon is in a single stereoisomeric form, substantially free of other stereoisomeric forms.

In some preferred embodiments n is 0. In further preferred embodiments, $R^1$ groups are subsequently removed to yield new second synthons for iterative synthesis, and chiral auxiliaries are removed after iterative synthesis is completed. In preferred embodiments of the present methods the oligomer of Formula IV contains a plurality of phosphorothioate linkages.

Preferably, first and second synthons are reacted at a temperature of from about −20° C. to about 40° C, with from about −15° C. to about 0° C. being more preferred.

In some preferred embodiments the first synthon is formed by reacting a compound of Formula V:

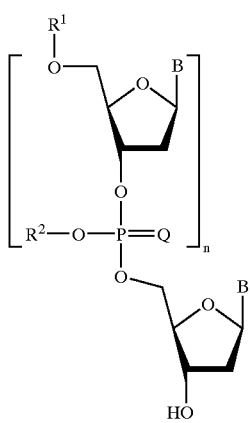

with an azaphospholane of Formula VIa:

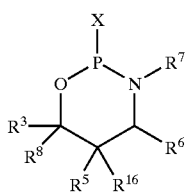

wherein $R^3$—$R^8$ are as defined above; and X is halogen, dialkylamino, imidazole, triazole or substituted phenoxy wherein said substituents are electron withdrawing, preferably halogen or nitro.

In some embodiments the azaphospholane described above is produced by reacting a reagent of formula HO—C($R^8$)$R^3$—C($R^{16}$)$R^5$—CHR$^6$—NHR$^7$ and a phosphorus trihalide, phosphorus tri(dialkylamide), phosphorus triphenoxide or phosphorus triimidazolide.

In more preferred embodiments the first synthon is formed by reacting a compound of Formula VII:

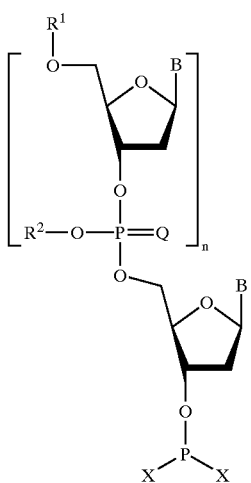

and a γ-amino alcohol of formula HO—C($R^8$)$R^3$—C($R^{16}$)$R^5$—CHR$^6$—NHR$^7$. Preferably, X is chlorine, dialkylamino or diphenoxy, and said reaction is stereoselective. It is especially preferred that the first synthon is in a single stereoisomeric form, substantially free of other stereoisomeric forms.

In some preferred embodiments the reaction of first and second synthons is performed in the presence of a catalyst, said catalyst preferably having one of the Formulas VIII or IX:

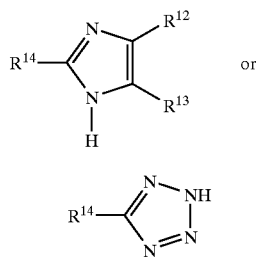

wherein:
$R^{12}$ and $R^{13}$ are independently hydrogen, halogen, cyano, nitro, alkyl having from one to 10 carbons, substituted alkyl having from one to 10 carbons, an ester group, or $R^{12}$ and $R^{13}$ together with the carbon atoms to which they are attached, form a substituted or unsubstituted phenyl ring where said substituents are electron withdrawing; and $R^{14}$ is hydrogen, halogen, cyano, nitro, thio, alkyl having from one to 10 carbons, substituted alkyl having from one to 10 carbons, norbornyl, substituted norbornyl, aryl, substituted aryl wherein said substituents are electron withdrawing, or has the formula:

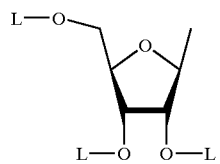

wherein L is protecting group.

In some preferred embodiments $R^{14}$ is halogen or nitro, preferably bromine, and $R^{12}$ and $R^{13}$ are each halogen or each cyano, with cyano being especially preferred.

Other preferred embodiments $R^{14}$ has one of the formulas:

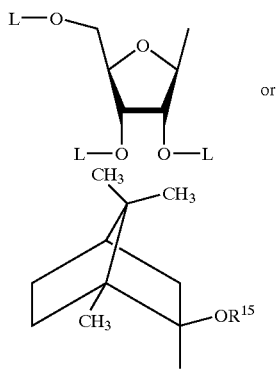

wherein $R^{15}$ is H, methyl, trialkylsilyl or acetyl.

In some preferred embodiments of the method $R^3$ is cyanomethyl or —CH$_2$—SO$_k$R$^4$ where k is 0, 1 or 2, and $R^7$ is lower alkyl or aralkyl.

In further preferred embodiments said first synthon has one of the Formulas Xa, XIa, XIIa, XIIIa or XXa:

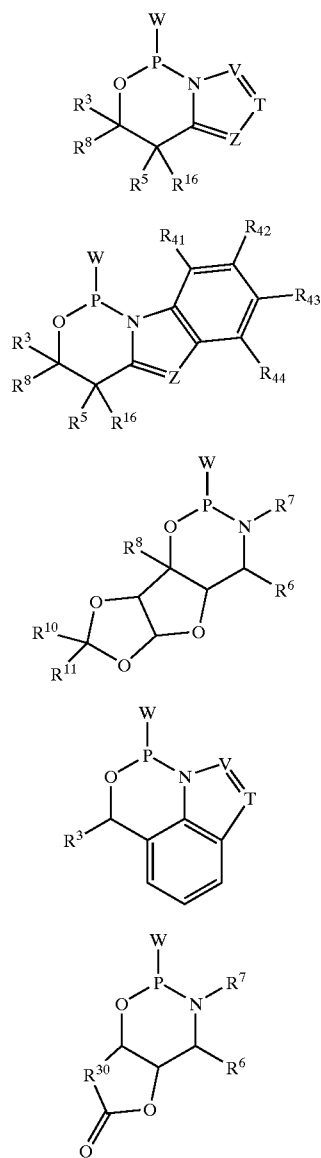
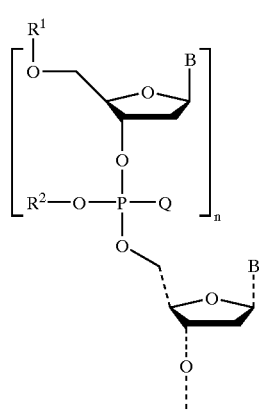
wherein W has the formula:
and R$^1$—R$^{16}$, V, T and Z are as defined above.
Other preferred first synthons have the Formula Xb or Xc:
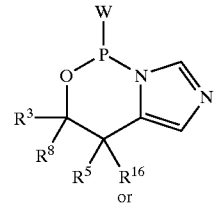
Xb
or
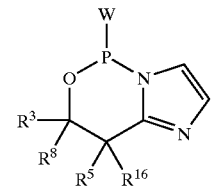
Xc
More preferred first synthons have the Formula XVIIa or XVIIIa:
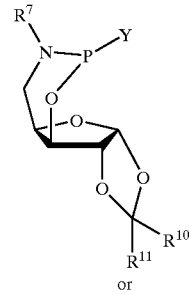
XVIIa
or
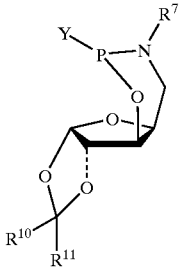
XXVIIIa
Particularly preferred first synthons have the Formula XIVa:
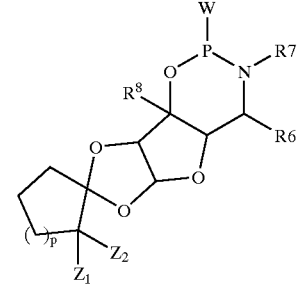
XIVa
Especially preferred first synthons have the Formula XVa or XVIa:

XVa

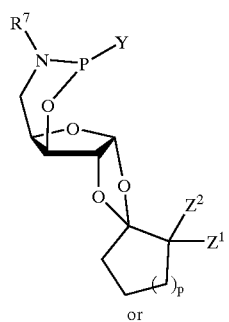

or

XVIa

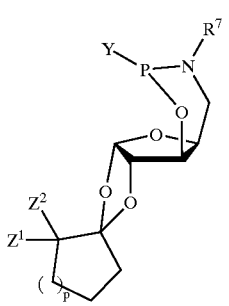

In preferred embodiments of the methods of the invention R[1] groups are removed from the oligomers, thus creating new second synthons for further iterative synthesis.

Also provided according to the invention are phosphorothioate oligomers produced by the method of claim 1, and azaphospholanes having Formula VIb:

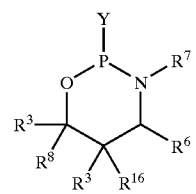

In preferred embodiments of the invention, 75% of said azaphospholanes having Formula VIb are in a single stereoisomeric form, with 85% being more preferred, and 95% being particualrly preferred. In especially preferred embodiments, the azaphospholanes having Formula VIb are in a single stereoisomeric form, substantially free of other stereoisomeric forms.

In preferred embodiments the azaphospholane has one of the Formulas Xb, XIb, XIIb, XIIIb, Xd, Xe or XXb:

Xb

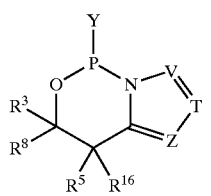

XIb

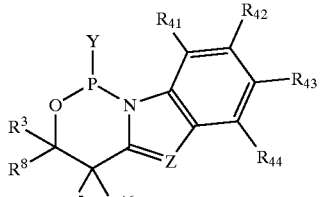

XIIb

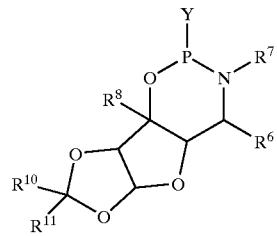

XIIIb

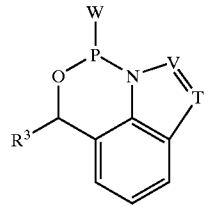

Xd

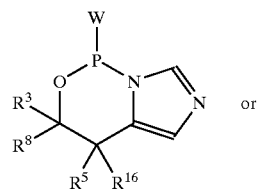

or

Xe

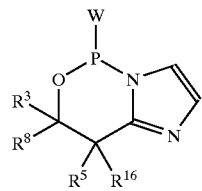

XXb

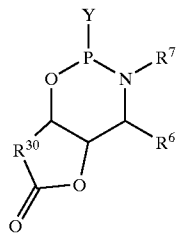

In other preferred embodiments the azaphospholane has the Formula XVIIb or XVIIIb:

XVIIb

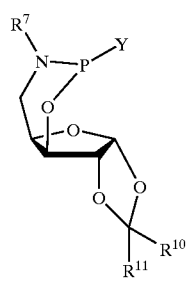

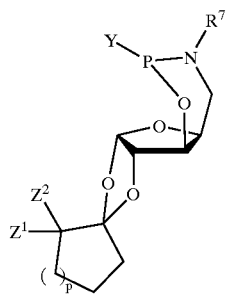

XVIb or

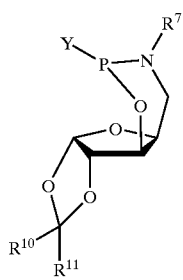

XVIIIb

Also provided in accordance with the invention are oligomeric compounds comprising a phosphite linkage having the Formula XXX:

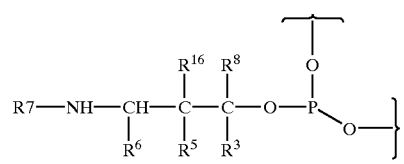

XXX

In some particularly preferred embodiments the azaphosphalane has the Formula XIVb:

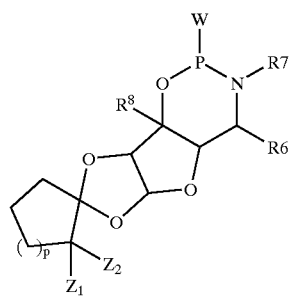

XIVb

In preferred embodiments of the invention, 75% of said phosphosphite linkage is in a single stereoisomeric form, with 85% being more preferred, and 95% being particualrly preferred. In especially preferred embodiments, the phosphosphite linkage is in a single stereoisomeric form, substantially free of other stereoisomeric forms.

DETAILED DESCRIPTION OF THE PREFERRED EMBODIMENTS

Especially preferred embodiments the azaphospholane has the Formula XVb or XVIb:

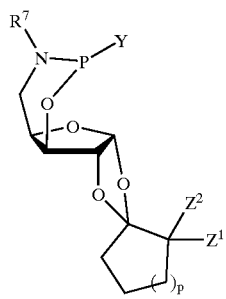

XVb

The present invention is directed to methods for the synthesis of phosphorothioate compounds having diastereomerically enriched phosphorothioate linkages, and to intermediates useful in their preparation.

In one aspect, the invention provides methods for the preparation of phosphorothioate linkages comprising the steps of reacting a first synthon of Formula I:

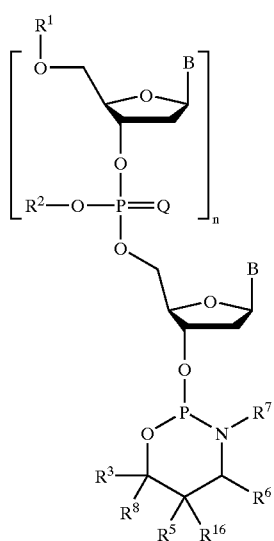

I wherein:

Q is independently O or S;

$R^1$ is a hydroxyl protecting group;

$R^2$ is a chiral auxiliary of formula —C($R^8$)$R^3$—C($R^{16}$) $R^5$—CH$R^6$—NH$R^7$;

$R^3$ is hydrogen, alkyl, cyanomethyl, monohalomethyl, dihalomethyl, trihalomethyl, —CH$_2$R$_4$, —CH$_2$Si(R4)$_3$, or —CH$_2$—SO$_k$R$^4$ where k is 0, 1 or 2;

$R^4$ is independently alkyl, aryl, aralkyl or alkaryl having up to 15 carbon atoms, —N(R$_{70}$)—C(=O)—R$_{71}$, —S—C(=O)—R$_{70}$, or —O—C(=O)—O—N(R$_{70}$)(R$_{71}$);

$R_{70}$ and $R_{71}$ are each independently alkyl, α-halo substituted alkyl, aralkyl, α-halo substituted aralkyl, or aryl substituted with up to three electronegative groups;

$R^5$ is H, —CN, —Si(R$^4$)$_3$, SO$_k$R$^4$ or halogen;

or $R^8$ and $R^{16}$ are each H, and $R^3$ and $R^5$, together, form one of the structures

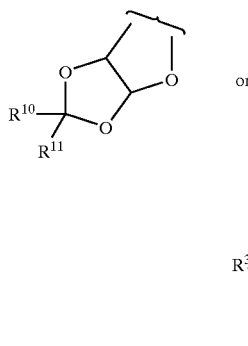

wherein:

$R^{10}$ and $R^{11}$ are H, alkyl having from 1 to about 10 carbons, —CH$_2$C(=O)OR$^{22}$, —CH$_2$CN, —CH$_2$Si(CH$_3$)$_3$, or o- or p-C$_6$H$_4$—R$^{21}$;

$R^{21}$ is hydrogen, —O—C(=O)CH$_3$, alkoxy having from 1 to about 10 carbons, —NO$_2$, or —N(R$^{22}$)$_2$;

$R^{22}$ is independently H or alkyl having from one to about 10 carbon atoms;

p is 1 or 2;

$Z^1$ and $Z^2$ are independently halogen, CN, —Si(CH$_3$)$_3$, and —C(=O)OR$^{22}$;

$R^{30}$ is hydrogen, —O—C(=O)CH$_3$, alkoxy having from 1 to about 10 carbons, or —O—Si(R$_4$)$_3$;

$R^6$ is H, alkyl or aralkyl having up to 15 carbon atoms;

or $R^5$ and $R^6$, together with the atoms to which they are attached, form a 5 or 6 membered ring;

$R^7$ is alkyl or aralkyl having up to 15 carbon atoms;

or $R^6$ and $R^7$, together, form one of the structures

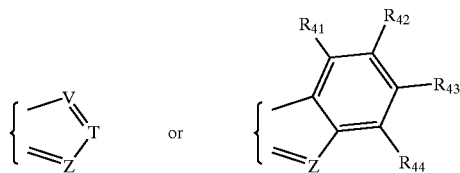

wherein

V, T, and Z are independently CH or N;

$R_{41}$, $R_{42}$, $R_{43}$, and $R_{44}$ are each independently H or an electronegative group;

$R^8$ is H or methyl;

$R^{16}$ is H, alkyl or aralkyl having up to 15 carbon atoms;

B is a nucleobase; and n is an integer from 0 to 50;

with a second synthon of Formula II:

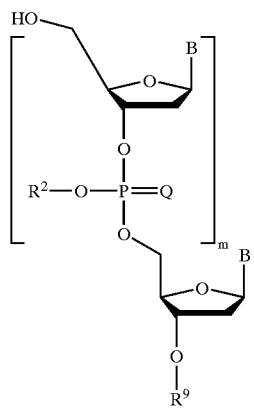

II wherein:

R⁹ is a hydroxyl protecting group or a linker connected to a solid support; and m is an integer from 0 to 50;

for a time and under reaction conditions effective to form a third synthon of Formula III:

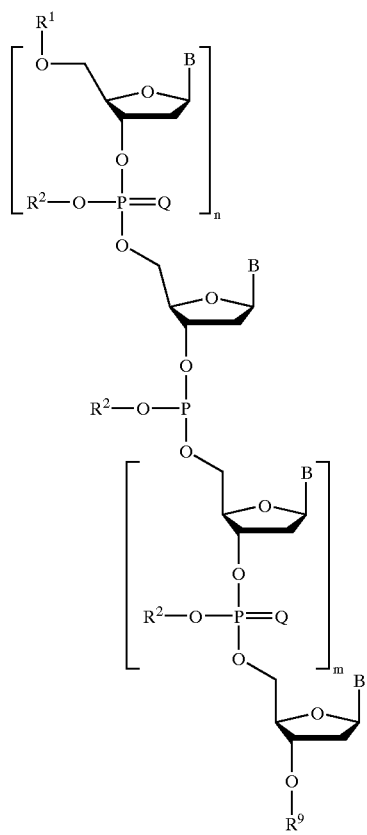

III and contacting said third synthon with a sulfurizing agent to form an oligomer of Formula IV:

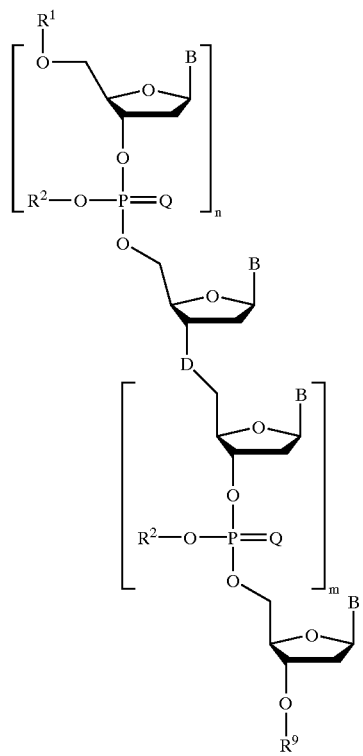

IV wherein D is said phosphorothioate linkage having the formula:

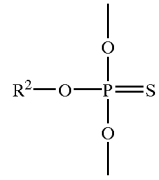

In accordance with the invention, first synthons are cyclic phosphoramidites having the general Formula VIc:

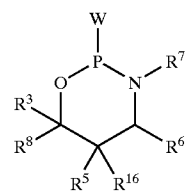

VIc in which W, $R^3$, $R^5$—$R^8$ and $R^{16}$ are as defined above.

The reaction of first and second synthons is conducted in the presence of a catalyst. The structures of the first synthon and the catalyst are chosen such that the opening of the cyclic O—P—N phosphoramidite (azaphospholane) ring proceeds by the stereoselective breaking of the intracyclic P—N bond of the azaphospholane, to yield a third synthon, which is diastereomerically enriched at phosphorus. Accordingly, in preferred embodiments of the methods of the invention, first synthons are diastereomerically enriched, and more preferably in a single stereochemical form, substantially free of other stereochemical forms. It is also advantageous for the first synthon and the catalyst to bear substituent groups which are of relatively large size (i.e., bulky groups) to aid in the proper orientation of reactants to achieve the desired stereoselectivity. As used herein, the term stereoselective has its normal meaning as a process in which one stereoisomer is produced or destroyed more rapidly than another, resuting in a predominance of the favored stereoisomer.

In preferred embodiments catalysts have one of the Formulas VIII or IX:

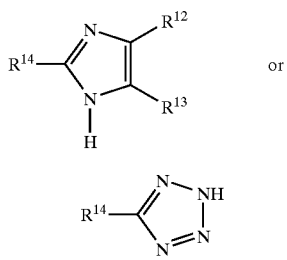

wherein $R^{12}$—$R^{14}$ are as defined above.

It has been found in accordance with the present invention that imidazole catalysts having electron-withdrawing substituents, in addition to substituents of relatively large size, are especially advantageous in production of stereochemically enriched products. While not wishing to be bound by a particular theory, it is believed that the catalyst first protonates the azaphospholane nitrogen, creating a good leaving group, which is displaced by the catalyst or its conjugate base. The imidazole or tetrazole attached to the phosphorus is then displaced either by the 3'-hydroxyl of the nucleosidic species, leading to a phosphite triester of high stereochemical purity, or by the catalyst, leading to epimerization.

It has been found in accordance with the present invention that catalysts which have appreciable acidity (i.e., which have pKa values of about 2 to 4) and which are relatively large can overcome the tendency toward epimerization at phosphorus, and result in stereoselective addition of the free 5'-hydroxyl of the nucleosidic species to be added. Thus, preferred substituents for groups $R^{13}$, $R^{14}$ and $R^{15}$ are those which are electron withdrawing, (and which therefore increase acidity), and of a size sufficient to maintain stereoselectivity. It will be recognized, however, that it is not necessary that all three groups $R_6$, $R_7$ and $R_8$ be of great bulk, so long as the overall size of the catalyst is sufficient to afford the desired stereoselectivity. Thus preferred $R^{12}$ and $R^{13}$ groups are independently hydrogen, halogen, cyano, nitro, alkyl having from one to 10 carbons, substituted alkyl having from one to 10 carbons, an ester group, or $R^{12}$ and $R^{13}$, together with the carbon atoms to which they are attached, form a substituted or unsubstituted phenyl ring where said substituents are electron withdrawing. Preferred $R^{14}$ groups include hydrogen, halogen, cyano, nitro, thio, alkyl having from one to 10 carbons, substituted alkyl having from one to 10 carbons, norbornyl, substituted norbornyl, aryl, substituted aryl wherein said substituents are electron withdrawing, or has the formula:

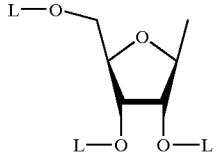

wherein L is protecting group. In prefered embodiments of the invention the catalyst is 2,4,5-tribromoimidazole, dibromocyanoimidazole, or dicyanobromoimidazole. In particularly preferred embodiments the catalyst is 4,5-dicyano-2-bromoimidazole.

It has been found in accordance with the present invetion that the dicyanoimidazole, bromoimidazole, and tribromoimidazole catalysts described in accordance with the present invention are useful as substitutes for tetrazole catalysts in standard solid phase oligonucleotide synthetic regimes. Such synthetic procedures are well known in the art, and are extensively described in the literature. See for example, Caruthers U.S. Pat. Nos. 4,415,732; 4,458,066; 4,500,707; 4,668,777; 4,973,679; and 5,132,418; and Koster U.S. Pat. No. 4,725,677 and U.S. Pat. No. Re. 34,069, and *Oligonucleotides and Analogues, A Practical Approach*, Eckstein, F., IRL Press, New York (1991). The use of the catalysts of the invention in these synthetic methlogies provides significant advantages over tetrazole catalysts, including, for example, significantly lower cost.

In other preferred embodiments $R^{14}$ has one of the formulas:

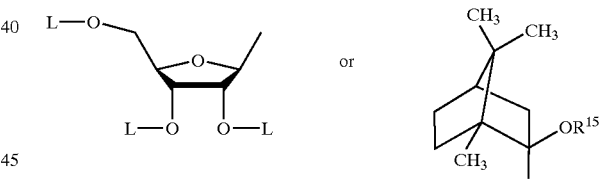

wherein $R^{15}$ is H, methyl, trimethylsilyl or acetyl.

In some preferred embodiments $R^6$ and $R^7$, together with the atoms to which they are attached, form an heterocyclic (i.e., imidazole, triazole or tetrazole) ring, which performs the function of the catalyst. Preferred first synthons which incorporate the catalyst therein have the general Formula Xa or XIIIa:

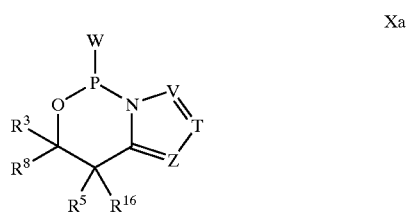

-continued

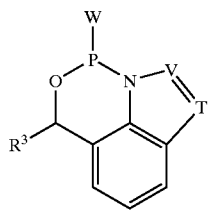

XIIIa

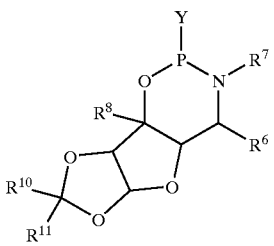

XIIa wherein V, T and Z are each independently N or CH. In especially preferred embodiments the first synthons incorporate imidazole rings, and have the Formula Xb or Xc:

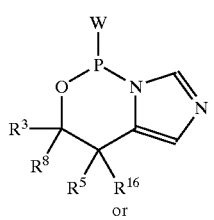

Xb or

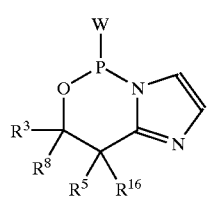

Xc

In further preferred embodiments of the invention the imidazole portions of the first synthons are further substituted, for example, by having a phenyl ring fused thereto, which preferably bears one or more electronegative groups. Thus in another preferred embodiment first synthons have the Formula XIa:

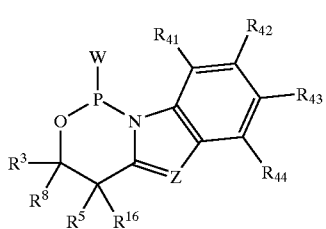

XIa

In further preferred embodiments, first synthons incorporate other relatively large substituent groups which facilitate the stereoselective opening of the azaphospholane ring. In particularly preferred embodiments first synthons have the Formula XIIa, and particularly Formula XVIIa or XVIIIa:

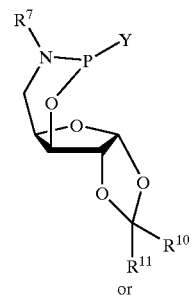

XVIIa or

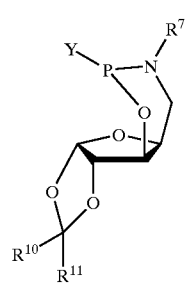

XVIIIa in which $R^{10}$ and $R^{11}$ are as defined above.

In especially preferred embodiments, first synthons have the Formula XVb or XVIb:

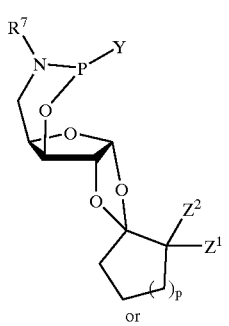

XVb or

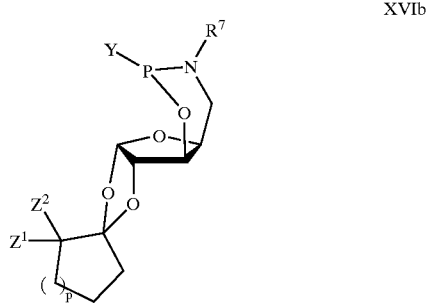

XVIb

In some preferred embodiments, the first synthon is obtained by reaction of a compound of Formula V:

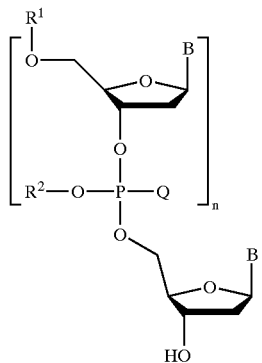

with an azaphospholane of Formula VIa:

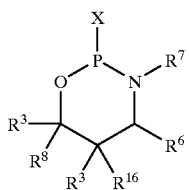

wherein $R^3$—$R^8$ are as defined above; and X is halogen, preferably chlorine, dialkylamino, imidazole or substituted phenoxy wherein said substituents are electron withdrawing, and preferably are halogen or nitro.

In more preferred embodiments the first synthon is obtained by reaction of a compound of Formula VII:

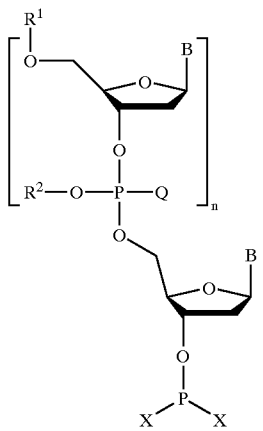

and a γ-amino alcohol of formula HO—C($R^8$)$R^3$—C($R^{16}$)$R^5$—CHR$^6$—NHR$^7$; wherein X and $R^1$—$R^{16}$ are as defined above.

$R_2$ is a chiral auxiliary, which has the formula —C($R^8$)$R^3$—C($R^{16}$)$R^5$—CHR$^6$—NHR$^7$, and which is formed as a consequence of the opening of the cyclic phosphite ring. The chiral auxiliary functions as a protecting group for the phosphorus linkage during the course of the synthesis of oligomeric phosphorothioates. Accordingly, chiral auxiliaries are allowed to remain on the growing chain, and are removed at the end of the iterative synthetic regime.

Removal of chiral auxiliaries can be conveniently accomplished in a single treatment after the completion of the iterative synthesis by treatment with either acidic reagents or by base catalyzed β-elimination. Suitable acidic reagents include α-halo organic acids such as, for example, 70% trifluoroacetic acid. Suitable reagents for removing chiral auxiliaries by β-elimination include ammonia and fluoride ion. Removal of chiral auxiliaries via β-elimination should be particularly advantageous where first synthons have the Formula XXa or Formula XIa, especially where at least one of $R_{41}$, $R_{42}$, $R_{43}$, and $R_{44}$ is an electronegative group, or where $R^3$ is —$CH_2R_4$, $R^4$ is independently —N($R_{70}$)—C(=O)—$R_{71}$, —S—C(=O)—$R_{70}$, or —O—C(=O)—O—N($R_{70}$)($R_{71}$).

After reacting first and second synthons to form a third synthon, the third synthon is sulfurized to form a phosphorothioate linkage having the formula:

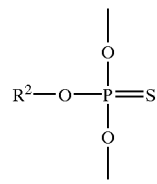

Sulfurization may be accomplished by any of the several sulfurizing agents known in the art to be suitable for conversion of phosphites into phosphorothioates. Useful sulfurizing agents include Beaucage reagent described in e.g., Iyer, R. P.; Egan, W.; Regan, J. B.; Beaucage, S. L., 3H-1,2-Benzodithiole-3-one 1,1-Dioxide as an Improved Sulfurizing Reagent in the Solid-Phase Synthesis of Oligodeoxyribonucleoside Phosphorothioates, *Journal of American Chemical Society*, 1990, 112, 1253–1254 and Iyer, R. P.; Phillips, L. R.; Egan, W.; Regan J. B.; Beaucage, S. L., The Automated Synthesis of Sulfur-Containing Oligodeoxyribonucleotides Using 3H-,2-Benzodithiol-3-one 1,1-Dioxide as a Sulfur-Transfer Reagent, *Journal of Organic Chemistry*, 1990, 55, 4693–4699. Tetraethyl-thiuram disulfide can also be used as described in Vu, H.; Hirschbein, B. L., Internucleotide Phosphite Sulfurization With Tetraethylthiuram Disulfide, Phosphorothioate Oligonucleotide Synthesis Via Phosphoramidite Chemistry, *Tetrahedron Letters*, 1991, 32, 3005–3007. Further useful reagents for this step are dibenzoyl Tetrasulfide, Rao, M. V.; Reese, C. B.; Zhengyun, Z., Dibenzoyl Tetrasulphide—A Rapid Sulphur Transfer Agent in the Synthesis of Phosphorthioate Analogues of Oligonucleotides, *Tetrahedron Letters*, 1992, 33, 4839–4842; di(phenylacetyl)disulfide, Kamer, R. C. R.; Roelen, H. C. P. F.; van den Eist, H.; van der Marel, G. A.; van Boom, J. H., An Efficient Approach Toward the Synthesis of Phosphorothioate Diesters Va the Schonberg Reaction, *Tetrahedron Letters*, 1989, 30, 6757–6760; sulfur; and sulfur in combination with ligands like triaryl, trialkyl or triaralkyl or trialkaryl phosphines.

The methods of the present invention can also be used to produce analogs of phosphorothioates, including phosphoroselenoates and phosphoroboronates. For example, phosphoroselenoates can be prepared by the methods of the invention by utilizing potassium selenocyanate in place of the sulfurizing agents described above. Phosphoroboronates can be prepared by similar adaptation of oxidizing agents known known in the art. See, for example, *Antisense Research and Applications,* Crooke, S. T., and Lebleu, B., Eds. CRC Press, Boca Raton, Fla. (1993).

$R_9$ and $R_1$ can each be a hydroxyl protecting group. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. The tert-butyldimethylsilyl (TBDMS) group is representative of protecting groups useful for protecting the hydroxyl functionality. A preferred protecting group for $R^1$ is the dimethoxytrityl group. Other representative groups may be found in Greene, T. W. and Wuts, P. G. M., *"Protective Groups in Organic Synthesis"* 2d. Ed., Wiley & Sons, 1991. Typically, protecting groups are removed at the end of the iterative synthesis.

$R_9$ may alternatively be a linker connected to a solid support. Solid supports are substrates which are capable of serving as the solid phase in solid phase synthetic methodologies, such as those described in Caruthers U.S. Pat. Nos. 4,415,732; 4,458,066; 4,500,707; 4,668,777; 4,973,679; and 5,132,418; and Koster U.S. Pat. No. 4,725,677 and Re. 34,069. Linkers are known in the art as short molecules which serve to connect a solid support to functional groups (e.g., hydroxyl groups) of initial synthon molecules in solid phase synthetic techniques. Suitable linkers are disclosed in *Oligonucleotides And Analogues A Pratical Approach,* Ekstein, F. Ed., IRL Press, N.Y, 1991.

Alkyl groups according to the invention include straight chain, branched, and cyclic carbon and hydrogen containing groups such as methyl, isopropyl, and cyclohexyl groups. Preferred alkyl groups have 1 to about 6 carbon atoms.

Aralkyl groups according to the invention include both alkyl and aryl portions, although the point of attachment of such groups is through an alkyl portion thereof. Benzyl groups provide one example of an aralkyl group. Alkaryl groups include both alkyl and aryl portions, and are attached through their aryl portions. The term aryl is intended to denote monocyclic and polycyclic aromatic groups including, for example, phenyl, naphthyl, xylyl, pyrrole, and furyl groups. Although aryl groups (e.g., imidazo groups) can include as few as 3 carbon atoms, preferred aryl groups have 6 to about 14 carbon atoms, more preferably 6 to about 10 carbon atoms. The alkyl, alkaryl, and aryl groups may be substituted (e.g., i.e, bear halogens and hydroxy groups) or unsubstituted moieties. In some prefered embodiments the alkyl or aralkyl groups bear electron withdrawing substituents, preferably halogen atoms, in one their α-carbons. Examples of α-halo substituted alkyl groups include mono-, di-, and trihalo methyl groups. Examples of α-halo substituted aralkyl groups include α-halo benzyl groups.

Certain substituent groups of compounds of the invention bear electron withdrawing groups. As used herein, the term "electron wihdrawing" has its normal meaning as a chemical functionality which electronically or inductively causes the withdrawal of electron density form the moiety to which the electron withdrawing groups is attached. Representative electron withdrawing groups include nitro groups, halogens, cyano, carboxyl groups and substituted carboxy groups such as ester groups and amido groups. Other electron withdrawing groups will be apparent to those of skill in the art, once armed with the present disclosure.

Substituent B is a nucleobase. The term nucleobase as used herein is intended to include naturally occurring nucleobases (i.e., heterocyclic bases found in naturally occurring nucleic acids) and their non-naturally occurring analogs. Thus, nucleobases according to the invention include naturally occurring bases adenine (A), guanine (G), thymine (T), cytosine (C) and uracil (U), both in their unprotected state and bearing protecting or masking groups. Examples of nucleobase analogs include $N^4,N^4$-ethanocytosine, 7-deazaxanthosine, 7-deazaguanosine, 8-oxo-$N^6$-methyladenine, 4-acetylcytosine, 5-(carboxyhydroxymethyl)uracil, 5-fluorouracil, 5-bromouracil, 5-carboxymethylaminomethyl-2-thiouracil, 5-carboxymethylaminomethyl uracil, inosine, $N^6$-isopentyladenine, 1-methyladenine, 2-methylguanine, 5-methylcytosine, $N^6$-methyladenine, 7-methylguanine, 5-methylaminomethyl uracil, 5-methoxyaminomethyl-2-thiouracil, 5-methoxyuracil, pseudouracil, 5-methyl-2-thiouracil, 2-thiouracil, 4-thiouracil, 5-(1-propynyl)-4-thiouracil, 5-(1-propynyl)-2-thiouracil, 5-(1-propynyl)-2-thiocytosine, 2-thiocytosine, and 2,6-diaminopurine. Other suitable base analogs, for example the pyrimidine analogs 6-azacytosine, 6-azathymidine and 5-trifluoromethyluracil, may be found in Cook, D. P., et al., International Publication No. 92/02258, which is herein incorporated by reference.

The compounds of the invention are preferably up to 50 nucleobases in length, with 10 to 30 nucleobases being more preferred, and 15 to 25 nucleobases being especially preferred.

In preferred embodiments the phosphorothioate linkage produced by the method of the invention is diastereomerically enriched. The term "diastereomerically enriched" denotes the predominance of one stereochemical form over the other. In preferred embodiments the phosphorothioate linkage is 75% in a single stereochemical form. In further preferred embodiments the phosphorothioate linkage is 85% in a single stereochemical form, with 90% being further preferred and 95% being especially preferred. In further preferred embodiments the phosphorothioate linkage is in a single stereochemical form, substantially free of other stereochemical forms.

Preferably, following sulfurization, the phosphorothioate is next converted to a new first synthon. This is first accomplished by the removal of the 5'-hydroxyl protecting group $R_1$, under conditions which will necessarily depend upon the chemical identity of the specific $R_1$ group. After removal of the protecting group, the unprotected 5'-alcohol may be employed as a new second synthon in the iterative method. Libraries of dimeric and higher synthons may be prepared and stored to facilitate the iterative synthesis of desired nucleobase sequences.

Also provided according to the invention are azaphospholanes of Formula VIb:

VIb

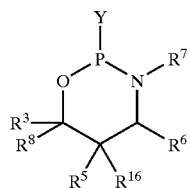

wherein Y is X or W, wherein X is halogen, dialkylamino, imidazole, or substituted phenoxy wherein said substituents are electron withdrawing, and W has the formula:

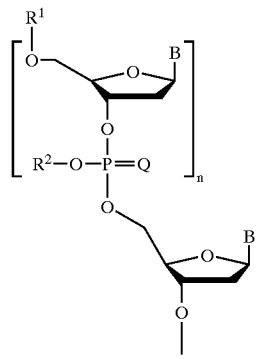

wherein constituent members are as defined above. Preferably, the azaphospholanes of Formula VIb are diastereomerically enriched. In particular, it is advantageous to have defined stereochemistry around phosphorus atom, to afford diastereomerically enriched products upon stereoselective opening of the azaphospholane ring.

In preferred embodiments, compounds of the invention have one of the Formulas Xb, XIb, XIIb, XIIIb or XXb:

Xb

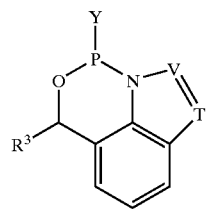

XIb

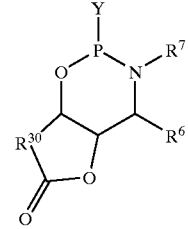

XIIb

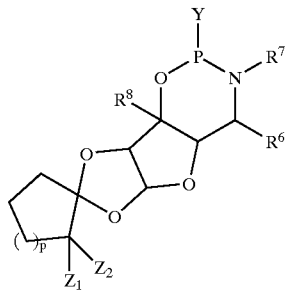

XIIIb

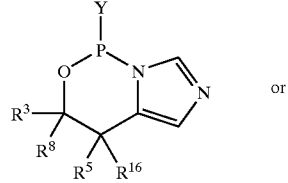

XXb

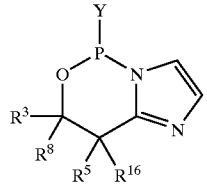

wherein $R^3$—$R^{16}$, Y, V, T, Z, $Z_1$, $Z_2$ and p are as defined above.

Paticularly preferred embodiments of the compounds of the invention have the Formula XIVb, Xd, Xe, XVIIb, XVIIIb, XVb or XVIb:

XIVb

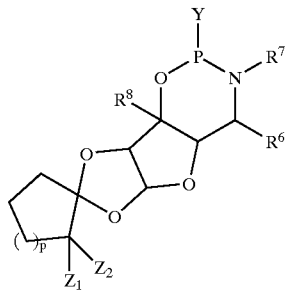

Xd

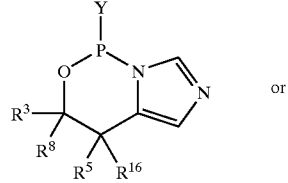

or

Xe

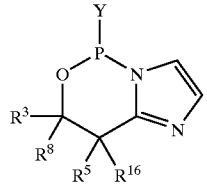

XVb

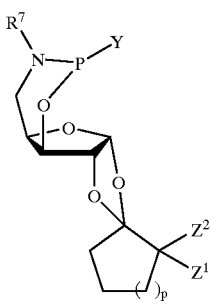

or

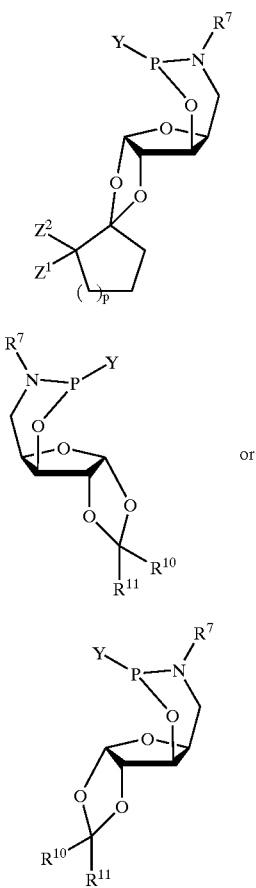

As used herein, the term "contacting" means directly or indirectly causing placement together of moieties to be contacted, such that the moieties come into physical contact with each other. Contacting thus includes physical acts such as placing the moieties together in a container. The term "reacting" as used herein means directly or indirectly causing placement together of moieties to be reacted, such that the moieties chemically combine or transform.

The method of the invention is performed in the presence of a solvent, for example chloroform or acetonitrile. Other solvents suitable for use in the present method will be readily apparent to those skilled in the art, once having been made aware of the present disclosure.

In general, it is preferred that the molar ratio of the catalyst to the first synthon starting material be from about 1 to about 50; preferably from about 2.5 to about 10.

The method of the present invention can be carried out in any suitable vessel which provides efficient contacting between the first and second synthons, and the catalyst. The reaction vessel used should be resistant to the components of the reaction mixture. Glass-lined vessels would be suitable for this purpose. Additional vessel materials will be apparent to those skilled in the art.

The reagents of the present method may be added in any order. The method is preferably carried out under an inert atmosphere, any should be carried out in a dry atmosphere. Any suitable inert gas may be employed, such as nitrogen, helium and argon.

Preferably, the method is carried out at temperatures ranging between about −20° C. and about 40° C., with temperatures ranging from about −15° C. to about 0° C. being more preferred.

Reaction time is generally from about one minute to about two hours, with reaction times of from about one minute to about 10 minutes being preferred.

Product can be recovered by any of several methods known to those of skill in the art. Preferably, products are recovered by chromatography. Additional separation of isomers can be accomplished by techniques known in the art including high performance liquid chromatography.

When $R^9$ is a solid support, purification is carried out after removal of the oligonucleotide from the solid support using methods known in the art.

The invention is further illustrated by way of the following examples. These examples are illustrative only and are not intended to limit the scope of the appended claims.

EXAMPLES

General Methods

Melting points (m.p.) were determined using an Electrothermal MP apparatus and are uncorrected. Optical rotation measurements were carried out in the indicated solvents employing a Jasco DIP-140 digital polarimeter. Mass spectra (CI or EI) were obtained on an HP 5980A quadrupole mass spectrometer in the direct-inlet mode.

NMR spectra were recorded on JEOL270, Varian XL200, XL300, or Unity 500 spectrometers. Chemical shifts are given in the δ scale in parts per million. The assignments of proton spectra are based on COSY experiments. The residual proton signals of deuteriochloroform (δ7.24 ppm), methanol (δ3.30 ppm) and acetonitrile (δ1.93 ppm) were used as reference in these solvents. The multiplicities are recorded using the following abbreviations: s, singlet; d, doublet; t, triplet; q, quartet; m, multiplet. $^{31}P$ NMR spectra were obtained on either a Varian XL200, XL300 or Unity 500 instrument, and chemical shifts are given with respect of aqueous phosphoric acid. Peak assignments of $^{13}C$-NMR spectra were, in some cases, made with the aid of APT, HMQC or HETCOR experiments. $^{31}P$-NMR spectra were recorded on Jeol CFP 270 and Varian UNITY 500 at 68.7 MHz, 125.7 MHz using a 85% $H_3PO_4$ as external standard.

Fast atom bombardment (FAB-MS) were obtained on an KRATOS MS 25RFA spectrometer in the direct-inlet mode. High resolution FAB mass spectra of key compounds were obtained on a ZAB 2F HS spectrometer in the direct inlet mode (Biomedical Spectrometry Unit).

Tetrahydrofuran (THF) was distilled from sodium benzophenone ketyl. Dichloromethane was distilled from $P_2O_5$. Triethylamine and acetonitrile were distilled from $CaH_2$. N,N-Dimethyl formamide was dried by shaking with KOH, followed by distillation. Thin-layer chromatography (TLC) was performed using Kieselgel 60 $F_{254}$ aluminium-backed plates (0.2 mm thickness) and visualized by UV and/or dipping in a solution of ammonium molybdate (2.5 g) and ceric sulfate (1 g) in 10% v/v aqueous sulphuric acid (100 ml), followed by heating. Kieselgel 60 (Merck 230–400 mesh) silica gel was employed for column chromatography.

Example 1

3R-hydroxy-N-iso-propylbutanoamide (10)

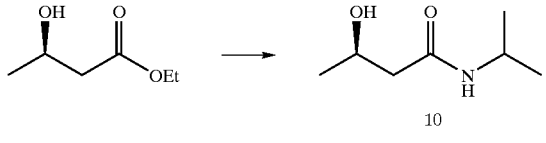

A 2 M solution of trimethylaluminium in hexane (50 ml, 100 mmol) was slowly added to a solution of 8.5 ml (100 mmol) isopropylamine in 100 ml dichloromethane under nitrogen at room temperature. The mixture was stirred for 30 min and then cooled to 0° C. before 6.6 g (50 mmol) of ethyl-3R-hydroxybutanoate was added. The reaction mixture was stirred at room temperature for 2 hours for completion, carefully quenched with dilute HCl and extracted with chloroform. The organic extract was dried over $MgSO_4$ and concentrated to afford 7 g N-isopropyl 3R-hydroxy butanoamide. After recrystallization, 5.5 g pure amide 10 was obtained (yield 76%).: m.p. 62° C.; $^1$H NMR (200 MHz, $CDCl_3$) δ6.41 (m, 1H, NH), 4.35 (b, 1H, OH), 3.78–4.15 (m, 2H, MeCH, $Me_2CH$), 2.08–2.32 (m, 2H, $CH_2$), 1.12 (d, J=6.3 Hz, 3H, Me), 1.07 (d, J=6.6 Hz, 6H, $NCHMe_2$); $^{13}$C NMR (50 MHz, $CDCl_3$) δ171.5 (C=O), 64.7 (CHOH), 43.8 (NHCH), 41.0 ($CH_2$), 22.7 (Me), 22.4 ($NCHMe_2$); MS(EI) m/e 145 ([M$^+$], 25%), 130 (27), 112 (4), 101 (6), 86 (34), 69 (8), 58 (22), 44 (100); HRMS(EI) m/e calc'd for $C_7H_{15}O_2N$ [M$^+$]: 145.1103, found 145.1109.

Example 2

2R-Hydroxy-4-(N-isopropyl)aminobutane (11)

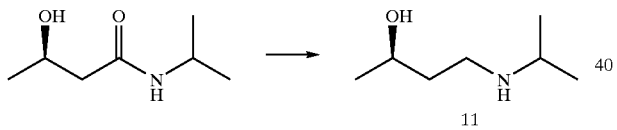

To a solution of 32 ml 1 M borane (32 mmol) in THF was added 2.32 g (16 mmol) 3R-hydroxy-N-iso-propyl-butyl butanoamide 10 in 20 ml THF at 0° C. under nitrogen. The solution was then brought to reflux and maintaned there for one hour. The reaction mixture was cooled to room temperature and 1 N HCl was added slowly to quench the reaction. THF was removed in vacuo, and the aqueous solution was saturated with solid NaOH and then was extracted three times with a total 300 ml chloroform. The combined chloroform phase was dried, filtered and distilled to afford 1.4 g 3-(N-isopropylamino)butan-2-ol 11 as a clear, colorless liquid (yield 67%).: $^1$H NMR (200 MHz, $CDCl_3$) δ3.80–3.96 (m, 1H, CHOH), 2.86–2.98 (m, 1H, MeCH), 2.56–2.75 (m, 2H, $NCH_2$), 1.24–1.60 (m, 2H, $CH_2$), 1.08 (d, J=6.1 Hz, 3H, Me), 0.98 (d, J=6.2 Hz, 6H, $Me_2$); $^{13}$C NMR (200 MHz, $CDCl_3$) δ69.5 (OCH), 48.6 ($NHCH_2$), 46.0 (NHCH), 37.2 ($CH_2$), 23.5, 22.9, 22.5; MS(EI) m/e 131 ([M$^+$], 10%), 116 (81), 98 (35), 72 (100), 58 (30), 56 (45), 44 (37); HRMS(EI) m/e calc'd for $C_7H_{17}ON$ [M$^+$]: 131.1310, found 131.1311; $[\alpha]_D^{20}$=32.5° (c=0.21, chloroform).

Example 3

2R-Hydroxy-4-(N-tert-butyl)aminobutane (31)

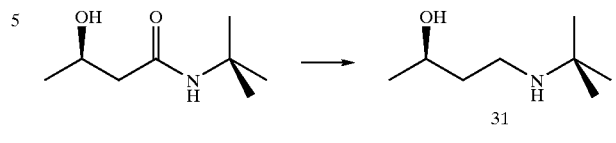

To a solution of 26.4 ml 1 M (26.4 mmol) borane in THF was added 2.1 g (13.2 mmol) 3R-hydroxy-N-tert-butylbutanoamide in 20 ml THF at 0° C. under nitrogen. The solution was then brought to reflux and maintained there for one hour. The reaction mixture was cooled down to room temperature and 1 N HCl was added slowly to quench the reaction. THF was removed in vacuo, and the aqueous solution was saturated with solid NaOH and then was extracted three times with a total 250 ml diethyl ether. The combined organic phase was dried, filtered and distilled to afford 398 mg 2R-hydroxy-4-(N-tert-butyl)aminobutane 31 as a clear, colorless liquid (yield 20.1%).: $^1$H NMR (200 MHz, $CDCl_3$) δ3.80–3.92 (m, 1H, CHOH), 3.40–3.80 (b, 2H, OH, NH), 2.50–2.90 (m, 2H, $NCH_2$), 1.28–1.61 (m, 2H, $CH_2$), 1.07 (d, 3H, Me), 1.03 (s, 9H, $Me_3$)

Example 4

5'-O-(tert-butyldimethylsilyl)thymidine (1)

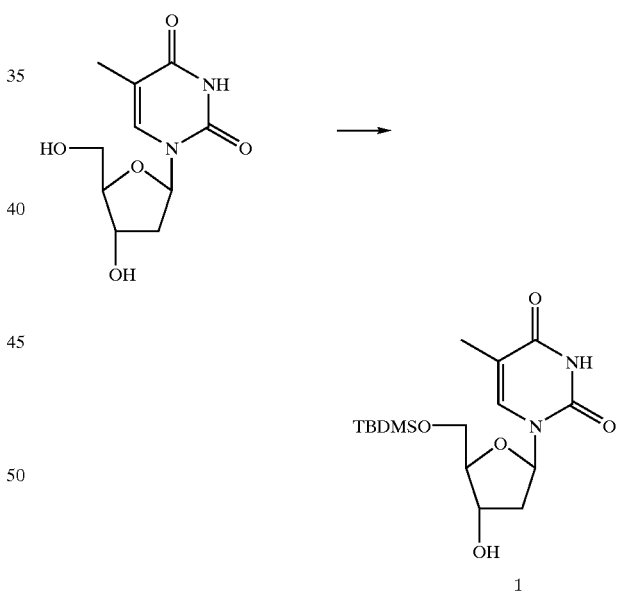

To a solution of 2.42 g (10 mmol) thymidine in 15 ml DMF was added 1.7 g (25 mmol) imidazole and 1.6 g (10.6 mmol) tert-butyldimethyl silyl chloride. The solution was stirred at room temperature for 3 hours. DMF was then removed in vacuo and the residue was dissolved in 150 ml of ethyl acetate. The solution was washed with water and the organic layer was dried over $MgSO_4$. After removing the solvent, the solid was recrystallized with ethyl acetate/pentane to obtain 2.5 g pure 5'-O-(tert-butyldimethylsilyl) thymidine 1 (70% yield).: m.p. 193–194° C.; $^1$H NMR (500

MHz, CDCl$_3$) δ9.0 (s, 1H, NH), 7.50 (s, 1H, H-6), 6.36 (dd, J=5.8, 8.1 Hz, 1H, H-1'), 4.44 (m, 1H, H-3'), 4.03 (m, 1H, H-4'), 3.85 (m, 2H, H-5'), 2.66 (d, J=3.8 Hz, 1H, OH), 2.35 (m, 1H, H-2'), 2.07 (m, 1H, H-2'), 1.89 (s, 3H, C=CMe), 0.89 (s, 9H, CMe$_3$), 0.09 (s, 6H, SiMe$_2$); $^{13}$C NMR (125 MHz, CDCl$_3$) δ163.8 (C-4), 150.4 (C-2), 135.4 (C-6), 110.9 (C-5), 87.2 (C-4'), 85.0 (C-1'), 72.6 (C-3'), 63.6 (C-5'), 41.1 (C-2'), 25.9 (SiCMe$_3$), 18.3 (SiCMe$_3$), 12.5 (C=CMe), −5.4 (SiMe$_2$), −5.5 (SiMe$_2$).

Example 5

5'-O-(4,4'-dimethoxytrityl)thymidine (16)

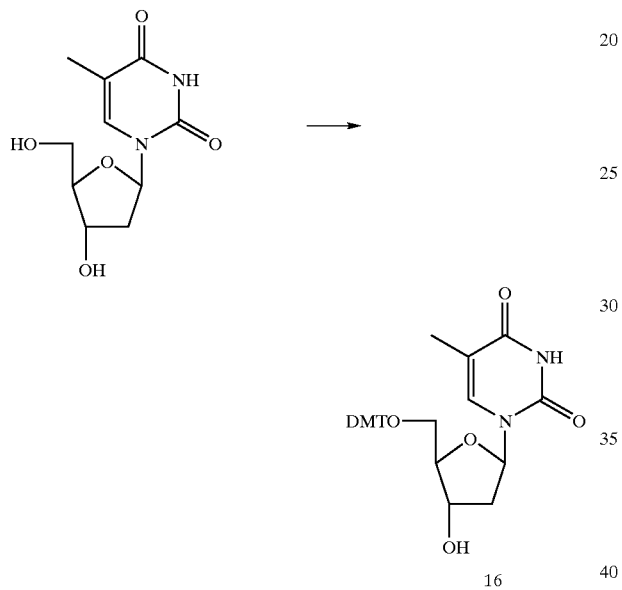

Triethylamine (10 ml) in 200 ml THF was injected into a solid mixture of 6.8 g (28.0 mmol) thymidine and 10.2 g (28.6 mmol) 4,4'-dimethoxytrityl chloride under nitrogen with stirring. The solution was stirred at room temperature for 2 hours. After completion of the reaction, 10 ml methanol was added to consume the excess DMTrCl. The mixture was stirred for 5 minutes and the solvent removed by rotary evaporation. The residue was dissolved in 250 ml of ethyl acetate and the solution was washed with saturated NaHCO$_3$ and dried over MgSO$_4$. The solid was recrystallized from ethyl acetate/hexane to obtain 13.0 g 5'-protected thymidine 16 (85.6%).: m.p. 124–126° C.; $^1$H NMR (200 MHz, CDCl$_3$) δ8.97 (s, 1H, NH), 7.60 (m, 1H, H-6), 6.72–7.42 (m, 13H, Ph), 6.42 (m, 1H, H-1'), 4.56 (m, 1H, H-3'), 4.05 (m, 1H, H-4'), 3.78 (s, 6H, OMe$_2$), 3.41 (m, 2H, H-5'), 2.62 (m, 1H, OH), 2.46 (m, 2H, H-2'), 1.46 (s, 3H, Me); $^{13}$C NMR (50 MHz, CDCl$_3$) δ163.0 (C-4), 157.6, 149.8 (C-2), 143.5, 135.0 (C-6), 134.7, 134.6, 129.4, 127.4, 127.3, 126.5, 112.8, 110.9 (C-5), 86.7 (C-4'), 86.2, 84.7 (C-1'), 72.5 (C-3'), 63.8 (C-5'), 55.5 (OCH$_3$), 41.3 (C-2'), 12.5 (CH$_3$).

Example 6

5'-O-(4,4'-dimethoxytrityl)-3'-O-(tert-butyldimethlsilyl)thymidine (17)

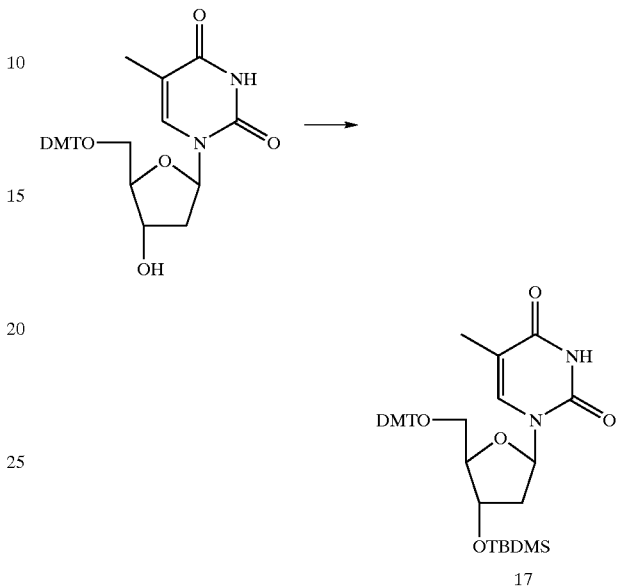

To a solution of 13.0 g (23.9 mmol) 5'-O-(4,4'-dimethoxytrityl)thymidine 16 in 50 ml DMF was added 3.0 g (44 mmol) imidazole and 3.6 g (23.9 mmol) tert-butyl-dimethylsilyl chloride. The solution was stirred at room temperature for 3 hours. DMF was then removed in vacuo and the residue was dissolved in 300 ml of ethyl acetate. The solution was washed with water and the organic layer was dried over MgSO$_4$. After concentration of the solution and recrystallization from ethyl acetate/hexane, the solid product 5'-O-(4,4'-dimethoxy)-3'-(tert-butyldimethylsilyl)thymidine 17 was used directely for the next reaction.

Example 7

3'-O-(tert-butyldimethylsilyl)thymidine (18)

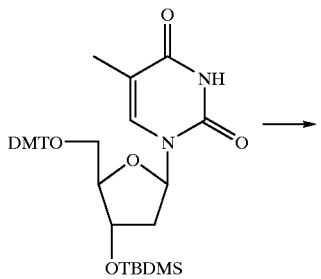

Example 9

Phosphoramidite (13a)

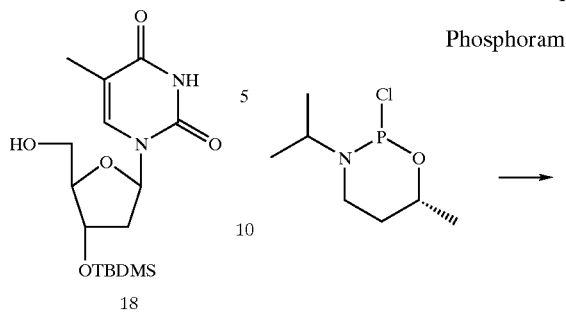

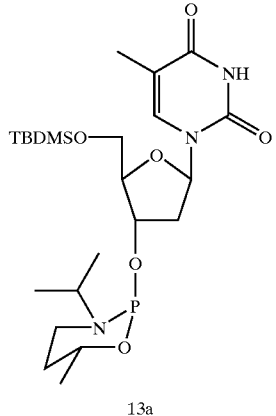

A solution of 5 g (7.6 mmol) 5'-O-(4,4'-dimethoxytrityl)-3'-O-(tert-butyldimethylsilyl)thymidine 17 in 100 ml 80% aq. acetic acid was stirred until the removal of dimethoxytrityl group was completed. Saturated Na$_2$CO$_3$ was then added to adjust the pH of the solution to 6–7. The solution was then extracted with ethyl acetate. The extract was dried and the mixture was chromatographed on a silica gel column (CH$_2$Cl$_2$:MeOH=20:1) to give 2.5 g of 3'-O-(tert-butyldimethylsilyl)thymidine 18 (92.6%).: m.p.93–95° C. (lit. 83–84° C.); H NMR (200 MHz, CDCl$_3$) δ9.18 (s, 1H, NH), 7.36 (b, 1H, H-6), 6.12 (t, J=6.8 Hz, 1H, H-1'), 4.44–4.48 (m, 1H, H-3'), 3.69–3.91 (m, 3H, H-4', H-5'), 2.87 (m, 1H, OH), 2.15–2.35 (m, 2H, H-2'), 1.87 (S, 3H, C=CMe), 0.86 (s, 9H, CMe$_3$), 0.05 (s, 6H, SiMe$_2$); $^{13}$C NMR (125 MHz, CDCl$_3$) δ163.9 (C-4), 150.4 (C-2), 137.1 (C-6), 110.9 (C-5), 87.6 (C-4'), 86.8 (C-1'), 71.5 (C-3'), 61.9 (C-5'), 40.4 (C-2'), 25.7 (SiCMe$_3$), 17.9 (SiCMe), 12.5 (C=CMe), −4.7 (SiMe$_2$), −4.9 (SiMe$_2$).

Example 8

2-Chloro-3-iso-propyl-6R-methyl-1-oxa-3-aza-2-phosphacyclohexane (12)

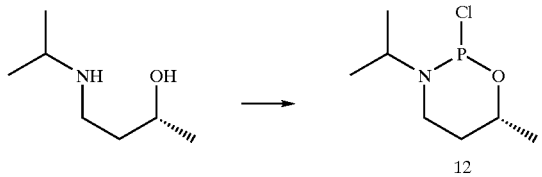

To a solution of 2.2 ml (3.45 g, 25 mmol) phosphorus trichloride in 30 ml dichloromethane was added a solution of 2.89 g (22 mmol) 2R-hydroxy-4-(N-iso-propyl)aminobutane 11 and 5.0 g (6.9 ml, 50 mmol) triethylamine in 20 ml dichloromethane with vigorous stirring under nitrogen at 0° C. Stirring was continued at room temperature for 0.5 hour. The solvent was removed by evaporation under reduced pressure and the residue was extracted with diethyl ether (3×50 ml). Distillation gave 2.9 g of product 12 (74.4% yield).: $^1$H NMR (200 MHz, CDCl$_3$) δ4.48–4.68 (m,.1H, OCH), 3.40–3.61 (m, 1H, NCH), 3.15–3.38 (m, 1H, NCH$_2$), 2.80–2.96 (m, 1H, NCH$_2$), 1.71–1.85 (m, 2H, CH$_2$), 1.25 (d, J=6.4 Hz, 3H, Me), 1.13 (dd, 6H, Me$_2$); $^{13}$C NMR (50 MHz, CDCl$_3$) δ69.5 (d, J=4.3 Hz, OCMe), 49.6 (d, J=34 Hz, NCMe$_2$), 37.4 (d, J=5.5 Hz, NCH$_2$), 33.4 (CH$_2$), 22.2 (d, J=4.3 Hz, Me), 21.1 (d, J=13.3 Hz, Me$_2$), 19.2 (d, J=5.0 Hz, Me$_2$); $^{31}$P NMR (81 MHz,CDCl$_3$) δ160.6.

To a solution of 215 mg (1.1 mmol) of 2-chloro-3-isopropyl-6R-methyl-1-oxa-3-aza-2-phosphacyclohexane 12 in 40 ml CH$_2$Cl$_2$ was added a solution of 356 mg (1.0 mmol) of 5-O-(tert-butyldimethylsilyl)thymidine and 0.154 ml triethylamine (111 mg, 1.1 mmol) in 20 ml CH$_2$Cl$_2$ with vigorous stirring under nitrogen at 0° C. The mixture was stirred at room temperature until TLC indicated that the reaction had gone to completion. The reaction mixture was transferred to 150 ml ethyl acetate, which was previously washed with a saturated NaHCO$_3$ solution. Saturated NaHCO$_3$ was then added to wash the solution. The separated organic phase was dried over MgSO$_4$. A white foam (quantitative yield) was formed after the solvent was removed by evaporation under reduced pressure. Two components were found from $^{31}$P NMR spectra in a ratio of 1:3 (135.0 ppm:133.6 ppm). The reaction mixture in CDCl$_3$ was then refluxed for about 4 hours to get a ratio of up to 1:12 (135.0 ppm:133.6 ppm). After chromatography on a silica gel column (hexane:ethyl acetate:triethylamine=5:3:2), the fast eluting component (133.6 ppm) was separated as a pure diastereomer.: $^1$H NMR (500 MHz, CDCl$_3$) δ7.50 (m, 1H, H-6), 6.36 (dd, J=8.5, 5.8 Hz, 1H, H-1'), 4.56 (m, 1H, H-3'), 4.30 (m, 1H, HCMe), 4.04 (m, 1H, H-4'), 3.75–3.90 (m, 2H, H-5'), 3.39 (hept, J=6.3 Hz, 1H, NCH), 3.24 (m, 1H, NCH$_2$), 2.72 (m, 1H, NCH$_2$), 2.35 (m, 1H, H-2'), 2.06 (m, 1H, H-2'), 1.89 (d, J=0.9 Hz, 3H, CH$_3$), 1.64 (m, 2H, CH$_2$), 1.16 (d, J=6.4 Hz, 3H, OCHMe), 1.08 (dd, J=2.0 Hz, 6.3Hz, 6H, NCMe$_2$), 0.89 (s, 9H, SiCMe$_3$), 0.09 (d, J=1.5 Hz, 6H, SiMe$_2$); $^{13}$C NMR (125 MHz, CDCl$_3$) δ163.9 (C-4), 150.5 (C-2), 135.3 (C-6), 110.9 (C-5), 86.5 (d, J=2.8 Hz, C-4'), 84.8 (C-1'), 73.3 (d, J=19.2 Hz, C-3'), 66.0 (d, J=2.7 Hz, OCH), 63.2 (C-5'), 49.2 (d, J=34.8 Hz, NCH), 40.4 (d, J=4.6 Hz, C-2'), 36.6 (d, J=5.5 Hz, NCH$_2$), 34.6 (CH$_2$), 25.9 (SiCMe$_3$), 22.9 (d, J=4.6 Hz, OCMe), 21.8 (d, J=10 Hz, NCMe$_2$), 21.0 (d, J=4.6 Hz, NCMe$_2$), 18.3 (SiCMe$_3$), 12.5 (C=CMe), −5.5 (SiMe$_2$), −5.4 (SiMe$_2$); $^{31}$P NMR (81 MHz, CDCl$_3$) δ133.6; MS (CI, NH$_3$)) m/e 516 ([M+H$^+$],37%), 390 (21), 339 (92), 178 (100), 160 (55); HRMS (CI, NH$_3$) m/e calc'd for C$_{23}$H$_{43}$N$_3$O$_6$PSi [M+H$^+$]: 516.2659, found 516.2664

Example 10

Phosphoramidite (13b)

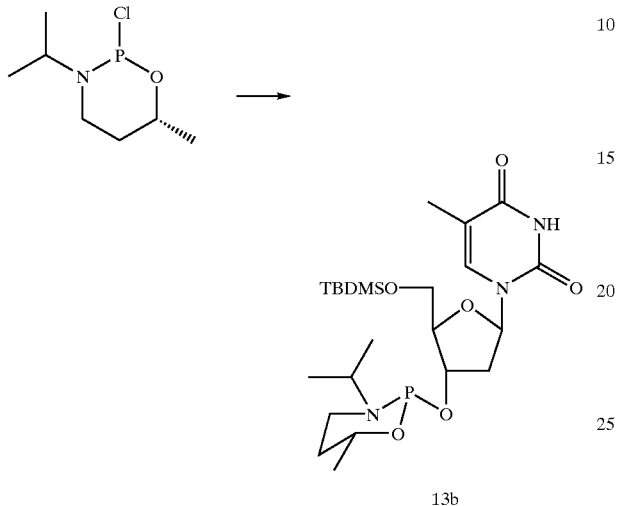

13b

To a solution of 215 mg (1.1 mmol) 2-chloro-3-isopropyl-6R-methyl-l-oxa-3-aza-2-phosph ocyclohexane 12 in 40 ml CH$_2$Cl$_2$ was slowly added a solution of 356 mg (1.0 mmol) 5'-O-(tert-butyldimethylsilyl)thymidine 1 and 0.154 ml triethylamine (111 mg, 1.1 mmol) in 20 ml CH$_2$Cl$_2$ with vigorous stirring under nitrogen at −78° C. The mixture was stirred at −78° C. until TLC indicated that the reaction had gone to completion. The reaction mixture was quickly transferred to 150 ml ethyl acetate, which was previously washed with a cold saturated NaHCO$_3$ solution. Cold saturated NaHCO$_3$ was then added to wash the solution. The separated organic phase was dried over MgSO$_4$. A white foam (quantitative yield) was formed after the solvent was removed by evaporation under reduced pressure at 0° C. Two components were found from $^{31}$P NMR spectra in a ratio of 5:1 (135.1 ppm:133.6 ppm). The reaction mixture in CDCl$_3$ was immediately chromatographed on a silica gel column (hexane:ethylacetate:triethylamine=5:3:2) and the slow eluting component (135.1 ppm) was separated as an enriched diastereomer (92% pure).: $^1$H NMR (500 MHz, CDCl$_3$) δ7.48 (m, 1H, H-6), 6.32–6.35 (dd, J=5.4, 7.8 Hz, 1H, H-1'), 4.55–4.60 (m, 1H, H-3'), 4.02–4.10 (m, 1H, OCH), 4.00 (m, 1H, H-4'), 3.74–3.89 (m, 2H, H-5'), 3.36–3.45 (m, 1H, NCH), 3.09–3.14 (m, 1H, NCH$_2$), 2.85–2.93 (m, 1H, NCH$_2$), 2.40–2.44 (m, 1H, H-2'), 2.12–2.21 (m, 1H, CH$_2$), 2.00–2.06 (m, 1H, H-2'), 1.88 (s, 3H, C=CCH$_3$), 1.81–1.86 (m, 1H, CH$_2$), 1.28 (d, J=6.3 Hz, 3H, OCMe), 1.11 (dd,J=6.3, 11.7 Hz, 6H, NCMe$_2$), 0.89 (s, 9H, Me$_3$), 0.08 (d, J=2.0 Hz, 6H, SiMe$_2$); $^{13}$C NMR (125 MHz, CDCl$_3$) 6 163.7 (C-4), 150.2 (C-2), 135.5 (C-6), 110.8 (C-5), 87.0 (d, J=6.4 Hz, C-4'), 84.8 (d, J=5.5 Hz, C-1'), 72.8 (d, J=19.2 Hz, OCHMe), 70.3 (d, 7.3, C-3'), 63.1 (C-5'), 49.5 (d, J=39.4 Hz, NCHMe$_2$), 40.1 (d, J=1.8 Hz, C-2'), 36.9 (d, J=5.5 Hz, NCH$_2$), 31.5 (d, J=7.3 Hz, CH$_2$), 25.9 (SiCMe$_3$), 23.3 (OCMe), 21.7 (d, J=11.0 Hz, NCHMe$_2$), 21.1 (d, J=5.5 Hz, NCHMe$_2$), 18.4 (SiCMe$_3$), 12.5 (C=CMe), −5.4 (SiMe$_2$), −5.5 (SiMe$_2$); $^3$P NMR (81 MHz, CDCl$_3$) δ135.1

Example 11

Phosphoramidite (14)

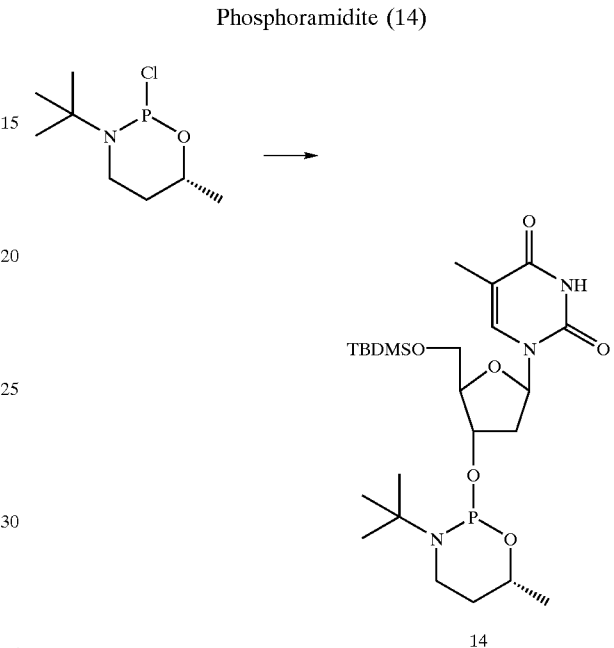

14

To a solution of 0.2 ml (315 mg, 2.3 mmol) phosphorus trichloride in 10 ml dichloromethane was added a solution of 320 mg (2.2 mmol) butanol 31 and 0.7 ml triethylamine in 5 ml dichloromethane with vigorous stirring under nitrogen at 0° C. and then at room temperature for 0.5 hour. The solvent was removed by evaporation under reduced pressure and the residue was extracted with diethyl ether (2×40 ml). After removing the ether, 512 mg residual oil was obtained. Then 209 mg (1.0 mmol) of this residual oil was dissolved in 10 ml dichloromethane, a solution of 200 mg (0.56 mmol) 5'-O-(tert-butyldimethylsilyl)thymidine 1 and 0.16 ml triethylamine (1.1 mmol) in 10 ml CH$_2$Cl$_2$ was added with vigorous stirring under nitrogen at room temperature. The mixture was stirred at room temperature until TLC indicated that the reaction had gone to completion. The reaction mixture was transferred to 100 ml ethyl acetate, which was previously washed with saturated NaHCO$_3$ solution. Saturated NaHCO$_3$ and then water was added to wash the solution. The separated organic phase was dried over MgSO$_4$. A white foam (quantitative yield) was formed after the solvent was removed by evaporation under reduced pressure. Two components were found from $^{31}$P NMR spectra in a ratio of 1:5 (132.4 ppm:130.8 ppm). The reaction mixture in C$_6$D$_6$ was then refluxed for about 4 hours to get a ratio of up to 1:9 (d 137.8 ppm:136.1 ppm in benzene).

Example 12

Phosphoramidite (15)

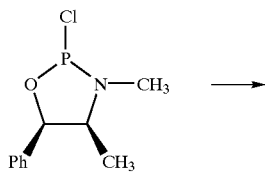

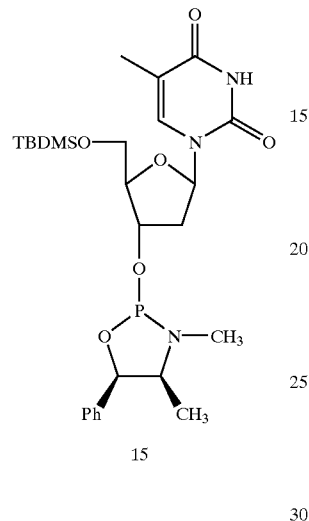

15

To a solution of 6.30 g (4.0 ml, 46 mmol) phosphorus trichloride in 100 ml dichloromethane was added a solution of 6.61 g (40 mmol) (1R,2S) ephedrine and 10.1 g (14 ml, 100 mmol) triethylamine in 50 ml dichloromethane with vigorous stirring under nitrogen at 0° C. and then at room temperature for 0.5 hour. The solvent was removed by evaporation under reduced pressure and the residue was extracted with diethyl ether (3×100 ml). After removing the ether, 9.3 g residual oil was obtained. Then 345 mg (1.5 mmol) of this residual oil was dissolved in 40 ml dichloromethane, a solution of 356 mg (1.0 mmol) 5'-O-(tert-butyldimethylsilyl)thymidine 1 and 0.154 ml triethylamine (111 mg, 1.1 mmol) in 20 ml $CH_2Cl_2$ was added with vigorous stirring under nitrogen at −78° C. The mixture was stirrred at −78° C. until TLC indicated that the reaction had gone to completion. The reaction mixture was quickly transferred to 150 ml ethyl acetate, which was previously washed with cold saturated $NaHCO_3$ solution. Cold saturated $NaHCO_3$ was added to wash the solution. The separated organic phase was dried over $MgSO_4$. A white foam (quantitative yield) was formed after the solvent was removed by evaporation under reduced pressure at 0° C. Two components were found from the $^{31}P$ NMR spectrum in a ratio of 1:2 (147.3 ppm:141.6 ppm). The reaction mixture in $CDCl_3$ was then refluxed for about 4 hours to get a ratio of up to 1:5 (151.5 ppm:143.5 ppm). After chromatography on silica gel column (hexane:ethyl acetate:triethylamine= 5:3:2), the slow eluting component (143.5 ppm) was separated as a pure diastereomer.: $^1H$ NMR (500 MHz, $CDCl_3$) δ7.23–7.50 (m, 5H, Ph), 6.35 (m, 1H, H-1'), 5.60 (d, J=6.8 Hz, 1H, PhCH), 4.71–4.75 (m, 1H, H-5'), 4.01–4.02 (m, 1H, H-4'), 3.78–3.87 (m, 2H, H-5'), 3.52–3.58 (m, 1H, MeCH), 2.64 (d, J=12.2 Hz, 3H, NMe), 2.31–2.36 (m, 1H, H-2'), 2.05–2.11 (m, 1H, H-2'), 1.90 (s, 3H, C=CMe), 0.90 (s, 9H, $CMe_3$), 0.60 (d, J=6.4 Hz, 3H, CHMe), 0.09 (s, 6H, $SiMe_2$); $^{13}C$ NMR (125 MHz, $CDCl_3$) δ163.9 (C-4), 150.5 (C-2), 137.9 (Ph), 135.3 (C-6), 128.1 (Ph), 127.7 (Ph), 126.7 (Ph), 1111.0 (C-5), 86.7 (d, J=1.8 Hz, C-4'), 84.7 (OCPh), 84.6 (d, J=9.2 Hz, C-1'), 73.1 (d, J=18.3 Hz, C-3'), 63.0 (C-5'), 57.5 (d, J=5.6 Hz, NCMe), 40.6 (d, J=5.5 Hz, C-2'), 28.8 (d, J=17.4, $NCH_3$), 25.9 ($SiCMe_3$), 18.3 ($SiCMe_3$), 14.6 (d, J=3.7 Hz, NCHMe), 12.5 (C=CMe), −5.4 ($SiMe_2$), −5.5 ($SiMe_2$); $^{31}P$ NMR (81 MHz, $CD_3CN$) δ143.5

Example 13

Phopshite Triester (20a) from Phosphoramidite 13a with MeOH

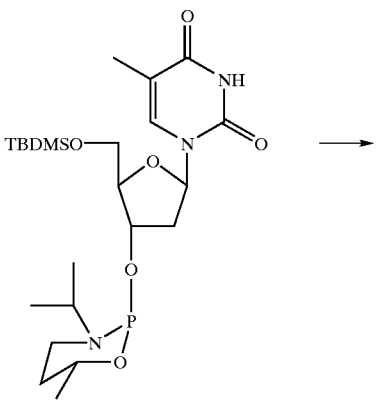

13a

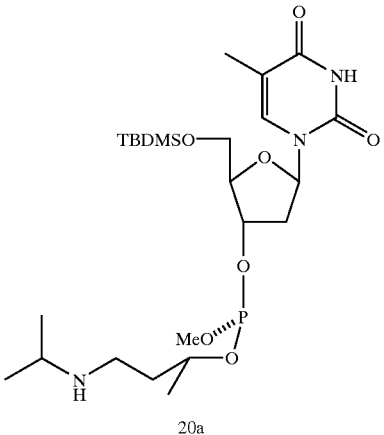

20a

Diastereomeric pure phosphoramidite 13a (10 mg, fast eluting component) in 0.5 ml $CDCl_3$ was put in 5 mm NMR tube, and 50 μl of dry MeOH (a large excesses) was then added by syringe, followed by 1 mg of dicyanoimidazole. The reaction was monitored by $^{31}P$ NMR until the reaction went to completion. The phosphite triesters formed in a ratio of 10:1 (139.4 ppm:138.8 ppm) and were purified on a silica gel column.: $^1H$ NMR (500 MHz, $CDCl_3$) δ7.48 (s, 1H, H!6), 6.35 (dd, J=5.4, 8.8 Hz, 1H, H-1'), 4.78–4.82 (m, 1H, H-31), 4.24–4.33 (m, 1H, OCH), 4.10 (d, J=2.4 Hz, 1H, H-4'), 3.76–3.89 (m, 2H, H-5'), 3.50 (d, J=10.7 Hz, 3H, $CH_3$), 2.78 (m, 1H, NCH), 2.65 (m, 2H, $NCH_2$), 2.40 (m, 1H, H-2'), 2.04 (m, 1H, H-2'), 1.89 (d, J=1.0 Hz, 3H, C=C—$CH_3$), 1.64–1.78 (m, 2H, $OCHCH_2$), 1.25 (d, J=6.4 Hz, 3H, $OCHCH_3$), 1.03 (d, J=6.3 Hz, 6H, $NCHMe_2$), 0.91 (s, 9H, $SiCMe_3$), 0.10 (d, J=2.0 Hz, 6H, $SiMe_2$); $^{13}C$ NMR (125 MHz, CDCl$_3$) δ163.5 (C-4), 150.1 (C-2), 135.3 (C-6), 10.9 (C-5), 86.5 (d, J=2.7 Hz, C-4'), 84.8 (C-1'), 72.1 (d, J=8.2 Hz, C-3'), 69.5 (OCH), 63.0 (C-5'), 49.2 (d, J=9.2 Hz, OCH$_3$), 48.8 (Me$_2$CNH), 40.3 (d, J=3.7 Hz, C-2'), 38.7 (d, J=4 6 Hz, CH$_2$), 25.9 (SiCMe$_3$), 22.9 (d, J=3.7 Hz, NCHMe), δ18.3 (SiCMe ), 2.5 (C=CMe), −5.4 (SiMe$_2$); $^{31}$P NMR (121 MHz, CDCl$_3$) δ139.4

Example 14

Phophite Triester (20b) from Phosphoramidite 13b with Methanol

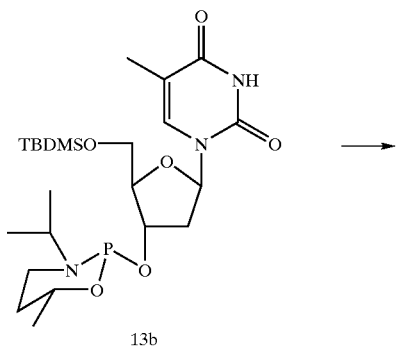

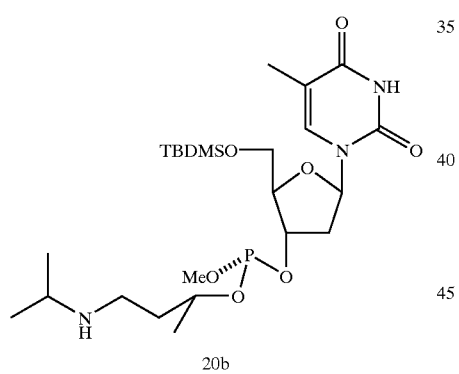

Diastereomeric enriched (75%) phosphoramidite 13b (10 mg, slow eluting component) in 0.5 ml CDCl$_3$ was put in 5 mm NMR tube, and 50 μl dry MeOH (a large excess) was then added by syringe, followed by 1 mg of dichloroimidazole. The reaction was monitored by $^{31}$P NMR until the reaction went to completion. The phosphite triesters formed in a ratio of 1:2 (139.4 ppm:138.8 ppm) were purified on a silica gel column. $^1$H NMR (500 MHz, CDCl$_3$) 6 7.48 (s, 1H, H-6), 6.34 (m, 1H, H-1'), 4.78–4.82 (m, 1H, H-3'), 4.25–4.33 (m, 1H, OCH), 4.11 (d, J=2.4 Hz, 1H, H-4'), 3.77–3.89 (m, 2H, H-5'), 3.49 (d, J=10.3 Hz, 3H, CH$_3$), 2.76 (m, 1H, NCH), 2.64 (m, 2H, NCH$_2$), 2.39 (m, 1H, H-2'), 2.05 (m, 1H, H-2'), 1.90 (s, 3H, C=C—CH$_3$), 1.65–1.78 (m, 2H, OCCH$_2$), 1.26 (d, J=6.4 Hz, 3H, OCHCH$_3$), 1.04 (d, J=6.4 Hz, 6H, NCHMe$_2$), 0.91 (s, 9H, SiCMe$_3$), 0.10 (d, J=2.0 Hz, 6H, SiMe$_2$); $^{31}$P NMR (121 MHz, CDCl$_3$) δ138.8

Example 15

Phophite Triester (32) from Phosphoramidite 13a with n-Butanol

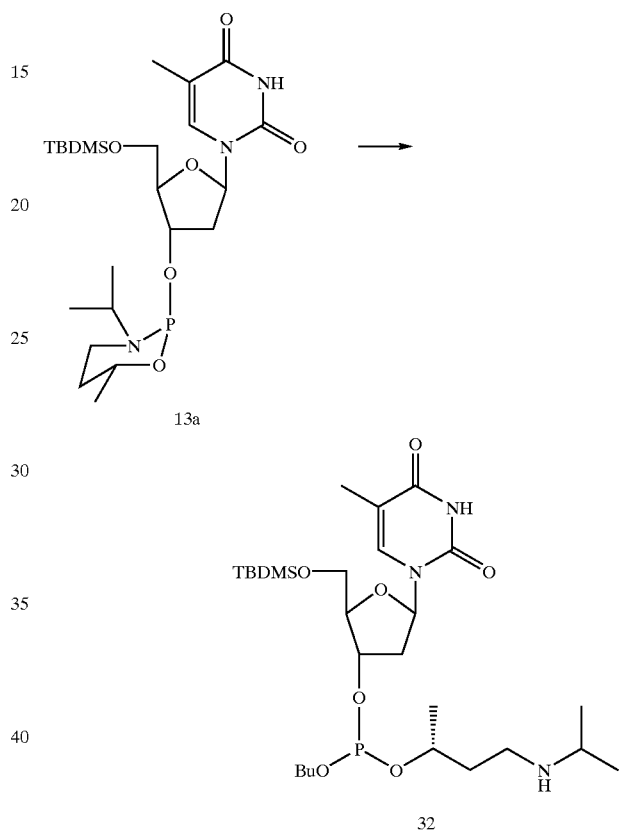

Diastereomerically pure phosphoramidite 13a (10 mg, fast eluting component) in 0.5 ml CDCl$_3$ was placed in 5 mm NMR tube, and 50 μl dry n-butanol (a large excess) was then added by syringe, followed by 1 mg of dicyanoimidazole. The reaction was monitored by $^{31}$P NMR until the reaction went to completion. The phosphite triesters formed in a ratio of 7:1 (138.9 ppm:138.5 ppm) were purified on a silica gel column. $^1$H NMR (500 MHz, CDCl$_3$) δ7.49 (d, J=1.5 Hz, 1H, H-6), 6.35 (dd, J=5.5, 8.8 Hz, 1H, H-1'), 4.83 (m, 1H, H-3'), 4.24–4.31 (m, 1H, OCH), 4.11 (d, J=2.0 Hz, 1H, H-4'), 3.71–3.89 (m, 4H, 2H-5', OCH$_2$), 2.78 (m, 1H, NCH), 2.66 (m, 2H, NCH$_2$), 2.39 (m, 1H, H-2'), 2.02 (m, 1H, H-2'), 1.89 (s, 3H, C=C—CH$_3$), 1.63–1.77 (m, 2H, OCMeCH$_2$), 1.57 (m, 2H, CH$_2$), 1.36 (m, 2H, CH$_2$), 1.24 (d, J=6.3 Hz, 3H, OCHCH$_3$), 1.04 (d, J=6.3 Hz, 6H, NCHMe$_2$), 0.91 (s, 9H, SiCMe$_3$), 0.10 (d, J=2.0 Hz, 6H, SiMe$_2$); $^{31}$P NMR (121 MHz, CDCl3) δ138.9.

Example 16

Phosphite Triester (33a) from Phosphoramidite 7a with Methanol

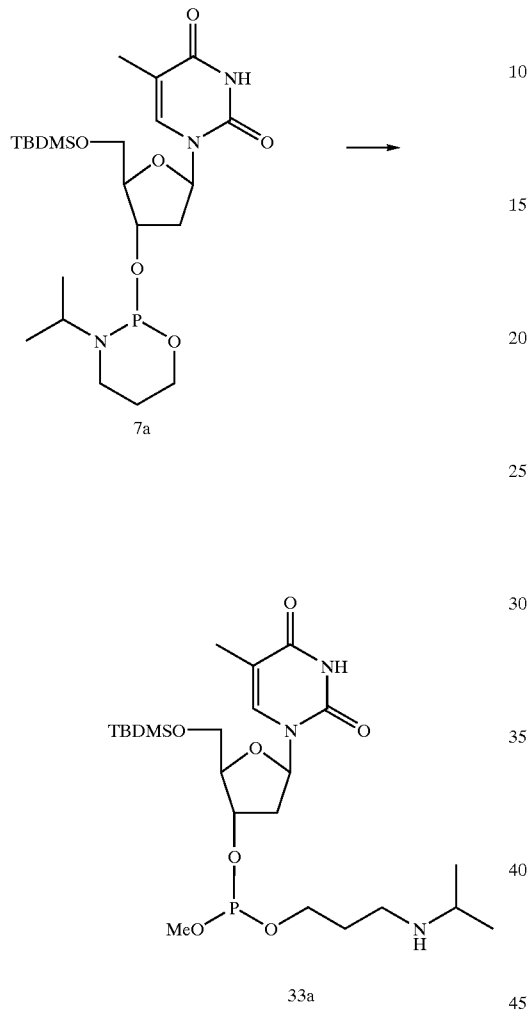

Diastereomerically pure phosphoramidite 7a (10 mg, fast eluting component) in 0.5 ml CDCl₃ was put in 5 mm NMR tube, and 50 µl dry methanol (a large excess) was then added by syringe, followed by 1 mg of 4,5-dicyano-2-bromoimidazole. The reaction was monitored by $^{31}$P NMR until the reation went to completion. The phosphite triester consisted of only one diastereomer (139.1 ppm) and was purified on a silica gel column. $^1$H NMR (500 MHz, CDCl₃) δ7.48 (s, 1H, H-6), 6.34 (dd, J=5.4, 8.8 Hz, 1H, H-1'), 4.78 (m, 1H, H-3'), 4.09 (m, 1H, H-4'), 3.76–3.89 (m, 4H, 2H-5', OCH₂), 3.50 (d, J=10.2 Hz, 3H, OCH₃), 2.80 (m, 1H, NCHMe₂), 2.67 (t, J=6.8 Hz, 2H, NHCH₂), 2.39 (m, 1H, H-2'), 2.05 (m, 1H, H-2'), 1.90 (s, 3H, C=C—CH₃), 1.78 (m, 2H, OCHCH₃), 1.03 (d, J=6.3 Hz, 6H, NCHMe₂), 0.91 (s, 9H, SiCMe₃), 0.10 (s, 6H, SiMe₂); $^{31}$P NMR (121 MHz, CDCl₃) δ139.1; MS(CI) m/e: 534 ([M+H⁺], 100%), 502 (14.4), 376 (13.6), 339 (74.6), 281 (20.4), 164 (59.8)

Example 17

Phophite Triester (33b) from Phosphoramidite 7b with Methanol

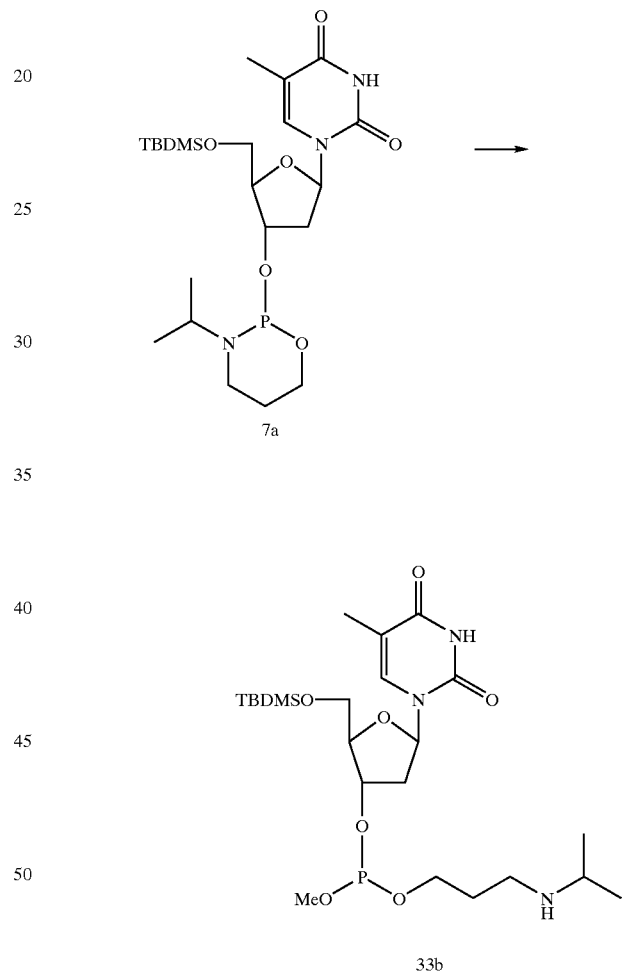

Diastereomerically enriched (92%) phosphoramidite 7b (10 mg, slow eluting component) in 0.5 ml CDCl₃ was placed in 5 mm NMR tube, and 50 l dry methanol (a large excess) was then added by syringe, followed by 1 mg of dicyanobromoimidazole. The reaction was monitored by $^{31}$P NMR until the reaction went to completion. Diastereomerically enriched phosphite triester 33b (92%) in a ratio of 1:11 (139.2 ppm:138.8 ppm) was purified on a silica gel column. $^{31}$P NMR (121 MHz, CDCl₃) δ138.8

Example 18

Thiophosphonate (44)

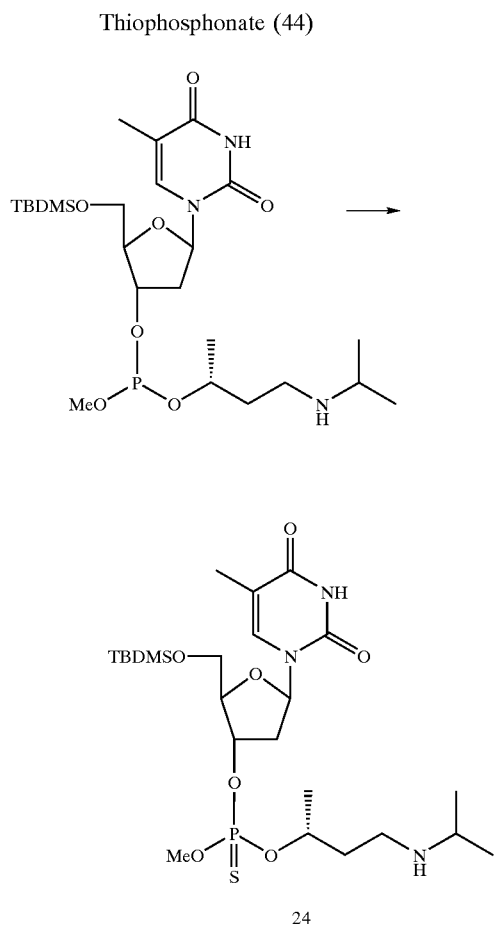

Diastereomerically pure 13a (100 mg, fast eluting component) was dissolved in 5 ml CDCl$_3$, and 0.5 ml MeOH was then added by syringe, followed by 5 mg of 2-bromo-4,5-dicyanoimidazole. The reaction was monitored by $^{31}$P NMR until the reaction went to completion with almost only one diastereomer of phosphite triester 20a (139.4 ppm) being found, and then 10 mg sulfur was added. Within 5 minutes, the sulfurization went to completion. After chromatography (ethyl acetate:triethylamine=1:1), sulfurized product 24 was obtained in an oily form. $^1$H NMR (500 MHz, CDCl$_3$) δ7.50 (d, J=1.4 Hz, H, H-6), 6.36 (dd, J=5.4, 9.3 Hz, 1H, H-1'), 5.08 (m, 1H, H-3'), 4.63–4.72 (m, 1H, OCH), 4.25 (m, 1H, H-4'), 3.88 (m, 2H, H-5'), 3.73 (d, J=13.7 Hz, 3H, OCH$_3$), 2.77 (m, 1H, NCHMe)$_2$, 2.67 (t, J=6.4 Hz, 2H, NCH$_2$), 2.48 (m, 1H, H-2'), 2.09 (m, 1H, H-2'), 1.90 (d, J=1.5 Hz, 3H, C=C—CH$_3$), 1.70–1.86 (m, 2H, OCCH$_2$), 1.32 (d, J=5.9 Hz, 3H, OCHCH$_3$), 1.04 (dd, J=2.9, 5.9 Hz, 6H, NCHMe$_2$), 0.92 (s, 9H, SiCMe$_3$), 0.12 (s, 6H, SiMe$_2$); $^{31}$P NMR (121 MHz, CDCl$_3$) δ67.5

Example 19

2-Bromo-4,5-dicyanoimidazole (21)

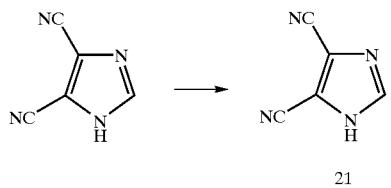

To 1.18 g (10 mmol) 4,5-dicyanoimidazole and 25 ml 0.1 M NaOH was added 1.8 ml Br$_2$ (35 mmol). The mixture was stirred overnight at room temperature and then acidified with dilute HCl. The solid was filtered, rinsed with water and recrystallized from water to give 1.5 g of dicyanobromoimidazole 21 (yield 76.4%).: m.p. 147–149° C .(lit. 141–143° C.); Rf=0.65 (ethyl acetate:methanol=4:1); MS(EI): 198 ([M+2], 96%), 196 ([M$^+$], 100%),171 (28.5), 169 (29.2), 117 (27.4), 91 (19.0), 64 (20.6), 53 (22.4), 38 (18.8).

Example 20

Synthesis of (S)-methyl-3-(5-imidazolyl)-2-hydroxypropionate (3) Hydrochloride

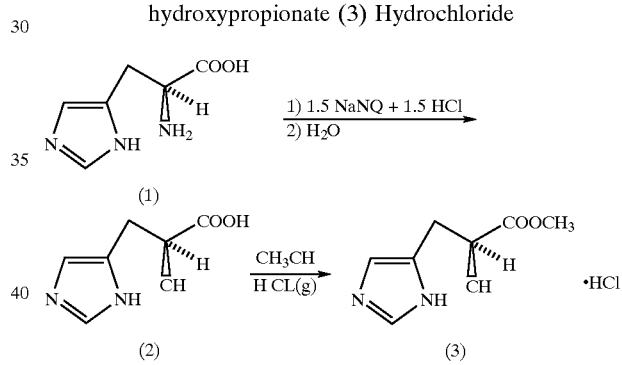

(L)-Histidine (3.103 g, 20 mmol) was first dissolved in 30 ml of 1 N hydrochloric acid solution. This solution was cooled down to 0° C., then a solution of sodium nitrite (2.070 g, 30 mmol) in 10 ml distilled water was added dropwise over a period of 1 hour. The solution was stirred overnight at 0° C., then evaporated to dryness in vacuo with heating. 20 ml of distilled water was added to the solid residue, the mixture was evaporated once more with toluene in order to azeotropically remove the water residue as much as possible. After drying the compound in high vacuum overnight and without isolation of the intermediate acid, the mixture was dissolved into 50 ml of dry methanol and stirred under Ar. This solution was cooled down to 0° C. and a stream of gaseous hydrogen chloride was bubbled through the mixture. After 1.5 hours, TLC indicated disappearance of the acid and the reaction was stopped. The mixture was evaporated in vacuo with heating to yield a sticky yellow solid that could be crystallized from a mixture of ethanol and ether to yield 3.10 g of (2).HCl, m.p. 139–142° C., [α]$_D$ −21° (c 1.9, methanol, 25° C.) (litt. −22° ) $^1$HNMR (200

MHz, CD$_3$OD) δ8.90 (s, 1H, NCHN); 7.30 (s, 1H, NCHC); 4.40 (dd, ABX, $^3J_{Ha-Hx}$=5.40 Hz, $^3J_{Hb-HX}$=5.00 Hz, CHOH); 3.72 (s, 3H, OCH$_3$); 2.85–3.10 (ABX, 2H, $^2J_{Ha-Hb}$=13.75 Hz, $^3J_{Hb-Hx}$=5.0 Hz, $^3J_{Ha-Hx}$=5.4 Hz, CH$_2$); $^{13}$C NMR (non decoupled) (125 MHz, D$_2$O) δ175.3 (s,CO); 134.2 (d, NCHN); 129.7 (s, CH$_2$CN); 117.6 (d, CCHN); 69.9 (d, CHOH); 53.6 (q, CH$_3$); 29.5 (t,CH$_2$); M.S. (M+1)$^+$.171

Example 21

Synthesis of Imidazo-oxazaphospholidine (4)

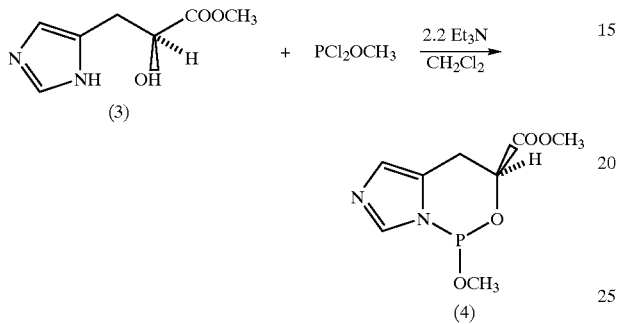

In scrupulously dry glassware, compound (3) (0.236 g, 1.39 mmol) was added and dried in vacuo overnight, then put under an atmosphere of Ar. This compound was suspended into 5 ml of dry ether, then triethylamine (0.20 ml, 3.15 mmol) was added. The suspension was cooled down to 0° C. and stirred under Ar. Then, methyl dichlorophosphite (0.15 ml, 1.58 mmol) was syringed into the mixture quickly. As soon as the phosphite was introduced, a thick white precipitate was observed, corresponding to the formation of triethylammonium chloride. After 15 min, $^{31}$P NMR showed several signals between 176 and 120 ppm, as well as after 2 to 4 hours. After overnight stirring at room temperature, $^{31}$P NMR showed a single signal at 143.5 ppm. Compound decomposed upon trying to handle it (dilution in dry ether, filtration in an Ar atmosphere, concentration by evaporation of the ether) as indicated by $^{31}$P NMR by several peaks at 5–20 ppm, corresponding most likely to H-phosphonates derivatives. Changing the reaction conditions did not bring any improvement.

Therefore, compound (4) could not be further purified and analyzed.

Example 22

Synthesis of 1-tritylimidazole (5)

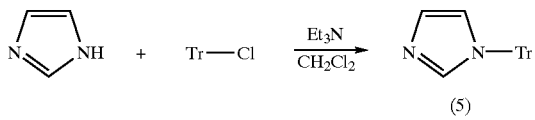

To a solution of trityl chloride (5.58 g, 20.0 mmol.) in dry methylene chloride (100 ml) cooled down to 0° C. and stirred under Ar, was added dropwise over 1.5 hours a solution of imidazole (1.36 g, 20.0 mmol.) and triethylamine (2.7 mml, 20 mmol.) in 50 ml dry methylene chloride. At the end of the addition, the reaction mixture was allowed to warm up to room temperature and stirred under Ar at that temperature overnight. The reaction mixture was then washed with 20 ml of a 10% solution of ammonium chloride, then with 20 ml of distilled water. The organic phase was dried over magnesium sulfate and evaporated in vacuo to yield quantitatively a white solid. Recrystallization from methylene chloride/hexanes yielded 5.60 g of (5) (yield=90% after recrystallization). m.p. 214° C.; $^1$H NMR (200 MHz, CDCl$_3$) δ7.43 (m, 1H, NCHN), 7.3–7.4 (m, 9H, 3×C$_6$H$_5$), 7.1–7.2 (m, GH, 3×C$_6$H$_5$), 7.0 (m, 1H, Ph$_3$CNCH=CH), 6.81 (m, 1H, Ph$_3$CNCH=CH); $^{13}$C NMR (50 MHz, CDCl$_3$) δ142.3, 139.0, 129.6, 128.2, 128.3, 121.6.

Example 23

Synthesis of (S)-1-(2-(1-triphenylmethyl)-imidazolyl)-propan-2-ol (S)-(6)

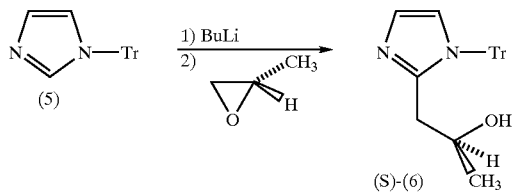

To a solution of N-tritylimidazole (1.55 g, 5 mmol) in freshly distilled THF (50 ml) cooled down to −78° C. and stirred under dry Ar, was added a 2.5 M solution of n-butyllithium in pentane (2.4 ml, 6 mmol). The addition lasted for 30 min, and the deep red solution obtained was allowed to warm up to 0° C., stirred at room temperature for 1 hour, then cooled down again to −78° C. At that temperature, (S)-propylene oxide (0.35 g, 6 mmol) was added dropwise. After 30 min, the solution was allowed to warm up to 0° C. and was stirred at that temperature for 12 hours until TLC indicated that the reaction did not further proceed. The solution was poured into 50 ml of saturated NH$_4$Cl solution, and the resulting mixture was extracted with CH$_2$Cl$_2$. After flash chromatography (hexane:acetone:triethylamine 78:21:1), 1.44 g of the pure product was collected in 78% yield: m.p. 201° C.; $^1$H NMR (200 MHz, CDCl$_3$) δ7.20–7.40 (m, 9H, 3×C$_6$H$_5$), 7.10–7.18 (m, 6H, 3×C$_6$H$_5$), 6.90 (d, 1H, $^3J_{H-H}$=1.2; CHNCPh$_3$), 6.71(d, 1H, $^3J_{H-H}$32 1.2; CH=CHNCPh$_3$), 5.83 (b, 1H, OH), 3.40–3.60 (m, 1H, CHCH$_3$), 1.78–2.05 (ABX, 2H, $^3J_{Hb-Hx}$=3.2 Hz, $^3J_{Ha-Hx}$=8.5 Hz, $^2J$Ha-Hb=1.2 Hz, CH$_2$), 0.81 (d, $^3J_{H-H}$=6.0 Hz, 3H, CH$_3$); $^{13}$C NMR (50 Mhz, CDCl$_3$) δ_149.2, 142.1, 129.6, 127.9, 127.7, 124.7, 121.0 (NCCN), 74.6, 65.0 (CHOH), 38.1 (CH$_2$), 22.3 (CH$_3$).

Example 24

Synthesis of (S)-1-(2-imidazolyl)-propan-2-ol (S)-(7)

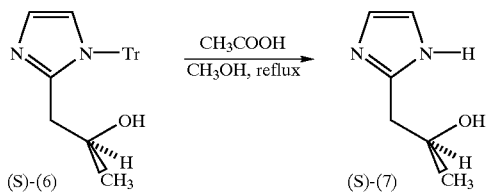

A solution of N-tritylimidazolylpropanol (S)-(6) (2.39 g, 6.51 mmol) in 80 ml methanol containing 4.3 ml glacial acetic acid (5%) was refluxed for about 12 hours. After that time, TLC indicated disappearance of the starting materials. The mixture was concentrated in vacuo and a white precipitate appeared upon addition of 50 ml of cold distilled water. The mixture was chilled, then filtered, and the white precipitate was washed with cold distilled water (10 ml). The filtrate was then evaporated twice, and the residual yellow oil redissolved in 50 ml dry methanol and passed through the weakly basic anion exchange resin (hydroxide form) IRA-68. The solution was then evaporated to yield a solid residue that could be recrystallized from a mixture of methanol and ethyl acetate. yield: 0.80 g, 98% of pure (S)-(7). m.p. 119–121° C.; $^1$H NMR (200 Mhz, $CD_3OD$) δ6.96 (s, 2H, NCHCHN); 3.96 (m, 1H, CHCH$_3$); 2.4–2.65 (ABX, $^3J_{H\text{-}H}$=6.3 Hz, $^3J_{Hb\text{-}H}$=6.7 Hz, $^3J_{Ha\text{-}Hb}$=14.5 Hz, CH$_2$); 0.87 (d, 3H, $^3J_{H\text{-}H}$=6.3 Hz, CH$_3$); $^{13}$C NMR (50 MHz, $CD_3OD$) δ145.8 (s, CH2CNH); 121.2 (d, NCH=CHNH); 67.1 (d, CHOH); 38.4 (t, CH2); 23.1 (q, CH3); MS (CI): [M+1]$^+$. 127

Example 25

Synthesis of 1-methoxy-3-methyl-imidazo-[2,1-e]-(3,4-dihydro)-oxazaphosphorine (8)

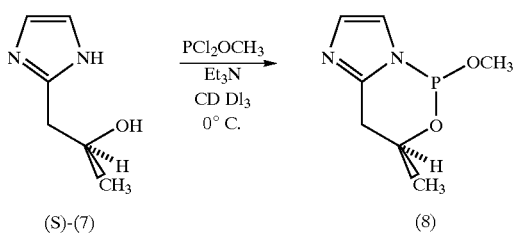

In an NMR tube previously dried in vacuo and under Ar was introduced 23.0 mg (0.20 mmol) of (S)-(2-imidazolyl)-propan-2-ol (S)-(7), then the tube was sealed with a septum and flushed with Ar. CDCl$_3$ (0.7 ml) was then introduced, followed by 127 μl (1.0 mmol) of triethylamine. The alcohol did not dissolve, and this suspension was cooled down to 0° C. while shaking the tube. At that temperature, 18.9 μl (0.20 mmol) of methyl dichlorophosphite was syringed inside the tube. Upon shaking, the alcohol dissolved instantaneously, and an exothermic reaction was noticed. After about 1 hour, $^{31}$P NMR revealed the presence of several peaks around 120–140 ppm. After about 3 hours, a single product (8) was observed by $^{31}$P NMR, as evidenced by its chemical shift at 118.8 ppm. There was no further characterization of this compound, as all efforts to isolate it have been unsuccessful and have led to the hydrolysis of this extremely water sensitive bicyclic structure, most likely to the corresponding H-phosphonate.

Example 26

Synthesis of 1-ethoxy-3-methyl-imidazo-[2,1-e]-(3,4-dihydro)-oxazaphosphorine (9)

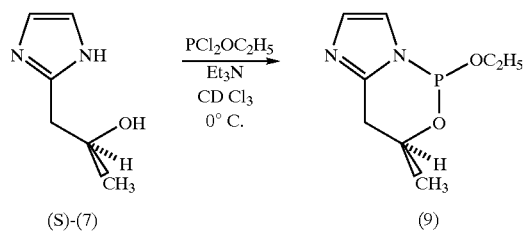

To an NMR tube previously dried in vacuo and under Ar, was introduced 18.9 mg (0.15 mmol) of (S)-(2-imidazolyl)-propan-2-ol (S)-(7). The tube was then sealed with a septum and flushed with Ar. Then, 0.7 ml CDCl$_3$ was introduced, followed by 105 μl (0.75 mmol) of triethylamine. The alcohol did not dissolve, and this suspension was cooled down to 0° C. while shaking the tube. At that temperature, 17.2 μl (0.15 mmol) of ethyl dichlorophosphite was syringed into the NMR tube. Upon shaking, the alcohol dissolved instantaneously, and an exothermic reaction was noticed. After about 2 hours, a single product was observed by $^{31}$P NMR as evidenced by its chemical shift at 118.2 ppm. After about 1 hour, the presence of other products around 120–140 ppm was noticed, one of which (121.1 ppm) is probably the other diastereomer. There was no further characterization of this compound.

Example 27

Synthesis of Thiophosphate Ethyl (S)-1-(2-imidazolyl)-prop-2-yl Isopropyl Ester (22)

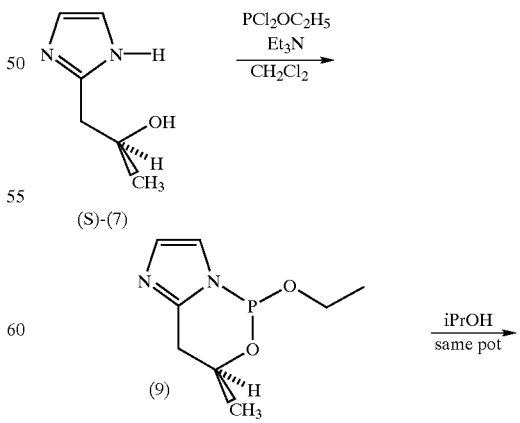

1 diastereomer only, stereochemistry non established at phosphorus

53
-continued

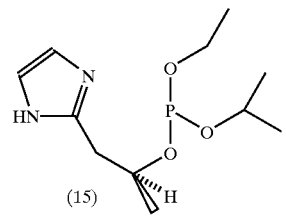

(15)

same remark

↓ S₈, same pot

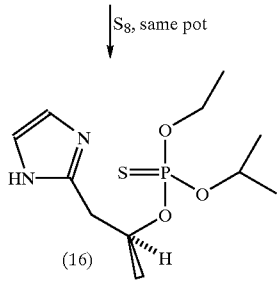

(16)

In an NMR tube, to a suspension of 18.9 mg (0.15 mmol) (S)-1-(2-imidazolyl)-propan-2-ol (S)-(7) in 0.7 ml dry deuterated chloroform and 0.21 ml triethylamine (1.5 mmol), shaken at room temperature under Ar was introduced with a syringe 17.2 μl (0.15 mmol) of ethyl dichlorophosphite. The reaction mixture was shaken at room temperature and the chiral imidazolylpropanol dissolved immediately in an exothermic process. At that point, $^{31}$P NMR indicated the formation of several products, among which was one having a signal at 118.3 ppm and one having a signal at 120.5 ppm. (suspected diastereomers). After one hour and regular shaking of the NMR tube, $^{31}$P NMR indicated only one peak at 118.3 ppm. At that stage, 20 μ(0.45 mmol) of isopropanol was introduced, and the tube was shaken again. $^{31}$P NMR indicated after 20 min the presence of a single peak at 140.6 ppm, indicating that the displacement of the imidazole moiety had given rise to a single diastereomer (19). 32 mg sulfur (1 mmol) was then introduced and the $^{31}$P-NMR was again recorded. The spectrum indicated a single peak at 64.8 ppm. The product (22) was then concentrated in vacuo and purified by flash chromatography (ethyl acetate/hexanes/triethylamine 79/20/1). $^{1}$H NMR (200 MHz, CDCl₃) 6.96 (s, 2H, NCH=CH—N); 4.83–4.97 (m, 1H, P—O—CH—CH₃); 4.58–4.75 (dh, 1H, $^{3}J_{H-H}$=6.2 Hz, $^{3}J_{H-P}$=9.6 Hz, OCH (CH₃)₂); 3.96–4.12 (m, 2H, P—O—CH₂CH₃); 2.98–3.20 (2×ABX, 2H, $^{2}J_{Ha-H}$=15.5 Hz, $^{3}J_{Ha-Hx}$=6.23 Hz, $^{3}J_{Hb-Hx}$=4.6 Hz, $^{4}J_{H-P}$=1.5 Hz, CH₂CHCH₃); 1.21–1.34 (m, 12H, CH(CH₃)+CH(CH₃)₂+CH₂CH₃) $^{13}$C NMR (50 MHz, CDCl₃) 144.00 (s, N—C=N); 121.70 (s, N—C=C—N); 74.90 (d, $^{2}J_{C-P}$=6.1 Hz, P—O—CH—(CH₃)CH₂); 73.80 (d, $^{2}J_{C-P}$=5.7 Hz, P—O—CH₂—CH₃); 64.25 (d, $^{2}J_{C-P}$=5.8 Hz, P—O—CH(CH₃)₂); 35.95 (s, P—O—CH(CH₃)CH₂—); 23.40 (s, P—O—CH(CH₃)₂); 21.06 (s, P—O—CH(CH₃) CH₂—); 15.83 (S, P—O—CH₂—CH₃) $^{31}$P NMR (81 MHz, CDCl₃) δ64.8 ppm M.S. (CI), [M+1]⁺. 293.

54

Example 28

Synthesis of Thiophosphate Ethyl (S)-1-(2-imidazolyl)-prop-2-yl 5'terbutyldimethylsilylthymidinyl Ester (19)

(S)-(7)

PCl₂OC₂H₅
Et₃N
―――――→
CH₂Cl₂

(9)

5'-tBDMS-thymidine
―――――――――→
same pot 1 diastereomer only, stereochemistry non established at phosphorus same remark ↓ S₈, same pot (19)

To a suspension of (S)-imidazolylpropanol (S)-(7) (0.30 mmol, 37.8 mg) in 2 ml dry dichloromethane and triethylamine (1.5 mmol, 0.21 ml) cooled down to 0° C. and stirred under Ar, was slowly added ethyl dichlorophosphite (0.30 mmol, 35 μl). The reaction mixture was then allowed to warm up to room temperature, the solid starting materials dissolved, and after about 2 hours, $^{31}$P NMR indicated the presence of a single peak at 118.3 ppm. At that time, the mixture was cooled down to 0° C. again, and at that temperature was added a mixture of 5'-tBDMS-thymidine (1) (0.30 mmol, 106 mg) in 1.5 ml of dry methylene chloride. The reaction mixture was allowed to warm up to room temperature again. $^{31}$P NMR indicated, after 30 min, a full conversion of the peak at 118.3 ppm to a single peak at 141.2 ppm, assigned to (23). Elemental sulfur S₈ (0.9 mmol, 29 mg) was then added after about 30 minutes. $^{31}$P NMR indicated conversion of the previously formed product to a single product (24) with a peak at 66.3 ppm. Evaporation of the reaction mixture followed by flash chromatography (ethyl acetate/triethylamine 80/20) afforded thioate (24) as a sticky solid (127 mg, 72%). $^1$H NMR (300 MHz, CD$_2$Cl$_2$) δ7.48 (d, 1H, $^4J_{H-H}$=1.3 Hz, C=CH); 6.94 (s, 2H, NCH=CHN); 6.25 (dd, 1H, $^3J_{H-H}$=5.1 Hz, $^3J_{H-H}$=9.2 Hz, NCHO); 4.84–5.05 (m, 2H, POCH(CH$_3$)CH$_2$+ POCHCH$_2$O); 4.15–4.24 (m, 1H, SiOCH$_2$CHO); 3.96–4.14 (dq, 2H, $^3J_{H-P}$=9.4 Hz, $^3J_{H-H}$=7.0 Hz, POCH$_2$CH$_3$); 3.76–3.92 (ABX, 2H, $^2J_{Ha-Hb}$=11.5 Hz, $^3J_{Hb-Hx}$=2.5 Hz, $^3J_{Ha-Hx}$=2.4 Hz, SiOCH$_2$CHO); 2.98–3.08 (dd, 2H, $^3J_{H-H}$=5.8 Hz, $^4J_{H-P}$=1.1 Hz, POCH(CH$_3$)CH$_2$-Im); 1.98–2.08 (m, 2H, POCHCH$_2$CHN); 1.88 (s, 3H, CH=CCH )$_3$; 1.39 (d, 3H, $^3J_{H-H}$=6.2 Hz, POCH(CH$_3$)); 1.28 (dt, 3H, $^3J_{H-H}$=7.0 Hz, $^4J_{H-P}$=0.9 Hz, POCH$_2$CH$_3$); 0.91 (s, 9H, SiC(CH$_3$)$_3$); 0.12 (s, 6H, Si(CH$_3$)$_2$).

$^{13}$C NMR (121 MHz, CD$_2$Cl$_2$, decoupled from $^1$H) δ164.1 (s, NCOC(CH$_3$)); 151.1 (s, NCON); 144.2 (S, NC=N); 135.5 (s, NC=C(CH$_3$)C=O); 132.4 (s, NC=CN); 186.1 (s, 11.5 (C(CH$_3$)CO); 86.1 (s, SiOCH$_2$CHO); 86.0 (s, NCHO); 79.9 (d, $^2J_{C-P}$=4.4 Hz, POCH(CH$_3$)); 76.2 (d, $^2J_{C-P}$=5.7 Hz, POCH$_2$CH$_3$); 65.0 (d, $^2J_{C-P}$=5.6 Hz, POCHCHO); 63.8 (s, SiOCH$_2$); 39.4 (s, POCHCH$_2$CHN); 36.6 (POCH(CH$_3$)CH$_2$); 26.1 (SiC(CH$_3$)$_3$); 21.3 (POCH(CH$_3$)); 18.6 (SiC(CH$_3$)$_3$); 16.0 (s, POCH$_2$CH$_3$); 12.7 (s, C=CCH$_3$); −5.4 (d, Si(CH$_3$)$_2$); MS (CI) (M+1)$^+$ 589.

Example 29

1,2-O-3,5-O-dicyclopentylidene-D-xylofuranose (25)

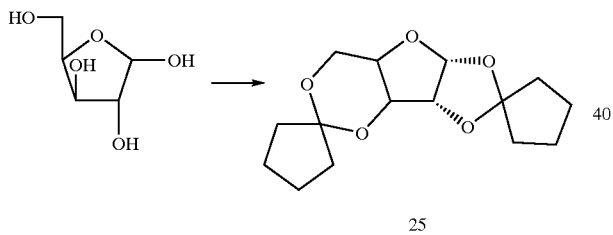

25

To a solution of trimethyl orthoformate (5 mmol, 547 μl) and p-toluene sulfonic acid (0.2 mmol, 38 mg) in dioxane (10 ml) under a nitrogen atmosphere at 0° C., was added dropwise cyclopentanone (40 mmol, 3.5 ml). This solution was stirred at room temperature for 2 hours and D-xylose (2 mmol, 300 mg) was added with stirring continued overnight. Then the reaction mixture was neutralized with triethylamine. Evaporation of the solvent furnished a yellow syrupy residue. A solution of the syrupy residue in chloroform (20 ml) was washed with water (20 ml). The aqueous layer was extracted with chloroform (3×5 ml). The combined chloroform layers were dried (MgSO$_4$). After removing the solvent, the mixture was chromatographed on a silica gel column (Hexane:Ethyl acetate=5:1) to give 340 mg white solid (60%). $^1$HNMR(200 MHz, CDCl3) δ5.99 (δ, J=3.80 Hz, 1H, H-1), 4.45 (d, J=3.81 Hz, 1H, H-2), 4.24 (d, J=2.15 Hz, 1H, H-3), 4.14–3.46 (m, 3H, H-4, 2×H-5), 1.98–1.55 (m, 16H, cyclopentylidene protons); $^{13}$C NMR (125 MHz, CDCl$_3$) δ121.23 (C-1OCOC-2), 109.24 (C-3OCOC-5), 105.08 (C-1), 84.49 (C-2), 74.25 (C-4), 71.83 (C-3), 61.50 (C-5), 39.52, 36.82, 36.19, 29.74, 24.09, 23.49, 22.80, 22.37 (cyclopentylidene carbons); MS (CI) m/e: 283(M+H$^+$).

Example 30

1,2-O-cyclopentylidene-D-xylofuranose (26)

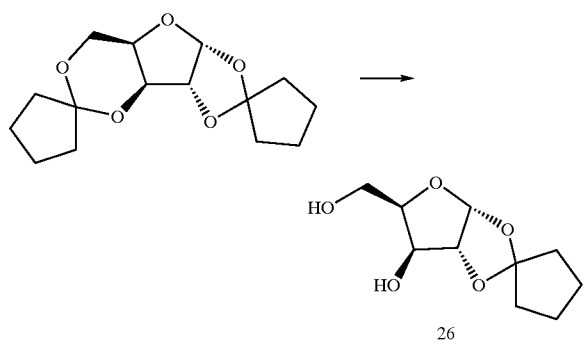

26

The 1,2-O-3,5-O-dicyclopentylidene-D-xylofuranose (25) (1 mmol, 282 mg) was dissolved in acetic acid-water (2:1) (14 ml) at room temperature. The reaction mixture was stirred for 3 hours, followed by TLC. Solvent was evaporated with high vacum, and coevaporated with methanol three times and dried in vacuo overnight to give 196 mg white solid (91%). $^1$H NMR (500 MHz, CDCl$_3$) δ5.94 (d, J=3.91 Hz, 1H, H-1), 4.44 (d, J=3.91 Hz, 1H, H-2), 4.32 (d, J=2.44 Hz, 1H, H-3), 4.18 (m, 1H, H-4), 4.10–4.02 (m, 2H, 2×H-5), 1.96–1.61 (m, 8H, cyclopentylidene protons); $^{13}$C NMR (125 MHz, CDCl$_3$) δ121.41 (OCO), 104.53 (C-1), 85.59 (C-2), 78.76 (C-3), 76.83 (C-4), 61.07 (C-5), 36.84, 36.19 (CH$_2$CCH$_2$), 23.47, 22.80 (CH$_2$CH$_2$CCH$_2$CH$_2$); MS (CI): m/e 217(M+H$^+$).

Example 31

1,2-O-cyclopentylidene-5'-O-tosyl-D-xylofuranose (27)

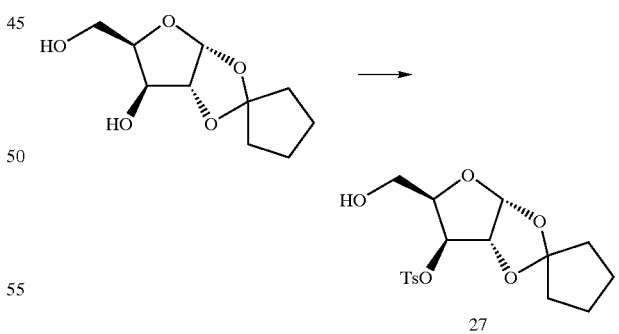

27

To a solution of 1,2-O-cyclopentylidene-D-xylofuranose (26) (0.81 mmol, 176 mg) in dry pyridine (6 ml) under nitrogen atmosphere at 0° C., p-toluenesulfonyl chloride (1.12 eq., 173 mg) was added. The reaction mixture was stirred at 0° C. for 3 hours. Then 5 ml water was added to quench the reaction, and the solvent was evaporated in high vacuum, and coevaporated with toluene twice. The mixture was dissolved in chloroform, washed with water three times and dried over MgSO₄. Removal of the solvent furnished 259 mg (27) as a white solid (86%). ¹H NMR (200 MHz, CDCl₃) δ7.80–7.32 (AA'BB', 4H, Ph), 5.84 (d, J=3.63 Hz, 1H, H-1), 4.44 (d, J=3.7 Hz, 1H, H-2), 4.42–4.29 (m, 3H, H-3, 2×H-5), 4.27–4.09 (m, 1H, H-4), 2.44 (s, 3H, CH₃), 1.89–1.61 (m, 8H, cyclopentylidene protons); ¹³C NMR (270 MHz, CDCl₃) 145.34 , 132.30, 130.06, 128.08 (aromatic), 121.86 (OCO), 104.80 (C-1), 85.15 (C-2), 77.73 (C-3), 74.41 (C-4), 66.21 (C-5), 37.02, 36.44(CH₂CCH₂), 23.54, 22.98 (CH₂CH₂CCH₂CH₂), 21.73 (CH₃); MS (CI): m/e 371 (M+H⁺).

Example 32

1,2-O-dicyclopentylidene-5'-isopropylamine-D-xylofuranose (28)

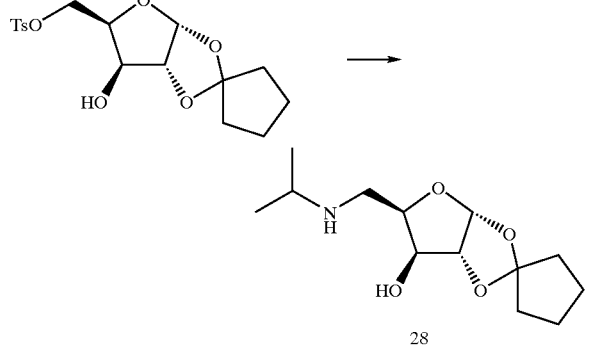

A solution of 1,2-O-cyclopentylidene-5'-tosyl-D-xylofuranose (27) (7.1 mmol, 2.64 g) in isopropylamine (15 ml) was stirred at 55° C. over night in a pressure bottle. The solvent was removed by rotary evaporator and the remaining yellow syrup was taken up with chloroform and washed with a saturated solution of sodium bicarbonate, and then with brine. The organic phase was dried over MgSO₄, the solvent was evaporated and the residue was flash chromatographed on silica gel (ethyl acetate-3% triethylamine) to furnish 1.33 g (28) as a white solid (73%), m.p.44–45° C.; [α]D²⁰=31.06 (C=2,CHCl₃); ¹H NMR (500 MHz, CDCl₃) δ8.0(bs, NH) 5.90 (d, J=3.91 Hz, 1H, H-1), 4.38 (d, J=3.91 Hz, 1H, H-2), 4.27 (d, J=2.44 Hz, 1H, H-3), 4.20 (d, J=2.93 Hz, 1H, H-4), 3.36–2.92 (ABX, 2H, 2×H-5), 2.74–2.70 (heptet, 1H, NCH), 1.95–1.63 (m, 8H, cyclopentylidene protons), 1.04–1.03 (dd, 6H, Me₂CH); ¹³C NMR (500 MHz, CDCl₃) δ121.06 (OCO), 104.82 (C-1) 86.14 (C-2), 78.30 (C-3), 77.07(C-4), 48.64(NCH), 45.90(C-5), 36.85, 36.32(CH₂CCH₂), 23.51, 22.84(CH₂CH₂CCH₂CH₂), 22.64(CH₃CHN), 22.34 (CH₃CHN); MS (CI): m/e 258([M+H⁺], 100%); HRMS(EI) m/e calc'd for C₁₃H₂₃NO₄) [M⁺]: 257.16270, found 257.1630.

Example 33

Chlorophosphoramidite (29)

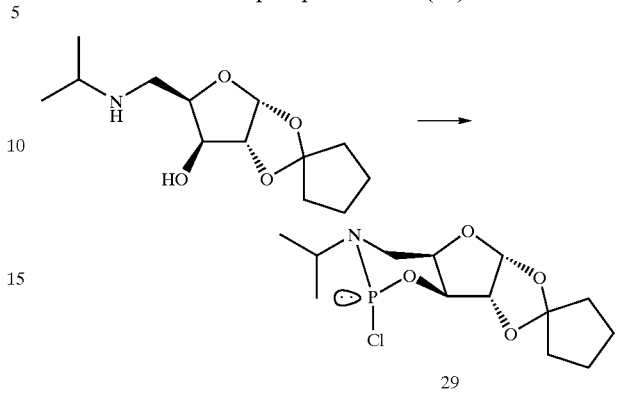

In a scrupulously dry NMR tube, 9.6 μl (0.11 mmol) phosphorus trichloride was placed via syringe, followed by 0.25 ml CDCl₃. The NMR tube was cooled at 0° C., and a solution of the 1,2-O-dicyclopentylidene-5'-isopropylamino-D-xylofuranose 28 (25.7 mg, 0.1 mmol) and triethylamine (27.8 ul, 0.22 mmol) in CDCl₃ (0.35 ml) were added under a nitrogen atmosphere with shaking of the NMR tube. An exothermic reaction was noticed. The NMR tube was then cooled to −78° C., pumped and sealed. The sealed NMR tube was heated to 40° C. and the reaction was followed by ³¹P NMR until a single peak was found in the ³¹PNMR spectrum. The product was not isolated, and was used directly in the following step. ¹H NMR (500 MHz, CDCl₃) δ5.75 (d, J=3.91 Hz, 1H, H-1), 4.51 (t, J=2.44 Hz, J=2.93 Hz, H-3), 4.37(d, J=3.91 Hz, 1H, H-2), 4.19–4.17(m, 1H, H-4), 3.42–3.34(heptet, 1H, NCH), 3.33–3.00 (ABX, 2H, 2×H-5), 1.81–1.51(m, 8H, cyclopentylidene protons), 1.05(d, J=6.84 Hz, 6H, Me₂CH); ¹³C NMR (125 MHz, CDCl₃) δ121.48 (OCO), 104.26 (C-1), 83.86, 83.83(d, J=3.66 Hz, C-2), 73.04, 72.99(d, J=6.41 Hz, C-3), 72.35(C-4), 50.42, 50.13(d, J=35.72 Hz, C-5), 36.95, 36.91(d, J=5.50 Hz, NCH), 36.62, 35.91(CH₂CCH₂), 23.22, 22.50 (CH₂CH₂CCH₂CH₂), 20.89, 20.79(d, J=12.82 Hz, CH₃CHN), 19.64, 19.60(d, J=5.50 Hz, CH₃CHN); ³¹P NMR (202 MHz, CDCl₃) δ148.42.

Example 34

5'-O-(tert-butyl dimethyl silyl)-thymidine-3'-O-Phosphoramidite

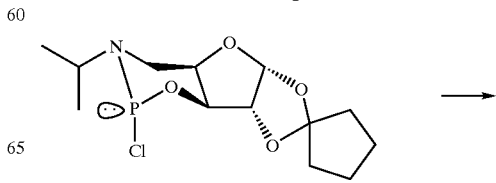

59

-continued

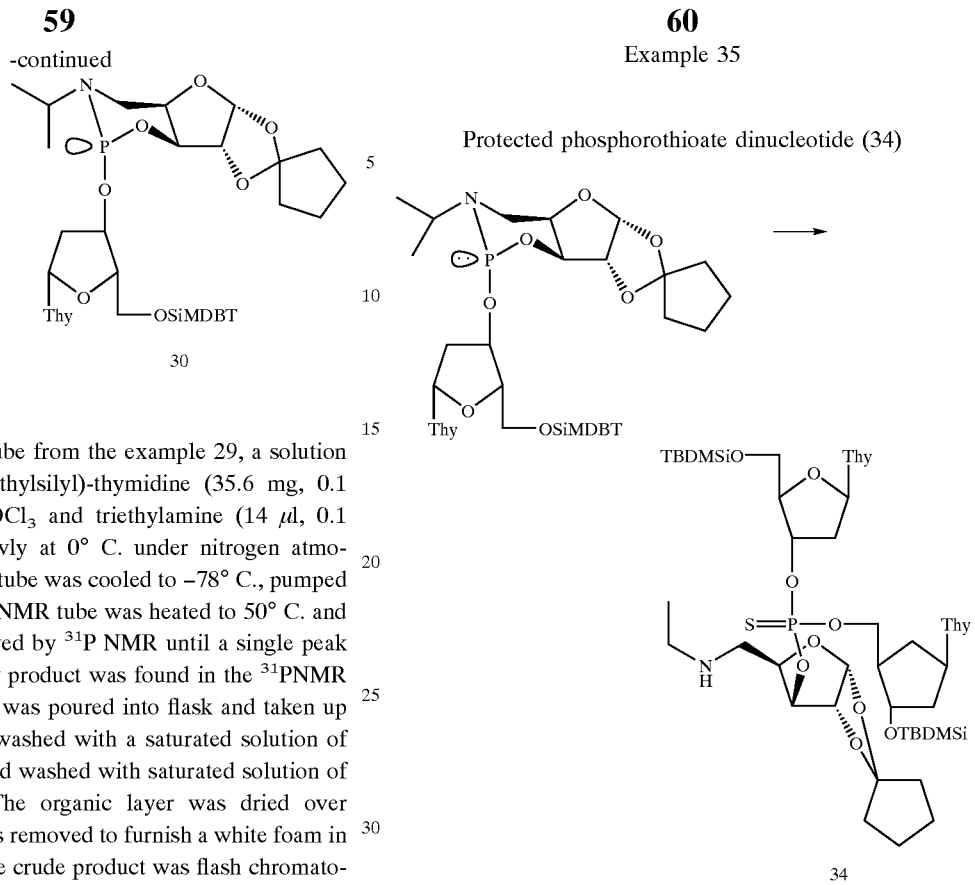

30

To the same NMR tube from the example 29, a solution of 5'-O-(tert-butyldimethylsilyl)-thymidine (35.6 mg, 0.1 mmol) in 0.45 ml CDCl$_3$ and triethylamine (14 µl, 0.1 mmol) was added slowly at 0° C. under nitrogen atmosphere. Then the NMR tube was cooled to −78° C., pumped and sealed. The sealed NMR tube was heated to 50° C. and the reaction was followed by $^{31}$P NMR until a single peak corresponding to a new product was found in the $^{31}$PNMR spectrum. The solution was poured into flask and taken up with ethyl acetate (prewashed with a saturated solution of sodium bicarbonate) and washed with saturated solution of sodium bicarbonate. The organic layer was dried over MgSO$_4$, the solvent was removed to furnish a white foam in a quantatitive yield. The crude product was flash chromatographed on a silica gel column (hexane-ethyl acetate-triethylamine=5:3:2); m.p.68–70° C.; [α]$^{20}$=62.9°(c=0.5, CHCl$_3$) $^1$H NMR (500 MHz, CDCl$_3$) δ7.98 (bs, 1H, NH), 7.46(d, J=1.00 Hz, 1H, H-6), 6.34–6.31(dd, J=5.86 Hz, J=8.30 Hz, 1H, H-1'), 5.88(d, J=3.91 Hz, 1H, H-1"), 4.56–4.53(m, 1H, H-3'), 4.41(d, J=3.91 Hz, 1H, H-2"), 4.35(m, 1H, H-3"), 4.17 (d, J=1.95 Hz, 1H, H-4"), 4.05 (d, J=1.95 Hz, 1H, H-4'), 3.89–3.76 (ABX, 2H, 2×H-5'), 3.45–3.39(m, 2H, H-5", NCH), 3.03–2.99 (m, 1H, H-5"), 2.37–2.34 (m, 1H, H-2'), 2.09–2.05(m, 1H, H-2'), 1.88(d, J=1.47 Hz, 3H, MeC=C), 1.95–1.61(m, 8H, cyclopentyl-idene protons), 1.11–1.00 (m, 6H, Me$_2$CH), 0.92(s, 9H, t-BuSi), 0.09(d, J=1.47 Hz, 6H, Me$_2$Si); $^{13}$C NMR (125 MHz, CDCl$_3$) δ163.77 (C-4), 150.35(C-2), 135.17(C-6), 121.42(OCO), 110.96(C-5), 104.59(C-1"), 86.38, 86.36(d, J=2.75 Hz, C-4'), 84.76(C-1'), 84.74(C-2"), 73.78, 73.63(d, J=19.23 Hz, C-3'), 73.07, 73.05(d, J=1.83, C-4"), 71.83, 71.80(d, J=3.66 Hz, C-3"), 63.17(C-5'), 50.09, 49.80(d, J=36.63 Hz, NCH), 40.27, 40.23 (d, J=4.58 Hz, C-2'), 36.89, 36.20(CH$_2$CCH$_2$), 36.11, 36.08(d, J=3.21 Hz, C-5"), 25.91 (SiCMe3), 23.44, 22.76(CH$_2$CH$_2$CCH$_2$CH$_2$), 22.02, 21.95 (d, J=9.16 Hz, CH$_3$CHN), 21.69, 21.64(d, J=6.41 Hz, CH$_3$CHN), 18.31(SiCMe3), 12.51(CH3C=C), −5.41, −5.48 (d, J=9.16 Hz, Me$_2$Si); $^{31}$P NMR (81 MHz, CDCl$_3$) δ130.14; MS (CI): m/e 642([M+H$^+$], 78%); EI m/e [M$^+$] 641, HRMS(EI) m/e calc'd for C$_{28}$H$_{45}$N$_3$O$_9$PSi [M$^+$—CH$_3$] 626.26625, found 626.26670, and calc'd C$_{25}$H$_{39}$N$_3$O$_9$PSi [M$^+$—C$_4$H$_9$]: 584.21930, found 584.2190. HRMS FAB (glycerol) m/e calcd. for C$_{29}$H$_{49}$N$_3$O$_9$PSi [MH$^+$] 642, 2975; found 642.2973.

60

Example 35

Protected phosphorothioate dinucleotide (34)

34

In a dried NMR tube, phosphoramidite 30 (15 mg, 0.0234 mmol), 3'-O-(tert-butyldimethylsilyl) thymidine (10 mg, 1.2 eq.) and 4,5-dicyano-2-bromo-imidazole 21 (9.17 mg, 2.0 eq.) were added. Then the NMR tube was dried in vacuum overnight. Dry acetonitile (0.6 ml) was injected into the NMR tube at 0° C. under nitrogen atmosphere. The solid dissolved instantly. The reaction was moved to room temperature and was followed by $^{31}$P NMR. Within 5 minutes, the peak corresponding to the phosphoramidite disappeared and two new peaks (143.76 ppm, 142.55 ppm=6:1) were formed. The clean $^{31}$P NMR spectrum suggested use of this product directly in the following sulphurization without isolation. To this solution, Beaucage's reagent (5.6 mg, 1.2 eq.) in 140 ul acetonitrile (0.2M) was added. Instantaneously the $^{31}$P NMR showed another two peaks (68.43 ppm, 68.23 ppm=1:6), while the peaks corresponding to the starting material disappeared. The solution in NMR tube was transfered to a flask. Then the mixture was redisolved in ethyl acetate, washed with saturated sodium bicarbonate and water, and dried over MgSO$_4$. Removal of the solvent gave 22 mg of white solid 34 (91%). The product was then purified by chromatography on a silica gel column (ethyl acetate:methanol=95:5). $^1$H NMR (500 MHz, DMSO-d6) δ7.45(s, 1H, $^3$H-6), 7.42(s, 1H, $^5$H-6), 6.19–6.15(m, 2H, $^5$H-1', $^3$H-1'), 5.86, 5.85(d, J=3.91 Hz, 1H, H-1"), 5.05–5.04 (m, 1H, $^5$H-3'), 4.78–4.77(m, 1H, H-3"), 4.60, 4.59(d, J=3.42 Hz, 1H, H-2"), 4.38–4.36((m, 1H, H-4"), 4.26–4.13

(m, 4H, $^3$H-3', 2×$^3$H-5', $^5$H-4'), 3.93, 3.91(m, 1H, $^3$H-4'), 3.81–3.73(m, 2H, 2×$^5$H-5'), 2.66–2.52(m, 3H, NCH, 2×H-5"), 2.43–2.40(m, 1H, $^5$H-2'), 2.31–2.22(m, 2H, 2×$^3$H-2'), 2.09–2.07(m, 1H, $^5$H-2'), 1.78(s,3H, $^3$CH$_3$C=C), 1.76(s, 3H, $^5$CH$_3$C=C), 1.62–1.56(m, 8H, cyclopentylidene protons), 0.94–0.89(m, 6H, Me$_2$CHN), 0.86(s, 9H, $^3$t-BuSi), 0.85(s, 9H, $^5$t-BuSi), 0.069(s, 6H, Me$_2$Si), 0.065(s, 6H, Me$_2$Si); $^{13}$CNMR (125 MHz, CDCl$_3$) δ163.97, 163.66($^5$C-4, $^3$C-4), 150.39, 150.04($^5$C-2, $^3$C-2), 135.58, 134.49($^5$C-6, $^3$C-6), 121.77(OCO), 111.26, 111.04($^5$C-5, $^3$C-5), 104.00(C-1"), 85.59, 85.56(d, J=6.41 Hz, $^5$C-4'), 85.48($^3$C-1'), 84.69 84.61, 84.39 ($^5$C-1', $^3$C-4'), 83.47(C-2"), 80.85, 80.64(d, C-3"), 80.69, 80.66(d, $^5$C-3'), 79.03, 78.97(d, $^3$C-3'), 71.49 (C-4"), 67.66, 67.52(d, J=4.58 Hz, $^3$C-5'), 63.47($^5$C-5'), 48.93(NCH), 45.23(C-5"), 40.37($^3$C-2'), 39.14, 39.09(d, J=6.41 Hz, $^5$C-2'), 37.06, 36.16(CH$_2$CCH$_2$), 25.88, 25.60 ($^5$SiCMe$_3$, $^3$SiCMe$_3$), 23.52, 22.85(CH$_2$CH$_2$CCH$_2$CH$_2$), 22.65 22.39(NCHMe$_2$), 18.28, 17.81($^5$SiCMe$_3$, 3SiCMe3), 12.51, 12.46($^5$C=CCH$_3$, $^3$C=CCH$_3$), −4.66, −4.83, −5.40, −5.46($^5$SiMe2, $^3$SiMe$_2$); $^{31}$P NMR (202 MHz, CDCl$_3$) δ68.43, 68.23 (1:6) MS (FAB): m/e 1030(M+H$^+$).

(II). 4,5-dicyano-2-bromo-imidazole 21 (7.6 mg, 2.5 eq.), phosphoramidite 30 (10 mg, 0.0156 mmol) and 3'-O-(tert-butyldimethylsilyl)thymidine (6.7 mg, 1.2 eq.) were added to a dried NMR tube. The the NMR tube was dried under vacuum overnight, and dry CDCl$_3$ (0.5 ml) was injected into the NMR tube at 0° C. under an argon atmosphere. The reaction was followed by $^{31}$P NMR until the reaction went to completion. The $^{31}$P NMR spectrum showed that the peak corresponding to the phosphoramidite at 130 ppm had disappeared, and that two new peaks appeared at 142.634, 141.880 ppm in a ratio of 40:1. MS(FAB) [M+H$^+$]: calc'd for C$_{45}$H$_{76}$N$_5$PO$_{14}$Si$_2$ phosphite triester 998, found 998.4.

Beaucage's reagent (3.8 mg, 1.2 eq.) was added directly to the solution. The $^{31}$PNMR(202 MHz, CDCl$_3$, 0° C.) instantaeously showed another two peaks at 67.831 and 67.514 ppm in the same ratio, while the peaks corresponding to the phosphite triester disappeared. The solution in the NMR tube was transfered to a flask, the solvent was evaporated, and the product was then purified by chromatography on a silica gel column (ethyl acetate:hexane:triethylamine=60:35:5) to give only one isomer. $^{31}$PNMR (202 MHz, CDCl$_3$, room temperature) δ68.291.

(III) virtually identical results were obtained when the reaction was carried out at −15° C. for 7 hours in CDCl$_3$, except that the ratio of isomers was ~68:1. MS FAB (nitrobenzyl alcohol): m/e [MH$^+$] 1030 HRMS FAB CsI m/e calcd. for C$_{45}$H$_{77}$N$_5$O$_{14}$PSSi$_2$ [MH$^+$], 1030.4464; found 1030.4460.

Example 36

Phosphorothioate dinucleotide (35)

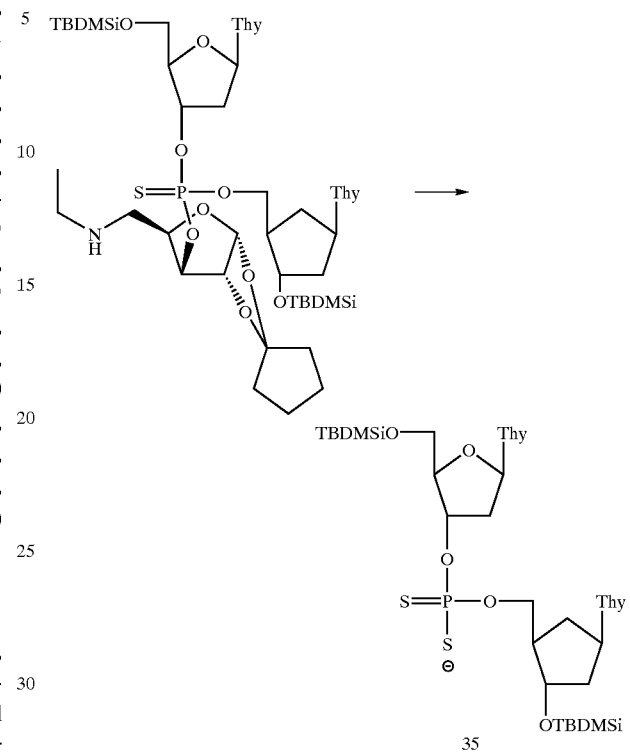

Protected phosphorothioate dinucleotide 34 (14mg, 0.0136 mmol) from Example 35 was dissolved in 1 ml 70% TFA-H$_2$O at 0° C. with stirring, and then the reaction was allowed to proceed at room temperature. The reaction was followed by TLC until the spot corresponding to the starting material disappeared. Evaporation of the solvent and coevaporation with methanol three times furnished a white solid. The crude product was purified with preparative TLC plate (0.5 mm) (CH$_2$Cl$_2$:MeOH=5:1) to give 7.2 mg of a white solid (35) (94%); $^1$H NMR (500 MHz, CD$_3$OD) δ7.87 (s, 1H, $^3$H-6), 7.85(s, 1H, $^5$H-6), 6.36–6.33(dd, J=6.35 Hz, J=7.81 Hz, 1H, $^5$H-1'), 6.30–6.27(dd, J=6.35 Hz, J=7.33 Hz $^3$H-1'), 5.06–5.03(m, 1H, $^5$H-3') 4.53–5.52(m, 1H, $^3$H-3'), 4.21–4.06(m, 4H, $^5$H-4', 2×$^3$H-5', $^3$H-4'), 3.84–3.80(m, 2H, 2×$^5$H-5'), 2.50–2.46(m, 1H), $^5$H-2'), 2.31–2.24(m, 2H, 2×$^3$H-2'), 2.21–2.17(m, 1H, $^5$H-2'), 1.96(s, 3H, $^3$CH$_3$C=C), 1.87(s, 3H, $^5$CH$_3$C=C); $^{31}$P NMR (202 MHz, CD$_3$OD) δ58.64:58.57 (6:1) MS (FAB): m/e 563 (M+H$^+$).

Example 37

1,2-O-3,5-O-dicyclopentylidene-L-xylofuranose (36)

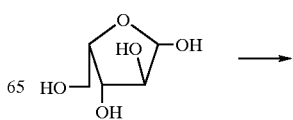

-continued

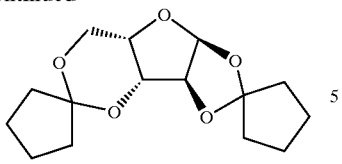

36

To a solution of trimethyl orthoformate (68 mmol, 7.5 ml) and p-toluene sulfonic acid (2 mmol, 380 mg) in dioxane (45 ml) under a nitrogen atmosphere at 0° C., was added dropwise cyclopentanone (500 mmol, 45 ml). This solution was stirred at room temperature for 2 hours and L-xylose (20 mmol, 3.0 g) was added with stirring continued overnight. Then the reaction mixture was neutralized with triethylamine. Evaporation of the solvent furnished a yellow syrupy residue. A solution of the syrupy residue in chloroform (50 ml) was washed with water (50 ml). The aqueous layer was extracted with chloroform (3×20 ml), and the combined chloroform layers were dried over (MgSO$_4$). After removing the solvent, the mixture was chromatographed on a silica gel column (hexane:ethyl acetate=5:1) to give 3.5 g white solid 36 (62%). $^1$HNMR(500 MHz, CDCl$_3$) δ5.96 (d, J=3.91 Hz, 1H, H-1), 4.42 (d, J=3.91 Hz, 1H, H-2), 4.21 (d, J=1.95 Hz, 1H, H-3), 4.09–3.98 (m, 3H, H-4, 2×H-5), 1.97–1.57 (m, 16H, cyclopentylidene protons); $^{13}$C NMR (125 MHz, CDCl$_3$) δ121.20 (C-1OCOC-2), 109.20 (C-3OCOC-5), 105.05 (C-1), 84.46 (C-2), 74.22 (C-4), 71.80 (C-3), 61.47 (C-5), 39.49, 36.80, 36.16, 29.71, 24.07, 23.47, 22.77, 22.34 (cyclopentylidene carbons); MS (CI) m/e: 283(M+H$^+$).

Example 38

112-O-cyclopentylidene-L-xylofuranose (37)

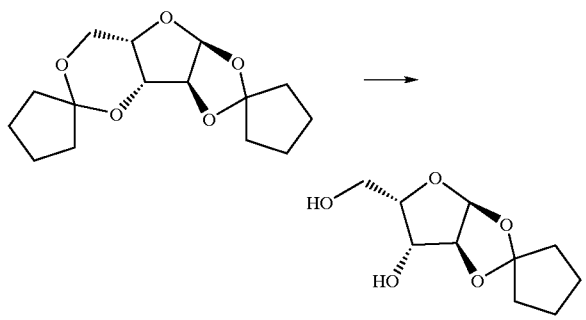

37

1,2-O-3,5-O-dicyclopentylidene-L-xylofuranose (36) (10 mmol, 2.82 g) was dissolved in acetic acid-water (2:1) (60 ml) at room temperature. The reaction mixture was stirred for 7 hours. The reaction was followed by TLC. The solvent was evaporated with high vacum, coevaporated with methanol three times, and dried in vacuo overnight to give 2.16 g white solid 37 (100%). $^1$H NMR (500 MHz, CDCl$_3$) δ5.92 (d, J=3.91 Hz, 1H, H-1), 4.42(d, J=3.91 Hz, 1H, H-2), 4.30 (d, J=2.93 Hz, 1H, H-3), 4.17–4.14 (m, 1H, H-4), 4.07–3.97 (m, 2H, 2×H-5), 1.96–1.60 (m, 8H, cyclopentylidene protons); $^{13}$C NMR (125 MHz, CDCl$_3$) δ121.42 (OCO), 104.52 (C-1), 85.56 (C-2), 78.81 (C-3), 76.77 (C-4), 61.01 (C-5), 36.84, 36.19 (CH$_2$CCH$_2$), 23.47, 22.79 (CH$_2$CH$_2$CCH$_2$CH$_2$); MS (CI): m/e 217(M+H$^+$).

Example 39

1,2-O-cyclopentylidene-5'-O-tosyl-L-xylofuranose (38)

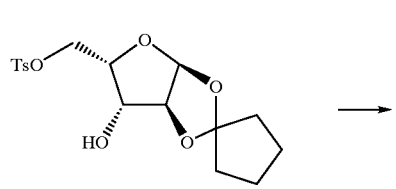

38

To a solution of 1,2-O-cyclopentylidene-L-xylofuranose (37) (9.4 mmol, 2.03 g) in dry pyridine (25 ml) under nitrogen atmosphere at 0° C., p-toluenesulfonyl chloride (1.2 eq., 2.15 g) was added. The reaction mixture was stirred at 0° C. for 12 hours. Then 10ml water was added to quench the reaction, and the solvent evaporated in high vacum, and coevaporated with toluene twice. The mixture was dissolved in chloroform, washed with water three times and dried over MgSO$_4$. Removal of the solvent furnished 2.96 g of 38 as a white solid (85%). $^1$H NMR (500 MHz, CDCl$_3$) δ7.78–7.32 (AA'BB', 4H, Ph), 5.83 (d, J=3.42 Hz, 1H, H-1), 4.42 (d, J=3.91 Hz, 1H, H-2), 4.42–4.24 (m, 3H, H-3, 2×H-5), 4.16–4.08 (m, 1H, H-4), 2.42 (s, 3H, CH$_3$), 1.90–1.63 (m, 8H, cyclopentylidene protons); $^{13}$C NMR (270 MHz, CDCl$_3$) δ145.25, 130.26, 130.09, 130.01, 129.96 (aromatic), 121.71 (OCO), 104.69 (C-1), 85.04 (C-2), 77.67 (C-4), 74.25 (C-3), 66.39 (C-5), 36.89, 36.30(CH$_2$CCH$_2$), 23.42, 22.85 (CH$_2$CH$_2$CCH$_2$CH$_2$), 21.63 (CH$_3$); MS (CI): m/e 371 (M+H$^+$).

Example 40

1,2-O-dicyclopentylidene-5'-isopropylamine-L-xylofuranose (39)

-continued

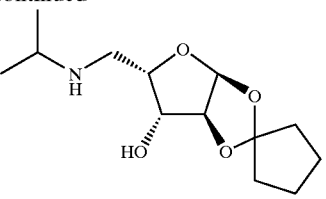

39

A solution of 1,2-O-cyclopentylidene-5'-tosyl-L-xylofuranose (38) (7.0 mmol, 2.6 g) in isopropylamine (15 ml) was stirred at 55° C. overnight in a pressure bottle. The solvent was removed by rotary evaporator and the remaining yellow syrup was taken up with chloroform and washed with a saturated solution of sodium bicarbonate and with brine. The organic phase was dried over $MgSO_4$, the solvent was evaporated and the residue was flash chromatographed on silica gel (ethyl acetate-3% triethylamine) to furnish 1.30 g white solid 39 (72%). m.p. 39–41° C.; $[\alpha]_D^2 = -31.37(c=2, CHCl_3)$; $^1H$ NMR (500 MHz, $CDCl_3$) δ8.0(bs, NH), 5.88 (d, J=3.91 Hz, 1H, H-1), 4.37 (d, J=3.91 Hz, 1H, H-2), 4.25 (d, J=2.93 Hz, 1H, H-3), 4.19 (m, 1H, H-4), 3.34–2.91 (ABX, 2H, 2×H-5), 2.73–2.71 (heptet, 1H, NCH), 1.92–1.61 (m, 8H, cyclopentylidene protons), 1.03–1.01(dd, J=2.44 Hz, J=6.35 Hz, 6H, $Me_2CH$); $^{13}C$ NMR (500 MHz, $CDCl_3$) δ121.00 (OCO), 104.75 (C-1), 86.06 (C-2), 78.20 (C-3), 77.00(C-4), 48.62(NCH), 45.82(C-5), 36.78, 36.25 ($CH_2CCH_2$), 23.46, 22.78($CH_2CH_2CCH_2CH_2$), 22.57 ($CH_3CHN$), 22.27($CH_3CHN$); MS (CI): m/e 258([M+H$^+$]; 100%); HRMS(EI) m/e calc'd for $C_{13}H_{23}NO_4$ [M$^+$]: 257.16270, found 257.16250.

Example 41

Chlorophosphoramidite (40)

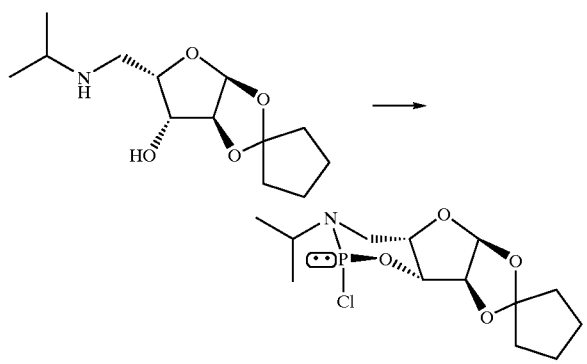

In a scrupulously dry NMR tube, 9.6 μl (0.11 mmol) phorsphorus trichloride was added via syringe, then 0.25 ml $CDCl_3$ was similarly added. This NMR tube was cooled to 0° C., and a solution of the 1,2-O-dicyclopentylidene-5'-isopropylamine-L-xylofuranose (17) (25.7 mg, 0.1 mmol) and triethylamine (27.8 ul, 0.22 mmol) in $CDCl_3$ (0.35 ml) was added under a nitrogen atmosphere with shaking of the NMR tube. An exothermic reaction was noticed. The NMR tube was then cooled to −78° C., pumped and sealed. The sealed NMR tube was heated to 40° C. and the reaction was followed by $^{31}PNMR$ until a single peak was found in the $^{31}PNMR$ spectrum. The product was not isolated, and was directly used in the following step. $^{31}P$ NMR (300 MHz, CDCl3) δ148.75

Example 42

5'-O-(tert-butyl dimethyl silyl)-thymidine-3'-O-Phosphoramidite (41)

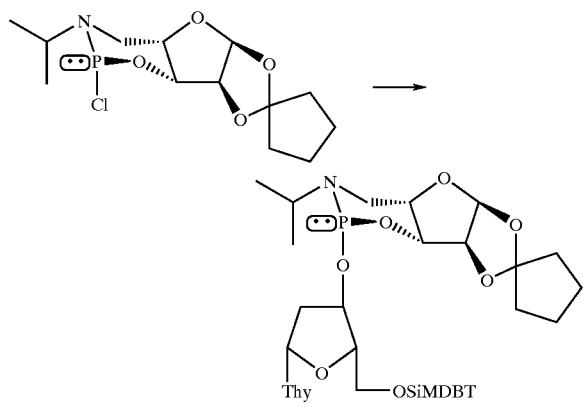

41

To the same NMR tube from previous Example 41, a solution of 5'-O-(tert-butyl dimethyl silyl)-thymidine (35.6 mg, 0.1 mmol) in 0.45 ml $CDCl_3$ and triethylamine (14 μl, 0.11 mmol) was added slowly at 0° C. under a nitrogen atmosphere. Then the NMR tube was cooled to −78° C., pumped and sealed. The sealed NMR tube was heated to 50° C. and the reaction was followed by $^{31}PNMR$ until a single peak corresponding to a new product was found in the $^{31}PNMR$ spectrum. The solution was poured into a flask, and taken up with ethyl acetate (prewashed with a saturated solution of sodium bicarbonate) and washed with saturated solution of sodium bicarbonate. The organic layer was dried over $MgSO_4$, and the solvent was removed to furnish a white foam in a quantatitive yield. The crude product was flash chromatographyed on a silica gel column (hexane-ethyl acetate-triethylamine=5:3:2) to furnish white crystals (41); m.p. 99–101° C.; $[\alpha]_D^{20}$ −72.0° (c=0.5,$CHCl_3$) $^1H$ NMR (500 MHz, $CDCl_3$) δ8.77 (bs, 1H, NH), 7.46(s, 1H, H-6), 6.33–6.30(dd, J=5.86 Hz, J=7.81 Hz, 1H, H-1'), 5.88(d, J=3.91 Hz, 1H, H-1"), 4.56–4.53(m, 1H, H-3'), 4.43(d, J=3.42 Hz, 1H, H-2"), 4.35(m, 1H, H-3"), 4.18 (d, J=1.95 Hz, 1H, H-4"), 4.05 (m, 1H, H-4'), 3.90–3.76 (ABX, 2H, 2×H-5'), 3.45–3.42(m, 2H, H-5", NCH), 3.03–2.99 (m, 1H, H-5"), 2.38–2.35 (m, 1H, H-2'), 2.12–2.06(m, 1H, H-2'), 1.89(s, 3H, MeC=C), 1.96–1.62(m, 8H, cyclopentylidene protons), 1.11–1.08 (m, 6H, $Me_2CH$), 0.90(s, 9H, t-BuSi), 0.09, (d, J=1.95 Hz, 6H, $Me_2Si$); $^{13}C$ NMR (125 MHz, $CDCl_3$) δ163.74 (C-4), 150.31(C-2), 135.18(C-6), 121.44 (OCO), 110.93(C-5), 104.59(C-1"), 86.61, 86.57(d, J=5.49 Hz, C-4'), 84.75, 84.73(d, J=2.75 Hz, C-1'), 84.70(C-2"), 73.07, 73.05(d, J=1.83 Hz, C-3'), 73.03, 72.89(d, J=17.4, C-4"), 71.82, 71.78(d, J=4.58Hz, C-3"), 62.98(C-5'), 50.05, 49.76(d, J=36.63 Hz, NCH), 39.94, 39.92(d, J=2.75Hz, C-2'), 36.86, 36.19($CH_2CCH_2$), 36.11, 36.08(d, J=3.06 Hz, C-5"), 25.92(SiCMe3), 23.45, 22.76($CH_2CH_2CCH_2CH_2$), 21.99, 21.91(d, J=9.16 Hz, CH₃CHN), 21.69, 21.64(d, J=6.41 Hz, CH₃CHN), 18.35(SiCMe3), 12.52(CH3C=C), −5.39, −5.45 (d, J=9.16 Hz, Me₂Si); ³¹P NMR (81 MHz, CDCl₃) δ129.34; MS (CI): m/e 642(M+H⁺). EI: m/e 641 [M+]. MS FAB (nitrobenzyl alchol): m/e [MH⁺] 642, HRMS FAB (glcerol) m/e calcd. for C₂₉H₄₉N₃O₉ PSi [MH⁺] 642.2975; found 642.2973.

Example 43

Protected phosphorothioate dinucleotide (42)

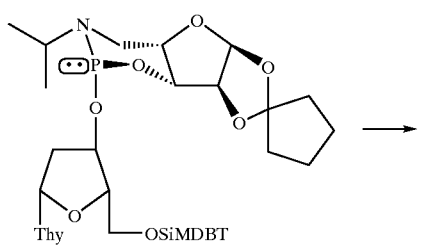

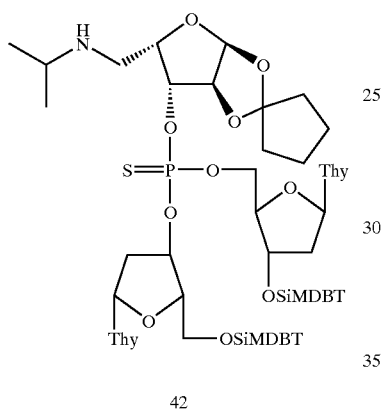

42

I: In a dried NMR tube, phosophoramidite 41 (15 mg, 0.0234 mmol), 3'-O-(tert-butyldimethylsilyl)thymidine (10 mg, 1.2 eq.) and 4,5-dicyano-2-bromo-imidazole 21 (9.17 mg, 2.0 eq.) were added. Then the NMR tube was dried in vacuum overnight. Dry acetonitile (0.6 ml) was injected into the NMR tube at room temperature under a nitrogen atmosphere. The solid dissolved instantly. The reaction was followed by ³¹PNMR. Within 5 minutes, the peak corresponding to the phosphoramidite disappeared. To this solution, Beaucage's reagent (5.6 mg, 1.2 eq.) in 140 μl acetonitrile (0.2M) was added. The peaks corresponding to the starting material disappeared. The solution in NMR tube was transfered to a flask, and the solvent evaporated. Then the mixture was redisolved in ethyl acetate, washed with saturated sodium bicarbonate and water, and dried over MgSO₄. After removal of the solvent, the product was purified by chromatography on a silica gel column (ethyl acetate:methanol=95:5) to furnish 42 in a diastereomeric ratio of 7:1(69.12, 68.91 ppm). ¹H NMR (500 MHz, CDCl₃) δ7.46(s, 1H, ³H-6), 7.27(s, 1H, ⁵H-6), 6.34–6.10(m, 2H, 5H-1', ³H-1'), 5.86, 5.87(d, J=3.42 Hz, 1H, H-1"), 5.17–5.14 (m, 1H, ⁵H-3'), 4.83–4.81(d, J=10.25 Hz,1H, H-3"), 4.56, 4.55(d, J=3.91 Hz, 1H, H-2"), 4.38(m, 2H, ³H-3', H-4"), 4.25–4.21(m, 3H, 2×³H-5', ⁵H-4'), 3.98(m, 1H, ³H-4'), 3.91–3.85(m, 2H, 2×⁵H-5'), 2.85, 2.84(d, J=6.35 Hz, 1H, 2×H-5"), 2.81(m, 1H, NCH), 2.52–2.47(dd, 2H, ⁵H-2'), 2.25–2.23(m, 2H, 2×³H-2'), 2.08–2.02(m, 1H, ⁵H-2'), 1.91 (s,3H, ⁵CH₃C=C), 1.89(s, 3H, ³CH₃C=C), 1.92–1.65(m, 8H, cyclopentylidene protons), 1.05, 1.04(d, J=5.86 Hz, 6H, Me₂CHN), 0.90(s, 9H, ³t-BuSi), 0.86(s, 9H, ⁵t-BuSi), 0.11 (s, 6H, Me₂Si), 0.05(s, 6H, Me₂Si); ¹³CNMR (125 MHz, CDCl₃) δ163.80, 163.59(⁵C-4, ³C-4), 150.33, 150.15(⁵C-2, ³C-2), 136.13, 134.64(⁵C-6, ³C-6), 122.03(OCO), 111.43, 111.11(⁵C-5, ³C-5), 104.28(C-1"), 86.29(³C-1'), 85.95, 85.90(d, J=6.41 Hz, ⁵C-4'), 84.80 84.72, 84.69 (⁵C-1', ³C-4'), 83.59(C-2"), 80.85, 80.81(d, J=4.58 Hz, C-3"), 80.69, 80.66 (d, J=4.58 Hz, ⁵C-3'), 79.03, 78.97(d, J=8.24 Hz, ³C-3'), 71.30(C-4"), 67.38, 67.34(d, J=5.50 Hz, ³C-5'), 63.37(⁵C-5'), 48.91(NCH), 45.18(C-5"), 40.35(³C-2'), 39.12, 39.09(d, J=3.66 Hz, 5C-2'), 37.14, 36.23(CH₂CCH₂), 25.88, 25.65 (⁵SiCMe₃, ³SiCMe₃), 23.55, 22.89(CH₂CH₂CCH₂CH₂), 22.80, 22.55(NCHMe₂), 18.28, 17.86(⁵SiCMe₃, 3SiCMe₃), 12.52, 12.49(⁵C=CCH₃, ³C=CCH₃), −4.66, −4.83, 31 5.40, −5.46(⁵SiMe2, ³SiMe₂); ³¹P NMR (121 MHz, CDCl₃) δ69.12, 68.91 (7:1); MS (FAB): m/e (M+H⁺).

Example 44

Phosphorothioate dinucleotide (43)

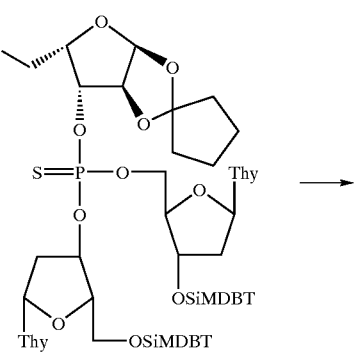

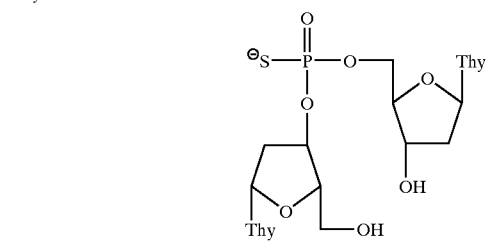

43

The protected phosphorothioate dinucleotide 42 obtained from example 43-I (15 mg, 0.014 mmol) was dissolved in 1 ml 70% TFA-H₂O at 0° C. with stirring and, the reaction was allowed to proceed at room temperature. The reaction was followed by TLC until the spot corresponding to the starting material disappeared. Evaporation of the solvent and coevaporation with methanol three times furnished a white solid. The crude product was purified with preparative TLC plate (0.5 mm) (CH₂Cl₂:MeOH=5:1) to give 43 as a white solid: ¹H NMR (500 MHz, CD₃OD) δ7.91 (s, 1H, ³H-6), 7.86(s, 1H, ⁵H-6), 6.36–6.33(dd, J=6.35 Hz, J=7.81 Hz, 1H, ⁵H-1'), 6.29–6.26(dd, J=5.86 Hz, J=7.81 Hz ³H-1'), 5.08–5.05(m, 1H, ⁵H-3') 4.52–5.51(m, 1H, ³H-3'),4.21(m, 1H, ⁵H-4'), 4.14–4.11(m, 2H, 2×³H-5'), 4.04 (m, 1H, ³H-4'), 3.86–3.79(m, 2H, 2×$^5$H-5'), 2.48–2.44(m, 1H, $^3$H-2'), 2.31–2.24(m, 2H, 2×$^5$H-2'), 2.23–2.16(m, 1H, $^3$H-2'), 1.97 (s, 3H, $^3$CH$_3$C=C), 1.87(s, 3H, $^5$CH$_3$C=C); $^{31}$P NMR (121 MHz, CDCl$_3$) δ59.14: 59.08(1:7); MS (FAB): m/e (M+H$^+$)

Example 45

Synthesis of γ-aminoalcohol 44 (Scheme 1)

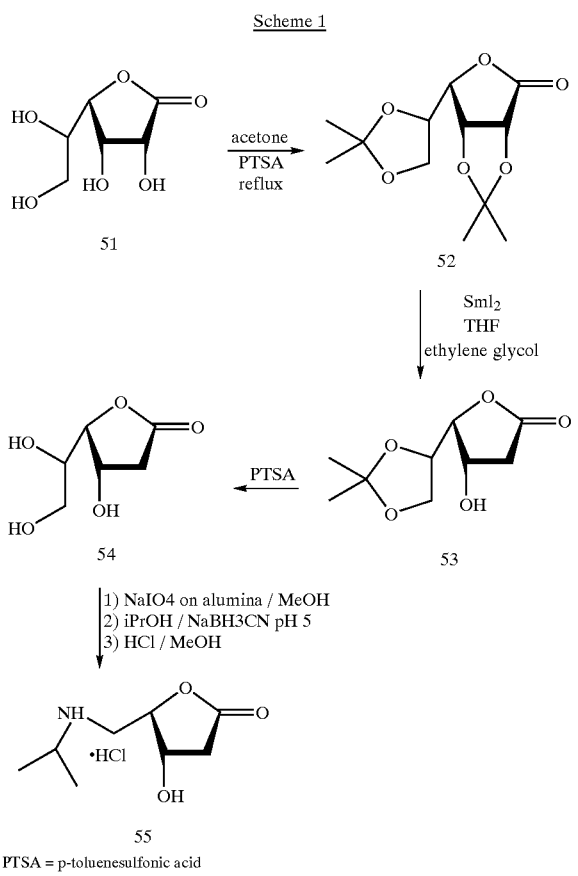

PTSA = p-toluenesulfonic acid

The synthesis of amino-alcohol 44 is shown in Scheme 1 below:

Starting from L-mannonic-γ-lactone 51, both diols are protected by conversion to their acetonides according to standard procedures, using acetone with para-toluenesulfonic acid as a catalyst, to yield bis-acetonide lactone 52.

The bis-acetonide is then reacted in presence of samarium iodide in a mixture of THF and ethylene glycol at room temperature according to the procedure described by Christian Girard, Ph.D. Thesis, Universite de Montreal, 1995. This reaction proceeds with high yield and high regioselectivity and affects the acetonide located on the a-position to the ester, yielding β-hydroxyester 53.

The next step is a classical acid-catalyzed deprotection of the acetonide to give triol product 54. The diol function of the triol is then cleaved by sodium periodate on alumina in methanol. The intermediate aldehyde undergoes a reductive amination in presence of isopropylamine and sodium cyanoborohydride to yield γ-aminoalcohol 55, which is isolated and stabilized as the hydrochloride salt. See Robert Hambalek, Ph.D. Thesis, McGill University, 1992.

γ-aminoalcohol 55 is then employed as a chiral precursor to the stereocontrolled synthesis of a P-chiral phosphorothioate dimer that can be deprotected by a base-catalyzed β-elimination. An example of this type of elimination is found in Takahata et al., *J. Org. Chem.* 1995, 60, 5628–5633.

Preparation of Indole Containing Chiral Auxiliaries

Example 46

Preparation of (S)-1-(indol-2-yl)-propan-2-ol (S)-1-(indol-2-yl)-propan-2-ol was prepared according to the following Scheme:

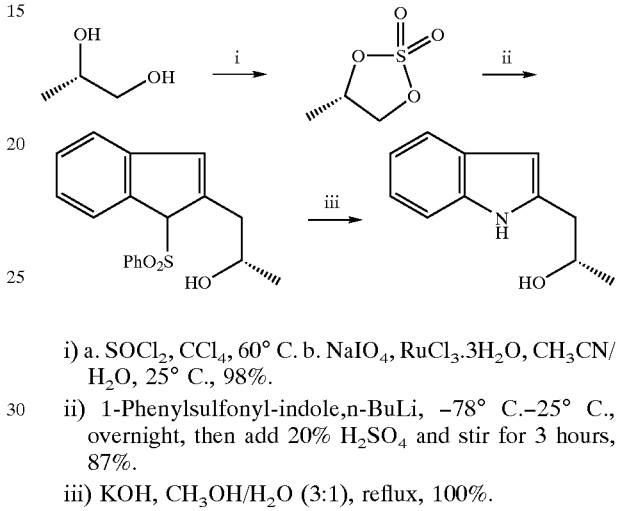

i) a. SOCl$_2$, CCl$_4$, 60° C. b. NaIO$_4$, RuCl$_3$.3H$_2$O, CH$_3$CN/H$_2$O, 25° C., 98%.

ii) 1-Phenylsulfonyl-indole,n-BuLi, −78° C.-25° C., overnight, then add 20% H$_2$SO$_4$ and stir for 3 hours, 87%.

iii) KOH, CH$_3$OH/H$_2$O (3:1), reflux, 100%.

Example 46A

Preparation of 1-Phenylsulfonyl-indole (60)

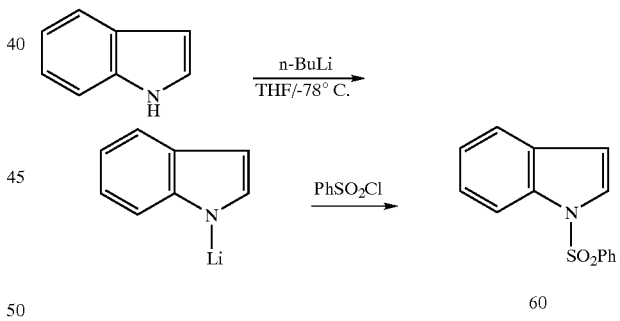

To a solution of indole (2.4 g, 20 mol) in dry THF (20 ml) under argon at −78° C. was added dropwise via syringe over 10 min n-butyllithium (1.6M in hexanes; 14 ml). The cooling bath was removed and the solution was stirred for 1 h while warming to 0° C. The resulting indole anion precipitated as a very fine white solid in a cloudy colorless solution. After the suspension was recooled to −78° C., benzenesulfonyl chloride (2.8 ml, 22 mmol) was added via syringe over 20 min, keeping the temperature below −60° C. The resulting colorless mixture was allowed to warm slowly to room temperature overnight, poured into 2% aqueous sodium bicarbonate (30 ml), and extracted with ethyl acetate (2×25 ml). The combined extracts were washed with 2% aqueous sodium bicarbonate(30 ml), water (2×25 ml), dried over anhydrous sodium sulphate, and evaporated to give a light amber oil which crystallized when triturated with 2:1 hexane/ether (15 ml). After standing in the cold (−20° C.) for several hours, the product was collected by filtration, washed with hexane, and dried in vancum to provide pure 1-phenylsulfonyl-indole (60) as white crystals (4.8 g, 90.6%).

$^1$H NMR (270 MHz, CDCl$_3$): δ7.16–7.98 (m, 9H, C$_6$H$_5$, C$_6$H$_4$), 7.63(d, $^3$J=3.7, 1H, NCH), 6.71(d, $^3$J=3.7, 1H, NCHCH). $^{13}$C NMR (67.9 MHz, CDCl$_3$): δ138.3, 134.9, 133.8, 130.8, 129.3, 126.8, 126.3, 124.7, 123.4, 121.5, 113.6, 109.3. m.p. 73.0–73.5° C.

Example 46B (S)-1,2-propandiol cyclic sulfate (61)

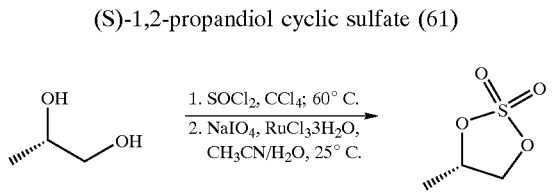

A 100-ml, two-neck round-bottom flask equipped with a reflux condenser and topped with a CaCl$_2$ drying tube connected to an HCl trap, and a rubber septum was charged with (S)-1,2-propanediol (2.3 g, 40 mmol) and CCl$_4$ (20 ml). Thionyl chloride (4 ml, 54.8 mmol) was added via a syringe to the flask, and the resulting solution was refluxed for 30 min. The solution was then cooled with an ice-water bath and diluted with CH$_3$CN (20 ml). RuCl$_3$.3H$_2$O (7.8 mg, 0.03 mmol) and NaIO$_4$ (12 g, 56 mmol) were added followed by water (40 ml). The resulting mixture was stirred at room temperature for 60 min. The mixture was then diluted with ethyl acetate (150 ml), and the two phases were separated. The organic layer was washed with water (30 ml), saturated sodium bicarbonate solution (2×20 ml), and brine (20 ml). After drying over anhydrous sodium sulfate, the solution was filtered through a small pad of silica gel to remove the brown color. The filtrate was then concentrated to afford (S)-1,2-propanediol cyclic sulfate (61) as a colorless liquid (4.0 g, 98%).

$^1$H NMR (270 MHz, CDCl$_3$): δ5.10 (ddq, $^3$J$_{CH2-H}$=8.2 Hz, 6.0 Hz, $^3$J$_{CH3-H}$=6.2 Hz, 1H, CH), 4.72 (dd, $^2$J=8.7 Hz, $^3$J=6.0 Hz, 1H, CHH'), 4.28 (dd, $^2$J=8.7 Hz, $^3$J=8.2 Hz, 1H, CHH'), 1.55 (d, $^3$J=6.2 Hz, 3H, CH3). $^{13}$C NMR (67.9 MHz, CDCl$_3$): δ80.0, 74.3, 17.7.

Example 46C (S)-2-Indolylisopropanol (62)

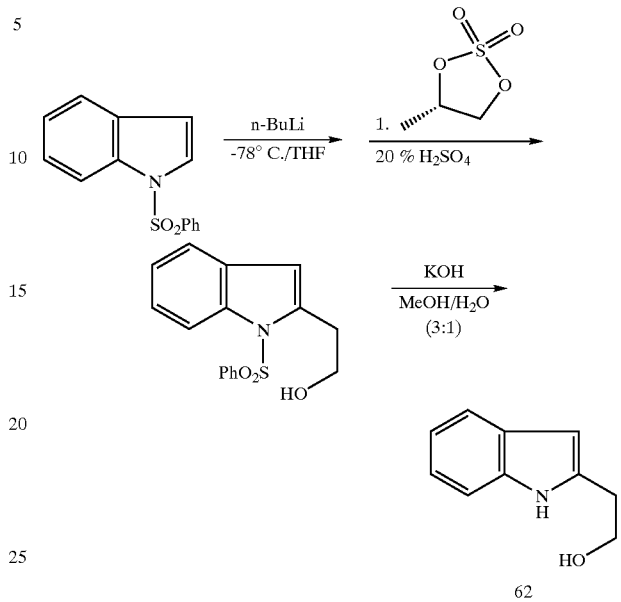

To a solution of 1-phenylsulfonyl-indole (2.57 g, 10 mmol) in dry THF (30 ml) under argon at −78° C. was added dropwise via syringe over 10 min a solution of 1.6 M butyllithium (6.25 ml, 10 mmol). The mixture was stirred for 1.5 h below −70° C. and then allowed to warm slowly to 5° C. over 1h. The solution was cooled to −78° C. and then treated via syringe with a solution of (S)-1,2-propanediol cyclic sulfate (1.5 g, 10.8 mmol) in dry THF (10 ml). The mixture was allowed to warm slowly to room temperature overnight, poured into 20% sulfuric acid (100 ml) and stirred for 3 hrs. The solution was extracted with ethyl acetate (3×50 ml). The combined extracts were washed with H$_2$O (2×100 ml), saturated sodium bicarbonate solution (2×100 ml) and brine (2×100 ml), dried over anhydrous sodium sulphate, and rotary evaporated to afford a light amber oil. This oil was crystallized in ether:hexane (1:1) to provide (S)-1-phenylsulfonyl-2-indolylisopropanol as white crystals (2.85 g, 90%).

$^1$H NMR (270 MHz, CDCl$_3$): δ7.17–8.16 (m, 9H, C$_6$H$_5$, C$_6$H$_4$), 6.51 (d, $^4$J=0.76, 1H, NCCH), 4.26 (m, 1H, CHO), 3.25, 3.01 (m, 2H, CHH'), 1.91 (s, br, 1H, OH), 1.30 (d, $^3$J=6.2 Hz, 3H, CH$_3$). $^{13}$C NMR (67.9 MHz, CDCl$_3$): δ138.8, 138.5, 137.4, 133.8, 129.7, 129.3, 126.3, 124.4, 123.9, 120.5, 115.1, 111.6, 67.2, 39.1, 23.1. m.p.: 88–89° C.

Cleavage of the phenylsulfonyl protecting group was achieved with potassium hydroxide. 2.85 g (S)-1-phenylsulfonyl-2-indolylisopropanol was dissolved in 50 ml methanol/water (3:1) containing 1.5 g KOH. The solution was refluxed for 5 hours and extracted with ethyl acetate (2×50 ml). The combined extracts were washed with H$_2$O (2×100 ml) and brine (2×100 ml), dried over anhydrous sodium sulphate, and evaporated to afford pure (S)-2-indolylisopropanol (1.65 g, 95%) as a light amber oil.

$^1$H NMR (270 MHz, CDCl$_3$): δ8.51 (s, 1H, NH), 7.58–7.05 (m, 4H, C$_6$H$_4$), 6.28 (m, 1H, NCCH), 4.10 (m,

1H, CHO), 2.93, 2.76 (m, 2H, CHH'), 2.06 (s, br, 1H, OH), 1.25 (d, $^3J$=6.2 Hz, 3H, $CH_3$). $^{13}C$ NMR (67.9 MHz, $CDCl_3$): δ136.6, 136.2, 128.9, 121.3, 119.9, 119.7, 110.7, 100.9, 68.0, 37.5, 23.3.

Example 47

Preparation of Indole Oxazaphosphorine

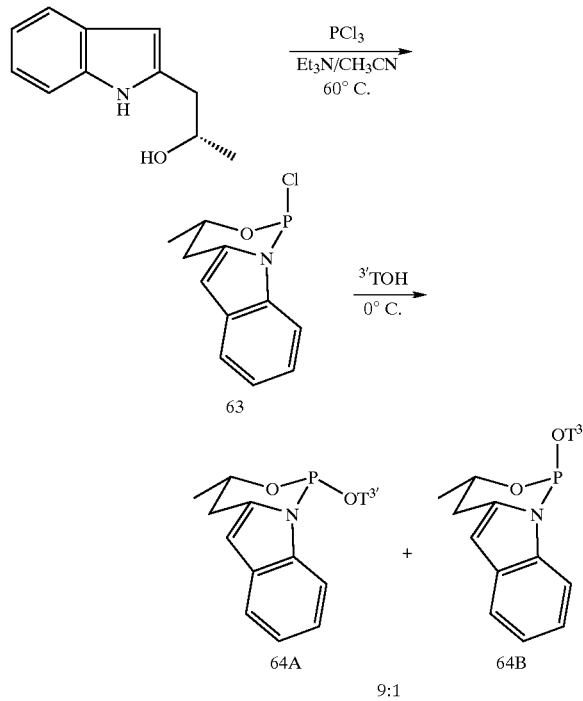

$^{3'}$TOH = 5-O'-tBDMS-thymidine

In a scupulously dried 25-ml round-bottom flask was added 10 ml dried $CH_3CN$, flushed with argon and sealed with a septum. $PCl_3$ (100 μl, 1.15 mmol) was syringed into the flask. Then the flask was cooled to –0° C., and a solution of (S)-2-indolisopropanol (200 mg, 1.15 mmol) in $CH_3CN$ (0.35 ml) containing triethylamine (525 μl, 3.8 mmol) was syringed into the flask. As soon as (S)-2-indolisopropanol was introduced, a thick white precipitate was observed, corresponding to the formation of triethylammonium chloride. After stirred for 30 min at 0° C., the reaction mixture was warmed to 60° C. The warming was continued until the $^{31}P$ NMR showed a major peak at δ144 ppm (about one day). The flask was cooled to 0° C. again, and a solution of 5'-O-tBDMS-thymidine (410 mg, 1.15 mmol) in $CH_2Cl_2$ (0.4 ml) was added. The reaction mixture was stirred at 0° C. for 30 min. Triethylammonium chloride was filtered out and washed with $CH_2Cl_2$ (2×10 ml). The filtration was concentrated and purified by silica gel chromatography ($CH_2Cl_2/CH_3CN$ 1:10) to afford indol oxazaphosphorine (346 mg, 54%) as a white solid. Two diastereoisomers of indol oxazaphosphorine were obtained (64A and 64B), in the ratio of 9:1 (read from $^{31}P$ NMR). The following NMR spectra were assigned for the major component:

$^{31}P$ NMR (202.3 MHz, $CDCl_3$): δ121.56 (12.4%), 120.67 (87.6%). $^1H$ NMR (500 MHz, $CDCl_3$, assigned by COSY): δ8.81 (br s, 1H, NH), 7.39 (s, 1H, H-6), 7.54, 7.17 (m, 4H, $C_6H_4$), 6.36 (dd, 1H, $^3J$=9.0 Hz, $^3J$=5.5 Hz, H-1'), 6.33 (s, 1H, C=CH—Ph), 4.72 (m, 1H, H-3'), 4.41 (m, 1H, CHOP), 3.94 (m, 1H, H-4'), 3.58 (m, 1H, H-5'), 3.06–3.10 (m, 3H, H-5", $CH_2$), 2.36 (m, 1H, H-2'), 1.97 (m, 1H, H-2"), 1.87 (s, 3H, $CH_3$C-5), 1.48 (d, 3H, $^3J$=5.5 Hz, $CH_3$), 0.84 (s, 9H, $SiC(CH_3)_3$), –0.05 (d, 6H, $Si(CH_3)_2$). $^{13}C$ NMR (67.9 MHz, $CDCl_3$): δ163.7 (C-4), 150.3 (C-2), 137.6, 129.8, 122.2, 121.5, 120.4, 111.1 ($C_6H_4$), 136.4 (CCHPh), 135.2 (C-6), 110.6 (C-5), 103.2 (CCHPh), 86.2 (C-4'), 86.1 (CHOP), 84.8 (C-1'), 73.7 (C-3'), 71.5 (C-5'), 62.9 (C-2'), 26.0 (CH2), 25.9 ($SiC(CH_3)_3$), 23.0 ($SiC(CH_3)_3$), 18.3 ($CH_3$), 12.6 ($CH_3$C-5), –5.54, –5.77 ($CH_3SiCH_3$). HRMS (FAB, M+H): Cal. 560.234578, found 560.234590). m. p. 80–82° C.

Preparation of Dinucleotide Phosphorothioate Triester

Dinucleotide phosphorothioate triester compounds were prepared according to the following scheme:

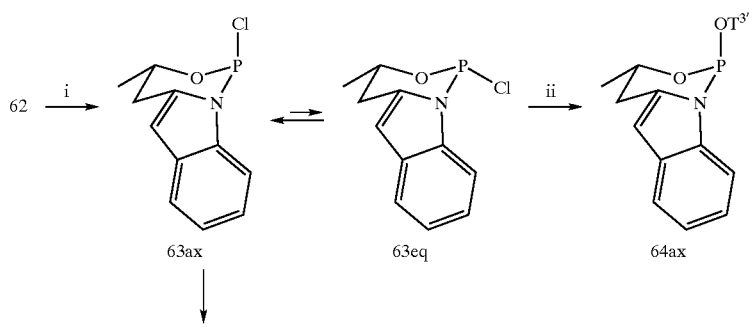

-continued

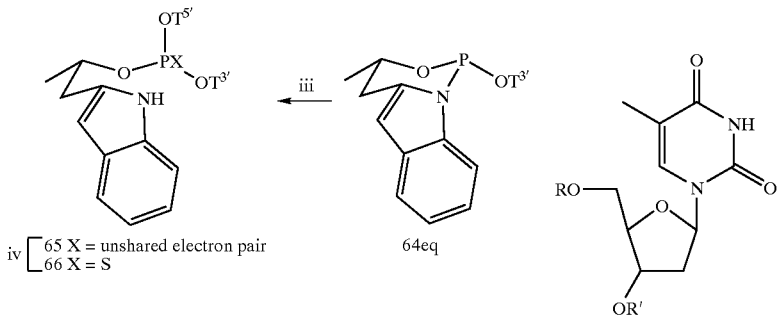

iv ⌈ 65 X = unshared electron pair
   ⌊ 66 X = S

64eq

T³'OH:R = TBDMS, R' = H
T⁵'OH:R' = TBDMS, R = H i) PCl₃, CH₃CN/Et₃N, 0° C.–60° C.
ii) T³OH
iii) T⁵OH, DBU.
iv) Beaucage's reagent.

Equimolar acetonitrile solutions of 62 and PCl₃ were allowed to react at 0° C. under argon and the reaction was followed by $^{31}P$ NMR. After a few minutes, the total disappearance of the peak corresponding to PCl₃ at 221 ppm was observed, and several peaks appeared around 140–150 ppm. The mixture was warmed up to 60° C. The warming was continued (about 10 hours) until the $^{31}P$ NMR showed a major peak at 144 ppm, which indicated the formation of phosphorochloridite 63, which is believed to exist as a rapidly equilibrating mixture of 63ax and 63eq, in which 63ax predominates. The mixture was cooled to 0° C. and a solution of 5'-O-tBDMS-thymidine in CH₂Cl₂ was added. Two peaks were observed within 0.5 h, a major one at 120.47 ppm and a minor one at 120.36 ppm, corresponding to the formation of the two diastereoisomers 64eq and 64ax. The ratio of two diastereoisomers of 3 was affected by the temperature at which 5'-O-tBDMS-thymidine was added. At 20–60° C., the ratio was 7:1; at lower temperature (0–78° C.), the ratio increased to 9:1.

The coupling of 64ax and 64eq with 3'-O-tBDPS-thymidine was done in the presence of 1,8-diazabicyclo[5,4,0]undec-7-ene (DBU). The major diastereoisomer 64eq reacted much faster with 3'-O-tBDPS-thymidine than the minor axially substituted isomer 64ax. By using 1 eq. of DBU and 1 eq. of 3'-O-tBDPS-thymidine, 95% of 64eq was converted to phosphite triester 65° after five hours at 50° C., while 64ax almost did not react, as determined by 31P NMR. After filtration through a short silica gel column to remove DBU, triester 65 was treated with Beaucage's reagent to give a 73:1 mixture of phosphorothioates 66, in which the major isomer is beleived to have the Rp configuration, $^{31}P$ NMR 66.76 ppm (major) and 66.59 ppm. The chiral auxiliary 1 could not be removed with 28% ammonium hydroxide, but may be removed with other reagents.

The thermodynamically more stable axially substituted cyclic indole derivatives reacted much more slowly than their equatorially substituted isomers. While not wishing to be bound by a particualr theory, the displacement leading from 63 to 64, and 64 to 65 proceed with inversion. The rapidly equilibrating mixture of slow reacting 63ax and faster reacting 63eq (ratio ~99:1) provides a 7–9:1 mixture of non-equilibrating fast reacting 64eq and slow reacting 64ax. The fast reacting indole derivative 64eq and its slow reacting isomer 64ax are then transformed with inversion to provide 65 as a mixture of diastereomers, in which one isomer, which is believed to be the isomer having the Rp configuration, is formed as the major product. Sulfurization provides a mixture of diastereomers 66 in a ratio of ~70:1.

Example 48

Preparation of Dinucleotide Phosphorothioate Triester (66)

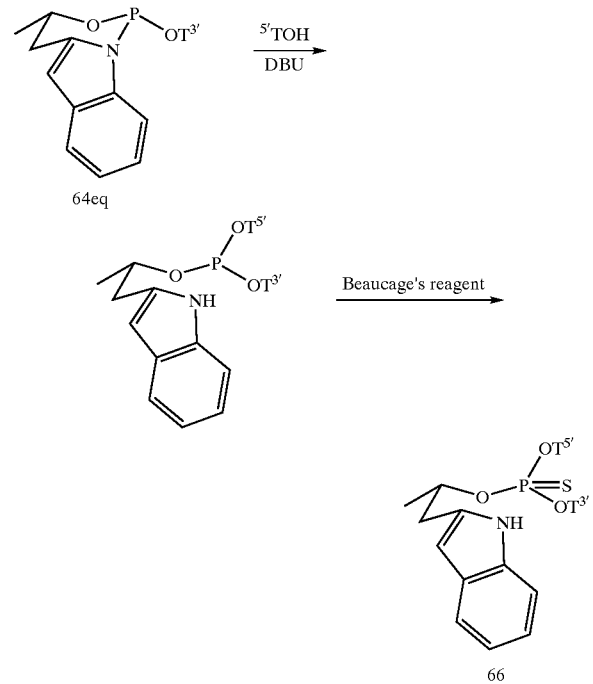

5'TOH = 3'-O-tBDPS-thymidine

In a dried 5-ml round-bottom flask was added 2 ml dried CHCl₃, indol oxazaphosphorine 64eq (50 mg, 0.085 mmol) and 3'-O-tBDPS-thymidine (40.8 mg, 0.085 mmol), flushed with argon, and sealed with a septum. DBU (14 μl, 0.094 mmol) was syringed into the flask. The reaction solution was stirred at room temperature overnight. Then the solution passed though a short silica gel column to filter out DBU, and eluted with dried CH₂Cl₂/CH₃CN (1:1). The solvent was evaporated to afford a colorless oil. The oil was redissolved in dried CH₂Cl₂ (5 ml), and Beaucage's reagent (30 mg, 0.15 mmol) was added. Evaporation of the reaction solution followed by flash chromatography (CH₂Cl₂/CH₃COCH₃ 5:1) afforded dinucleotide phosphorothioate triester 66 (71 mg, 78%) as white solid.

$^{31}$P NMR (202.3 MHz, CDCl₃): δ66.76 (98.65%), 66.59 (1.35%). $^1$H NMR (500 MHz, CDCl₃, assigned by COSY): δ9.93 (s, 1H, NH), 9.31 (s, 1H, NH-3-T$^{5'}$), 8.85 (s, 1H, NH-3-T$^{3'}$), 7.62–6.93 ( m, 16H, Si(C₆H₅)₂, C₆H₄, H-6-T$^{3'}$, H-6-T$^{5'}$), 6.46 (dd, 1H, $^3$J=8.0 Hz, $^3$J=6.0 Hz, H-1'-T$^{5'}$), 6.26 (s, 1H, CH—Ph), 6.05 (dd, 1H, $^3$J=9.2 Hz, $^3$J=5.5 Hz, H-1'-T$^{3'}$), 4.92 (m, 1H, CHOP), 4.76 (m, 1H, H-3'-T$^{3'}$), 4.31 (m, 1H, H-3'-T$^{5'}$), 4.03 (m, 1H, H-4'-T$^{5'}$), 3.82 (m, 1H, H-4'-T$^{3'}$), 3.80, 3.50 (m, 2H, H-5', H-5"-T$^{5'}$), 3.67, 3.58 (m, 2H, H-5', H-5"-T$^{3'}$), 3.00 (m, 2H, CH₂), 2.31 (m, 1H, H-2'-T$^{5'}$), 1.94 (s, 3H, CH₃C-5-T$^{5'}$), 1.90 (s, 3H, CH₃C-5-T$^{3'}$), 1.85 (m, 1H, H-2"-T$^{5'}$), 1.60 (m, 1H, H-2'-T$^{3'}$), 1.26 (d, 3H, $^3$J=6.0 Hz, CH₃), 1.14 (m, 1H, H-2"-T$^{3'}$), 1.80 (s, 9H, SiC(CH₃)₃-T$^{5'}$), 0.89 (s, 9H, SiC(CH₃)₃-T$^{3'}$), 0.07 (d, 6H, Si(CH₃)₂). $^{13}$C NMR (125.7 MHz, CDCl₃, assigned by HMQC): S 163.84, 163.80 (C-4-T$^3$, C-4-T$^5$), 150.74, 150.34 (C-2-T$^3$, C-2-T$^5$), 135.52, 135.49, 135.25, 134.56, 134.16, 132.73, 132.55, 130.15, 130.05, 128.48, 127.91, 127.85, 120.99, 119.59, 119.34, 111.24, 110.41 (C₆H₅SiC₆H₅, C₆H₅NC, C-6-T$^3$, C-6-T$^5$), 100.69 (PhCH), 85.29, 85.17 (C-4'-T$^3$, C-4'-T$^5$), 84.87 (C-1'-T$^{5'}$), 84.27 (C-1'-T$^{3'}$), 79.70 (C-3'-T$^{3'}$), 76.82 (CH), 73.31 (C-3'-T$^5$), 66.83 (C-5'-T$^5$), 63.01 (C-5'-T$^{3'}$), 40.17 (C-2'-T$^5$), 37.59 (C-2'-T$^{3'}$), 36.00 (CH₂), 26.67 (C(CH₃)₃-T$^5$), 25.77 (C(CH₃)₃-T$^{3'}$), 21.24 (CH₃), 18.81, 18.15 (SiC-T$^3$, SiC-T$^5$), −5.61, −5.56 (CH₃SiCH₃). MS (FAB, M+H): 1072. m.p. 115–116 °C.

Example 49

(R) -Glycidyl-tert-butyldimethylsilyl ether

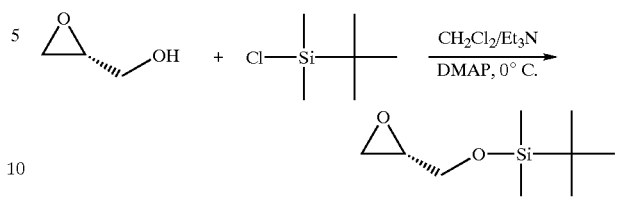

To a solution of (R)-glycidol (5 g, 67.5 mmol) in dry dichloromethane containing triethylamine (10.3 ml, 74 mmol) cooled down to 0° C., was added a solution of tert-butyldimethylsilyl chloride (11.2 g, 74 mmol) in dry dichloromethane (30 ml). Then DMAP ( 0.33 g, 2.7 mmol) was added. The mixture was allowed to warm up to room temperature and stirred for 5 hours. The triethylammonium chloride crystals were filtered out and washed with dichloromethane (2×10 ml). The organic solution was washed with brine (2×50 ml) and dried over anhydrous sodium sulfate. The solution was concentrated and passed though a short silica gel column to remove polar impurities, and eluted with hexane/ethyl acetate (3:2). After removing the solvent, a colourless oil was collected and dried in vacuo to provide pure (S)-glycidyl-tert-butyldimethylsilyl ether (10.3 g, 81.2%).

$^1$H NMR (270 Mhz, CDCl3): 3.81, 3.61 (m, 2H, CH2OSi), 3.04 (m, 1H, CH), 2.72, 2.59 (m, 2H, CH2O), 0.86 (s, 9H, C(CH3)3), 0.036 (d, 6H, Si(CH3)2). $^{13}$C NMR (67.9 Mhz, CDCl3): 63.78 (CH2OSi), 52.44 (CH2O), 44.45 (CHO), 25.90 ((CH3)3), 18.38 (Csi), −5.28, −5.32 (CH3SiCH3).

Preparation of chiral auxiliaries 67 to 69 are shown in the following Scheme:

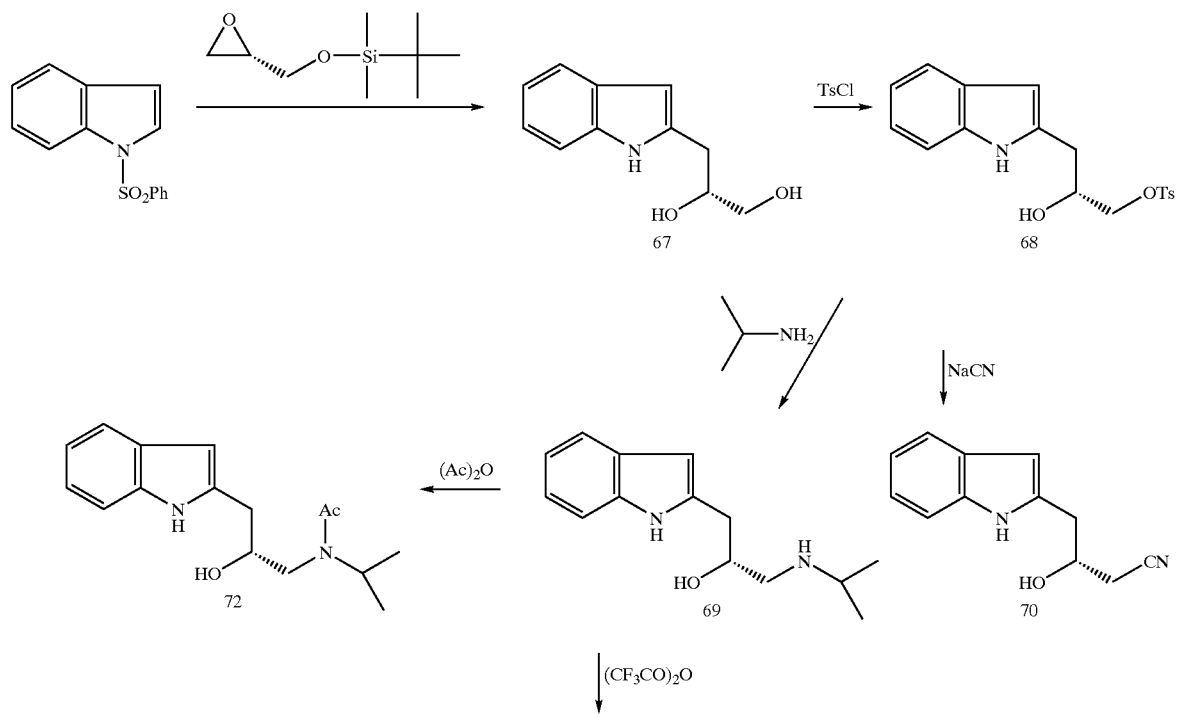

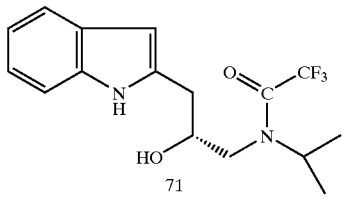

71

The chiral auxiliaries 70–72 are removable with standard reagents useful for the removal of phosphorus protecting groups.

Example 50

(R)-3-indol-2-yl-propane-1,2-diol (67)

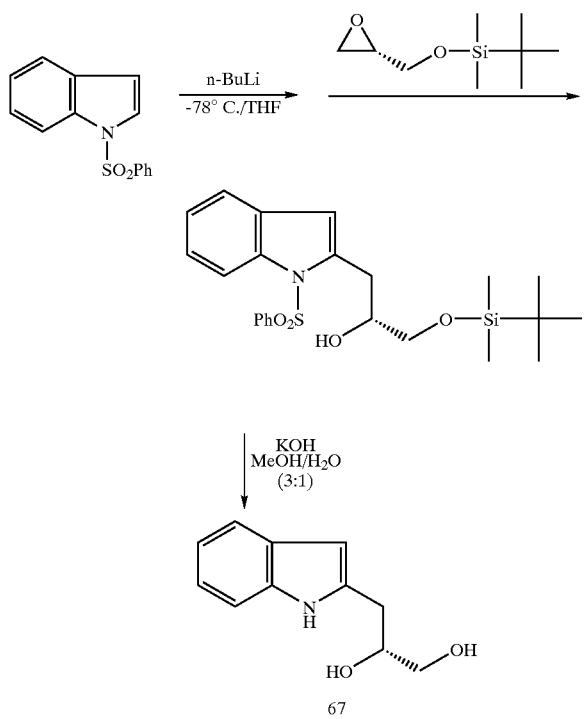

To a solution of 1-phenylsulfonyl-indole (6.2 g, 24 mmol) in dry THF (60 ml) under argon at −78° C. was added dropwise via syringe over 10 min a solution of 1.6 M butyllithium (15 ml, 24 mmol). The mixture was stirred for 1.5 h below −70° C. and then allowed to warm slowly to 5° C. over 1 h. The solution was cooled to −78° C. and then treated via syringe with a solution of (S)-glycidyl-tert-butyldimethylsilyl ether (4.5 g, 24 mmol) in dry THF (10 ml). The mixture was allowed to warm slowly to room temperature overnight, poured into saturated NH$_4$Cl solution (80 ml). The solution was extracted with ethyl acetate (3×40 ml). The combined extracts were washed with H$_2$O (2×100 ml), saturated sodium bicarbonate solution (2×100 ml) and brine (2×100 ml), dried over anhydrous sodium sulphate, and rotary evaporated to afford a deep red oil. This oil was purified by silica gel chromatography (ethyl acetate/hexane 1:1) to provide (R)-1-tert-butyldimethylsiloxyl-3-(1-phenylsulfonylindol-2-yl)-propan-2-ol as a light red oil (5.2 g, 46%).

$^1$H NMR (500 MHz, CDCl$_3$): δ7.19–8.16 (m, 9H, C$_6$H$_5$, C$_6$H$_4$), 6.57 (s, 1H, NCCH), 4.14 (m, 1H, CHO), 3.74, 3.58 (m, 2H, CH2OSi), 3.23, 3.09 (m, 2H, CH2C), 2.57 (d, 1H, $^3$J=4.5 Hz, OH), 0.93 (s, 9H, (CH3)3), 0.10 (d, 6H, CH3SiCH3). $^{13}$C NMR (75.4 MHz, CDCl$_3$): δ138.95, 138.32, 137.30, 133.66, 129.83, 129.22, 126.20, 124.19, 123.73, 120.37, 114.93, 111.25, 70.88, 66.52, 33.03, 25.90, 18.30.

Cleavage of the phenylsulfonyl protecting group was achieved with potassium hydroxide. 4.5 g (R)-1-tert-butyldimethylsiloxyl-3-(1-phenylsulfonylindol-2-yl)-propan-2-ol was dissolved in 50 ml methanol/water (3:1) containing 2.8 g KOH. The solution was refluxed for 5 hours and extracted with ethyl acetate (2×50 ml). The combined extracts were washed with H$_2$O (2×100 ml) and brine (2×100 ml), dried over anhydrous sodium sulphate, and evaporated to afford pure (R)-3-indol-2-yl-propane-1,2-diol (1.68 g, 86.9%) as a light amber oil.

$^1$H NMR (270 MHz, CDCl$_3$): δ8.58 (s, 1H, NH), 7.53–7.00 (m, 4H, C$_6$H$_4$), 6.21 (s, 1H, NCCH), 3.88 (m, 1H, CHO), 3.56, 3.40 (m, 2H, CH2O), 3.2 (s, br, 1H, OH), 2.79 (m, 2H, CH2C), 2.00 (s, broad, 1H, OH). $^{13}$C NMR (67.9 MHz, CDCl$_3$): δ136.24, 135.71, 128.46, 121.45, 119.96, 119.78, 110.75 (C6H4NC), 100.93 (CHCN), 71.80 (CHO), 66.06 (CH2C), 31.87 (CH2OH).

Example 51

1-p-toluenesulfonic-3-indol-2-yl-propan-2-ol (68)

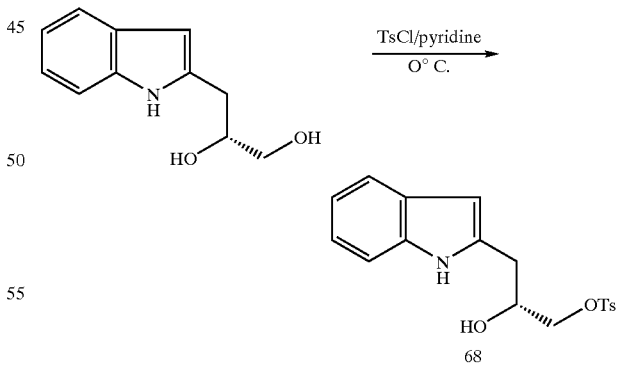

To a solution of (R)-3-indol-2-yl-propane-1,2-diol (1.20 g, 6.28 mmol) in dry pyridine (60 ml) cooled down to 0° C., was added p-toluenesulfonyl chloride (1.20 g, 6.29 mmol). After stirring for 5 hours at 0° C., the solution was poured into 100 ml cold water and extracted with ether (3×30 ml). The combined extracts were washed with 6 N hydrochloric acid (2×50 ml), brine (2×50 ml), dried over anhydrous sodium sulphate, and evaporated to give 1-p-toluenesulfonic-3-indol-2-yl-propan-2-ol as white solid (1.70 g, 78.6%), which was not purified for the next reactions.

$^1$H NMR (270 Mhz, CDCl3): 8.63 (s, broad, 1H, NH), 7.0–7.7 (m, 8H, C6H4, C6H4SO2), 4.13 (m, 1H, CHO), 3.99 (m, 2H, CH2O), 2.89 (m, 2H, CH2C), 2.41 (s, 3H, CH3).

Example 52

Hydroxycyanopropylindole 70

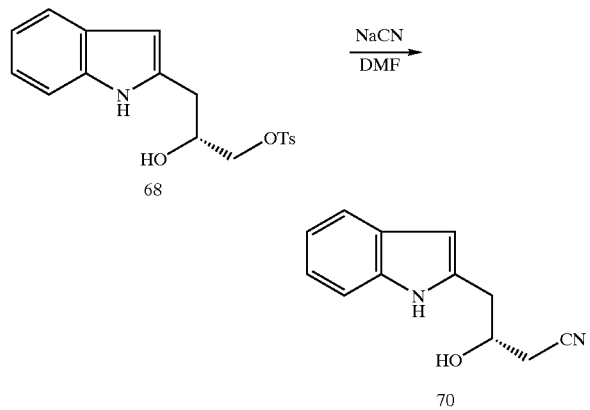

A solution of tosylate 68 (1.62 g, 4.7 mmol) in DMF (30 ml) containing sodium cyanide (0.5 g, 10.2 mmol) was stirred for four hours at 110° C., then cooled down to room temperature, poured into 80 ml ice-water, and extracted with ethyl acetate (330 ml). The combined organic solution was washed with saturated sodium bicarbonate (230 ml), brine (230 ml), dried over anhydrous sodium sulfate, and evaporated to yield a deep red oil. This oil was purified by flash chromatography (hexane:ethyl acetate 2:3) to give nitrile 10 (0.6 g. 64%).

$^1$H NMR (270 MHz, CDCl3): 8.42 (s, broad, 1H, NH), 7.0–7.5 (m, 4H, C6H4), 6.30(d, 1H, $^4$J=1.48 Hz, CHCN), 4.20 (m, 1H, CHO), 3.01 (m, 2H, CH2), 2.47, 2.49 (m, 2H, CH2CN). $^{13}$C NMR (67.9 Mhz, CDCl$_3$): 136.56, 133.58, 1218.55, 121.94, 120.16, 120.06, 110.74, 102.12 (C8H5N), 117.12 (CN), 67.55 (CH2C), 35.10 (CHO), 25.28 (CH2CN).

Example 53

Amino compound 69

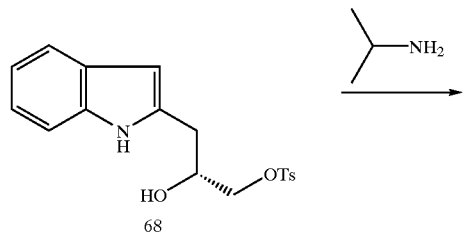

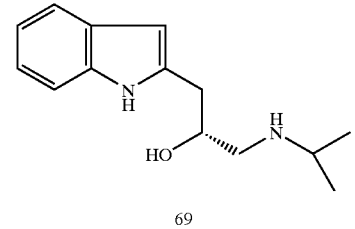

To a pressure vessel was added 2.94 g of 68 and 10 ml isopropylamine. The mixture was stirred overnight at 110° C. Evaporation of the solvent afforded a amber oil which was purified by flash chromatography to provide 69 (1.6 g, 81%).

$^1$H NMR (270 Mhz, CDCl3): 9.01 (s, broad., 1H, NH), 7.0–7.5 (m, 4H, C6H4), 6.23(s, 1H, CHCN), 3.89 (m, 1H, CHO), 2.72–3.03 (m, 5H, NCH, OH, NH, CH2), 2.44, 2.59 (m, 2H, CH2N), 1.05, 1.04 (d, 6H, $^3$J=6.18 Hz, (CH3)2). $^{13}$C NMR (67.9 MHz, CDCl$_3$): 136.61, 136.28, 128.43, 121.12, 119.81, 119.46, 110.73, 100.68 (C8H5N), 69.37, 51.80, 49.04, 33.34, 23.12, 22.81.

Example 54

Compound 72

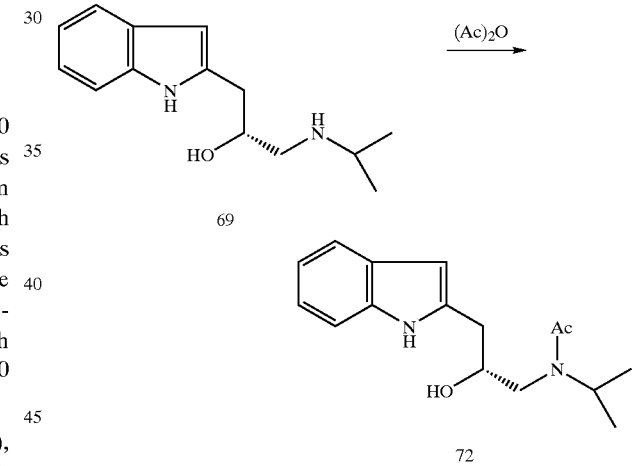

To a solution of 69 (0.2 g, 0.86 mmol) in dry CH$_3$CN (20 ml) was added acetic anhydride (0.1 ml, 1.06 mmol). The mixture was stirred for four hours at room temperature, then washed with saturated sodium bicarbonate solution (210 ml), brine (210 ml), and dried ove anhydrous sodium sulfate. The solvent was evaporated ant residual solid was purified on flash chromatography (ethyl acetate) to compound 72 as a colourless crystals (0.22 g, 92%).

$^1$H NMR (270 Mhz, CDCl3): 9.17 (s, broad, 1H, NH), 7.0–7.5 (m, 4H, C6H4), 6.25(s, 1H, CHCN), 3.98 (m, 2H, CHO, CHN), 3.50, 3.10 (m, 2H, CH2), 2.94 (m, 2H, CH2N), 2.15 (s, 3H, CH3CO),1.14, 1.12 (d, 6H, $^3$J=6.42 Hz, (CH3) 2). $^{13}$C NMR (67.9 MHz, CDCl$_3$): 173.58 (CO), 136.34, 136.16, 128.24, 121.17, 119.70, 119.41, 110.89, 100.85 (C$_8$H$_5$N), 73.41, 50.15, 47.92, 34.12, 21.32, 20.73.

Those skilled in the art will appreciate that numerous changes and modifications may be made to the preferred embodiments of the invention and that such changes and modifications may be made without departing from the spirit of the invention. It is therefore intended that the appended claims cover all equivalent variations as fall within the true spirit and scope of the invention.

It is intended that each of the patents, publications, and other published documents mentioned or referred to in this specification be herein incorporated by reference in their entirety.

What is claimed is:

1. A method for the preparation of an internucleotide linkage comprising the steps of:
   selecting a first nucleoside synthon having an activated phosphorus group;
   providing a second synthon having a free 5'-hydroxyl group, said second synthon being a mononucleoside synthon or a polynucleotide synthon; and
   reacting said first nucleoside synthon with said second synthon in the presence of a catalyst to form said internucleotide linkage;
   said catalyst having the formula:

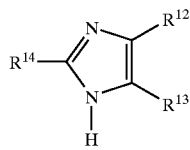

wherein:
   $R^{12}$ and $R^{13}$ are each independently halogen; and
   $R^{14}$ is hydrogen, halogen, cyano, nitro, thio, alkyl having from one to 10 carbons, substituted alkyl having from one to 10 carbons, norbornyl, substituted norbornyl, aryl, substituted aryl wherein said substituents are electron withdrawing, or has the formula:

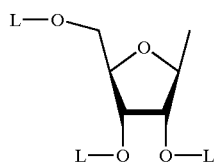

wherein
   L is protecting group;
   provided that when $R^{12}$ and $R^{13}$ are each chlorine, $R^{14}$ is not hydrogen;
   wherein said method is performed in solution or on a solid support.

2. The method of claim 1 wherein said first nucleoside synthon is a nucleoside phosphoramidite.

3. The method of claim 1 wherein said internucleotide linkage is a phosphite linkage.

4. The method of claim 1 wherein $R^{12}$ and $R^{13}$ are each chlorine.

5. The method of claim 1 wherein $R^{12}$ and $R^{13}$ are each bromine.

6. The method of claim 1 wherein one of $R^{12}$ or $R^{13}$ is chlorine and the other of $R^{12}$ or $R^{13}$ is bromine.

7. The method of claim 1 wherein $R^{14}$ is hydrogen, halogen, cyano, nitro, thio, or alkyl having from one to 10 carbons.

8. The method of claim 1 wherein $R^{14}$ is hydrogen, halogen, or cyano.

9. The method of claim 1 wherein $R^{14}$ is hydrogen or cyano.

10. The method of claim 1 wherein $R^{12}$ and $R^{13}$ are each independently chlorine or bromine; and $R^{14}$ is hydrogen or cyano.

11. The method of claim 1 wherein $R^{12}$ and $R^{13}$ are each independently chlorine or bromine; and $R^{14}$ is cyano.

12. The method of claim 1 further comprising the step of oxidizing said internucleotide linkage to form a phosphodiester linkage, a phosphorothioate linkage, or a phosphorodithioate linkage.

13. A method for the preparation of an internucleotide linkage comprising the steps of:
    selecting a first nucleoside synthon having an activated phosphorus group;
    providing a second synthon, said second synthon being bound to a solid support, and having a free 5'-hydroxyl group, said second synthon being a mononucleoside synthon or a polynucleotide synthon; and
    reacting said first nucleoside synthon with said second synthon in the presence of a catalyst to form said internucleotide linkage;
    said catalyst having the formula:

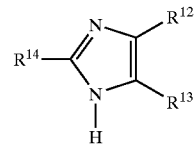

wherein:
    $R^{12}$ and $R^{13}$ are each independently halogen; and
    $R^{14}$ is hydrogen, halogen, cyano, nitro, thio, alkyl having from one to 10 carbons, substituted alkyl having from one to 10 carbons, norbornyl, substituted norbornyl, aryl, substituted aryl wherein said substituents are electron withdrawing, or has the formula:

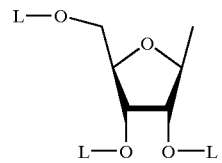

wherein L is protecting group.

14. The method of claim 13 wherein said first nucleoside synthon is a nucleoside phosphoramidite.

15. The method of claim 13 wherein said internucleotide linkage is a phosphite linkage.

16. The method of claim 13 wherein $R^{12}$ and $R^{13}$ are each chlorine.

17. The method of claim 13 wherein $R^{12}$ and $R^{13}$ are each bromine.

18. The method of claim 13 wherein one of $R^{12}$ or $R^{13}$ is chlorine and the other of $R^{12}$ or $R^{13}$ is bromine.

19. The method of claim 13 wherein $R^{14}$ is hydrogen, halogen, cyano, nitro, thio, or alkyl having from one to 10 carbons.

20. The method of claim 13 wherein $R^{14}$ is hydrogen, halogen, or cyano.

21. The method of claim 13 wherein $R^{14}$ is hydrogen or cyano.

22. The method of claim 13 wherein $R^{12}$ and $R^{13}$ are each independently chlorine or bromine; and $R^{14}$ is hydrogen or cyano.

23. The method of claim 13 wherein $R^{12}$ and $R^{13}$ are each independently chlorine or bromine; and $R^{14}$ is cyano.

24. The method of claim 13 further comprising the step of oxidizing said internucleotide linkage to form a phosphodiester linkage, a phosphorothioate linkage, or a phosphorodithioate linkage.

25. A method for solid phase nucleotide synthesis comprising the step of reacting a nucleoside phosphoramidite with the free 5'-hydroxyl group of a support-bound mononucleoside or polynucleotide in the presence of a catalyst to form an phosphite internucleoside linkage;

wherein aid catalyst has the formula:

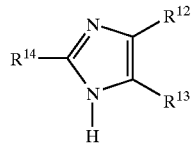

wherein:
$R^{12}$ and $R^{13}$ are each independently halogen; and
$R^{14}$ is hydrogen, halogen, cyano, nitro, thio, alkyl having from one to 10 carbons, substituted alkyl having from one to 10 carbons, norbornyl, substituted norbornyl, aryl, substituted aryl wherein said substituents are electron withdrawing, or has the formula:

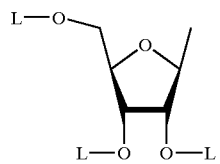

wherein L is protecting group.

26. A method comprising the steps of:
reacting a nucleoside 3'-phosphoramidite with the free 5'-hydroxyl group of a support-bound mononucleoside or polynucleotide to form an phosphite internucleoside linkage;
wherein said reaction is performed in the presence of a catalyst having the formula:

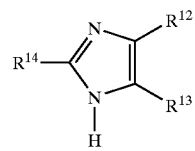

wherein:
$R^{12}$ and $R^{13}$ are each independently halogen; and
$R^{14}$ is hydrogen, halogen, cyano, nitro, thio, alkyl having from one to 10 carbons, substituted alkyl having from one to 10 carbons, norbornyl, substituted norbornyl, aryl, substituted aryl wherein said substituents are electron withdrawing, or has the formula:

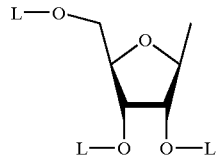

wherein L is protecting group.

* * * * *